United States Patent [19]

Hatton et al.

[11] Patent Number: 4,459,150

[45] Date of Patent: Jul. 10, 1984

[54] 5-ACYLAMINO-4-CYANO-1-PHENYL-PYRAZOLE DERIVATIVES AND USE AS HERBICIDES

[75] Inventors: Leslie R. Hatton, Chelmsford; Edgar W. Parnell, Hornchurch; David A. Roberts, Bedford, all of England

[73] Assignee: May & Baker Limited, Essex, England

[21] Appl. No.: 398,718

[22] Filed: Jul. 15, 1982

[30] Foreign Application Priority Data

Jul. 17, 1981 [GB] United Kingdom ............... 8122143
Feb. 5, 1982 [GB] United Kingdom ............... 8203371

[51] Int. Cl.³ ............... A01N 43/56; C07D 231/14; C07D 401/04
[52] U.S. Cl. ............... 71/92; 546/211; 548/362; 548/377
[58] Field of Search ............... 548/362, 377; 546/211; 71/92

[56] References Cited

U.S. PATENT DOCUMENTS 3,211,731 10/1965 Schmidt et al. ............... 548/362
4,260,775 4/1981 Plath et al. ............... 548/362

FOREIGN PATENT DOCUMENTS 26034 4/1981 European Pat. Off. .

OTHER PUBLICATIONS

Cheng et al., J. Org. Chem., 1958, vol. 23, pp. 191–200.
Kreutzberger et al., Eur. J. Med. Chem.–Chim. Ther., 1979, vol. 14, pp. 539–541.

Primary Examiner—Henry R. Jiles
Assistant Examiner—Kurt G. Briscoe
Attorney, Agent, or Firm—Stevens, Davis, Miller & Mosher

[57] ABSTRACT

New acylamino-N-phenylpyrazole derivatives of the formula:

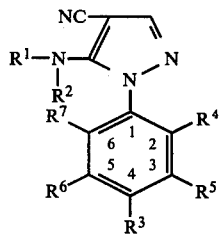

[wherein $R^1$ represents $R^8C(=O)$—(wherein $R^8$ represents H, $C_{1-7}$alkyl or $C_{1-4}$alkoxy optionally substituted by $C_{1-4}$alkoxy, $C_{2-5}$alkoxycarbonyl or halogen, $C_{3-4}$alkenyloxy, $C_{3-6}$cycloalkyl optionally substituted by $CH_3$ or $C_2H_5$, or phenoxy, $R^2$ represents H or $R^8C(=O)$—, or $R^1$ and $R^2$ together represent $-CO-(CR^aR^b)_m-CO-$, $R^3$ represents F, Cl, Br, $C_{1-4}$alkyl optionally substituted by halogen, or $C_{2-4}$alkenyl, $R^4$ represents F, Cl, Br, $NO_2$, $CH_3$ or $C_2H_5$ and $R^5$, $R^6$ and $R^7$ represent H, F, Cl, Br, $NO_2$, $CH_3$ or $C_2H_5$, or $R^4$ and $R^5$ each represent Cl and $R^3$, $R^6$ and $R^7$ each represent H, $R^a$ and $R^b$ represent H or $C_{1-4}$alkyl, and m is 2 or 3] possess useful herbicidal properties.

42 Claims, No Drawings

5-ACYLAMINO-4-CYANO-1-PHENYLPYRAZOLE DERIVATIVES AND USE AS HERBICIDES

This invention relates to N-phenylpyrazole derivatives, compositions containing them and their use as herbicides.

In J. Org. Chem. Vol. 23, 191–200 (1958), C. C. Cheng and R. K. Robins have described experiments for the preparation of 6-alkyl-4-hydroxypyrazole[3,4-d]pyrimidines as analogues of degradation products of pseudovitamin $B_{12}$. The authors report that these pyrazole[3,4-d]pyrimidine derivatives did not reveal any significant anti-tumour activity but affected the growth of bacteria. They employed, as starting materials, 1-phenyl-5-acetylamino-4-cyanopyrazoles of the general formula:

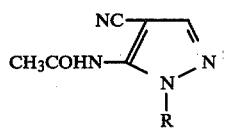

I wherein R represents phenyl, 2-chlorophenyl, 4-chlorophenyl, 4-bromophenyl, 4-nitrophenyl or 4-methylphenyl. The compound of general formula I wherein R represents a phenyl group has also been described by T. Higashino, Y. Iwai and E. Hayashi, Chem. Pharm. Bull, 24 (12), 3120–3134 (1976), as an intermediate in the preparation of 1-phenyl-1H-pyrazolo[3,4-d]pyrimidine-5-oxide. Neither of these publications contains any suggestion that compounds of general formula I possess or would be expected to possess herbicidal activity.

It has now unexpectedly been found after extensive research and experimentation that certain acylamino-N-phenylpyrazole derivatives possess valuable herbicidal properties.

The present invention accordingly provides, as herbicides, new acylamino-N-phenylpyrazole derivatives of the general formula:

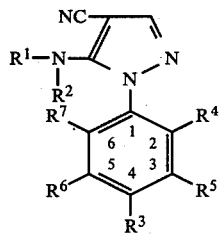

II wherein $R^1$ represents an $R^8C(=O)-$ group, wherein $R^8$ represents a hydrogen atom, a straight- or branched-chain alkyl group containing from 1 to 7 carbon atoms, a straight- or branched-chain alkoxy group containing from 1 to 4 carbon atoms or a straight- or branched-chain alkenyloxy group containing 3 or 4 carbon atoms, alkyl and alkoxy groups within the definition of $R^8$ being unsubstituted or substituted by a straight- or branched-chain alkoxy group containing from 1 to 4 carbon atoms, an alkoxycarbonyl group containing from 2 to 5 carbon atoms, or one or more halogen, e.g. chlorine, atoms, or $R^8$ represents a cycloalkyl group containing from 3 to 6 carbon atoms unsubstituted or substituted by a methyl or ethyl group, or $R^8$ represents a phenoxy group, $R^2$ represents a hydrogen atom or an $R^8C(=O)-$ group, wherein $R^8$ is as hereinbefore defined, or $R^1$ and $R^2$ together represent $-CO-(CR^aR^b)_m-CO-$, $R^3$ represents a fluorine, chlorine or bromine atom, a straight- or branched-chain alkyl group containing from 1 to 4 carbon atoms, unsubstituted or substituted by one or more halogen, e.g. fluorine, atoms, for example a trifluoromethyl group, or a straight- or branched-chain alkenyl group containing from 2 to 4 carbon atoms, $R^4$ represents a fluorine, chlorine or bromine atom or a nitro, methyl or ethyl group, and $R^5$, $R^6$ and $R^7$, which may be the same or different, each represent a hydrogen, fluorine, chlorine or bromine atom or a nitro, methyl or ethyl group, or $R^4$ and $R^5$ each represent a chlorine atom and $R^3$, $R^6$ and $R^7$ each represent a hydrogen atom, $R^a$ and $R^b$, which may be the same or different, each represent a hydrogen atom or a straight- or branched-chain alkyl group containing from 1 to 4 carbon atoms, and m represents 2 or 3.

It is to be understood that when $R^1$ and $R^2$ each represent a group $R^8C(=O)-$, wherein $R^8$ is as hereinbefore defined, the aforesaid $R^8C(=O)-$ groups may be the same or different.

It is also to be understood that $-(CR^aR^b)_m-$ represents an unsubstituted ethylene or propylene group or an ethylene or propylene group in which one or more of the carbon atoms is substituted by one or two straight- or branched-chain alkyl groups containing from 1 to 4 carbon atoms.

It is also to be understood that, unless otherwise indicated, the term 'halogen' means fluorine, chlorine, bromine or iodine.

Preferably, $R^1$ represents an $R^{8'}C(=O)-$ group and $R^{8'}$ represents an unsubstituted straight- or branched-chain alkyl group containing from 1 to 5 carbon atoms, e.g. methyl, ethyl, n-propyl, iso-propyl, n-butyl, sec-butyl, iso-butyl, t-butyl, n-pentyl, 1-ethylpropyl or 1-methylbutyl, an unsubstituted methoxy group or an unsubstituted or methyl-substituted cyclopropyl group; preferably $R^2$ represents a hydrogen atom or an $R^{8''}C(=O)-$ group and $R^{8''}$ represents an unsubstituted straight- or branched-chain alkyl group containing from 1 to 5 carbon atoms, e.g. methyl, ethyl, n-propyl, iso-propyl, n-butyl or iso-butyl, an unsubstituted methoxy group or an unsubstituted or methyl-substituted cyclopropyl group, $R^{8'}$ and $R^{8''}$ being the same or different; preferably $R^3$ represents $R^{3'}$ and $R^{3'}$ represents a chlorine atom or a trifluoromethyl or unsubstituted ethyl group or, when $R^{4'}$, $R^{5'}$, $R^{6'}$ and $R^{7'}$ are as hereinafter defined, each represents a fluorine atom, an unsubstituted methyl group; preferably $R^4$ represents $R^{4'}$ and $R^{4'}$ represents a fluorine or chlorine atom; preferably $R^5$ represents $R^{5'}$ and $R^{5'}$ represents a hydrogen, fluorine or chlorine atom; preferably $R^6$ represents $R^{6'}$ and $R^{6'}$ represents a hydrogen or fluorine atom; preferably $R^7$ represents $R^{7'}$ and $R^{7'}$ represents a hydrogen, fluorine or chlorine atom.

Particularly preferred compounds of general formula II as herbicides are those wherein $R^1$ represents an $R^{8'}C(=O)-$ group, wherein $R^{8'}$ is as hereinbefore defined, $R^2$ represents a hydrogen atom or an $R^{8''}C(=O)-$ group, wherein $R^{8''}$ is as hereinbefore defined, $R^{8'}$ and $R^{8''}$ being the same or different, and $R^3$, $R^4$, $R^5$, $R^6$ and $R^7$ each represent, respectively, $R^{3'}$, $R^{4'}$, $R^{5'}$, $R^{6'}$ and $R^{7'}$, wherein $R^{3'}$, $R^{4'}$, $R^{5'}$, $R^{6'}$ and $R^{7'}$ are as hereinbefore defined.

The following compounds of general formula II are of particular interest as herbicides.

| No | Compound |
|---|---|
| 1 | 5-acetamido-4-cyano-1-(2,3,4-trichlorophenyl)pyrazole |
| 2 | 4-cyano-5-diacetylamino-1-(2,3,4-trichlorophenyl)pyrazole |
| 3 | 5-acetamido-4-cyano-1-(2,3,5,6-tetrafluoro-4-trifluoromethylphenyl)pyrazole |
| 4 | 4-cyano-5-di(phenoxycarbonyl)amino-1-(2,3,4-trichlorophenyl)pyrazole |
| 5 | 4-cyano-5-propionamido-1-(2,3,4-trichlorophenyl)pyrazole |
| 6 | 5-acetamido-4-cyano-1-(2,4,6-trichlorophenyl)pyrazole |
| 7 | 4-cyano-5-diacetylamino-1-(4-methyl-2,3,5,6-tetrafluorophenyl)pyrazole |
| 8 | 5-acetamido-4-cyano-1-(4-methyl-2,3,5,6-tetrafluorophenyl)pyrazole |
| 9 | 5-acetamido-4-cyano-1-(2,3,6-trichloro-4-trifluoromethylphenyl)pyrazole |
| 10 | 5-acetamido-4-cyano-1-(2,3,4,6-tetrachlorophenyl)pyrazole |
| 11 | 5-acetamido-1-(2-chloro-4-methylphenyl)-4-cyanopyrazole |
| 12 | 5-acetamido-1-(4-allyl-2,3,5,6-tetrafluorophenyl)-4-cyanopyrazole |
| 13 | 5-acetamido-1-(2-chloro-4-ethylphenyl)-4-cyanopyrazole |
| 14 | 4-cyano-5-dipropionylamino-1-(2,3,4-trichlorophenyl)pyrazole |
| 15 | 5-n-butyramido-4-cyano-1-(2,3,4-trichlorophenyl)pyrazole |
| 16 | 4-cyano-5-isobutyramido-1-(2,3,4-trichlorophenyl)pyrazole |
| 17 | 4-cyano-5-n-pentanamido-1-(2,3,4-trichlorophenyl)pyrazole |
| 18 | 4-cyano-5-(3-methylbutyramido)-1-(2,3,4-trichlorophenyl)pyrazole |
| 19 | 4-cyano-5-n-heptanamido-1-(2,3,4-trichlorophenyl)pyrazole |
| 20 | 4-cyano-5-n-hexanamido-1-(2,3,4-trichlorophenyl)pyrazole |
| 21 | 4-cyano-5-n-octanamido-1-(2,3,4-trichlorophenyl)pyrazole |
| 22 | 5-acetamido-4-cyano-1-(2,3-dichlorophenyl)pyrazole |
| 23 | 5-acetamido-4-cyano-1-(2,4-dichlorophenyl)pyrazole |
| 24 | 4-cyano-5-(2-methylbutyramido)-1-(2,3,4-trichlorophenyl)pyrazole |
| 25 | 4-cyano-5-(2-ethylbutyramido)-1-(2,3,4-trichlorophenyl)pyrazole |
| 26 | 4-cyano-5-cyclopentylcarbonamido-1-(2,3,4-trichlorophenyl)pyrazole |
| 27 | 4-cyano-5-cyclopropylcarbonamido-1-(2,3,4-trichlorophenyl)pyrazole |
| 28 | 4-cyano-5-(2,2-dimethylpropionamido)-1-(2,3,4-trichlorophenyl)pyrazole |
| 29 | 4-cyano-5-propionamido-1-(2,3,5,6-tetrafluoro-4-trifluoromethylphenyl)pyrazole |
| 30 | 1-(2-chloro-4-ethylphenyl)-4-cyano-5-propionamidopyrazole |
| 31 | 4-cyano-5-propionamido-1-(2,3,4,6-tetrachlorophenyl)pyrazole |
| 32 | 4-cyano-5-formamido-1-(2,3,4-trichlorophenyl)pyrazole |
| 33 | 4-cyano-5-(2-ethylhexanamido)-1-(2,3,4-trichlorophenyl)pyrazole |
| 34 | 4-cyano-5-(2-ethyl-3-methylbutyramido)-1-(2,3,4-trichlorophenyl)pyrazole |
| 35 | 5-acetamido-4-cyano-1-(4-methyl-2,3,6-trichlorophenyl)pyrazole |
| 36 | 5-acetamido-4-cyano-1-(2,3-dichloro-4-ethylphenyl)-pyrazole |
| 37 | 5-acetamido-1-(2-chloro-4-isopropylphenyl)-4-cyanopyrazole |
| 38 | 1-(2-chloro-4-methylphenyl)-4-cyano-5-propionamidopyrazole |
| 39 | 1-(2-chloro-4-isopropylphenyl)-4-cyano-5-propionamidopyrazole |
| 40 | 4-cyano-5-propionamido-1-(2,3,6-trichloro-4-trifluoromethylphenyl)pyrazole |
| 41 | 5-n-butyramido-4-cyano-1-(2,3,5,6-tetrafluoro-4-trifluoromethylphenyl)pyrazole |
| 42 | 4-cyano-5-isobutyramido-1-(2,3,5,6-tetrafluoro-4-trifluoromethylphenyl)pyrazole |
| 43 | 4-cyano-5-cyclopropylcarbonamido-1-(2,3,5,6-tetrafluoro-4-trifluoromethylphenyl)pyrazole |
| 44 | 4-cyano-5-(2-ethylbutyramido)-1-(2,3,5,6-tetrafluoro-4-trifluoromethylphenyl)pyrazole |
| 45 | 4-cyano-5-cyclohexylcarbonamido-1-(2,3,4-trichlorophenyl)pyrazole |
| 46 | 4-cyano-5-[(2-ethoxy)ethoxy-carbonylamino]-1(2,3,4-trichlorophenyl)pyrazole |
| 47 | 4-cyano-5-methoxycarbonylamino-1-(2,3,4-trichlorophenyl)pyrazole |
| 48 | 4-cyano-5-isopropoxycarbonylamino-1-(2,3,4-trichlorophenyl)pyrazole |
| 49 | 5-n-butoxycarbonylamino-4-cyano-1-(2,3,4-trichlorophenyl)pyrazole |
| 50 | 4-cyano-5-n-propoxycarbonylamino-1-(2,3,4-trichlorophenyl)pyrazole |
| 51 | 4-cyano-5-ethoxycarbonylamino-1-(2,3,4-trichlorophenyl)pyrazole |
| 52 | 5-t-butoxycarbonylamino-4-cyano-1-(2,3,4-trichlorophenyl)pyrazole |
| 53 | 4-cyano-5-(2-propenyloxycarbonylamino)-1-(2,3,4-trichlorophenyl)pyrazole |
| 54 | 1-(2-chloro-4-trifluoromethylphenyl)-4-cyano-5-methoxycarbonylaminopyrazole |
| 55 | 4-cyano-5-methoxycarbonylamino-1-(2,3,5,6-tetrafluoro-4-trifluoromethylphenyl)pyrazole |
| 56 | 4-cyano-5-ethoxycarbonylamino-1-(2,3,5,6-tetrafluoro-4-trifluoromethylphenyl)pyrazole |
| 57 | 4-cyano-5-diacetylamino-1-(2,3,5,6-tetrafluoro-4-trifluoromethylphenyl)pyrazole |
| 58 | 1-(2-chloro-4-trifluoromethylphenyl)-4-cyano-5-diacetylaminopyrazole |
| 59 | 4-cyano-5-diacetylamino-1-(2,4,6-trichlorophenyl)pyrazole |
| 60 | 4-cyano-5-diacetylamino-1-(2,4-dichlorophenyl)pyrazole |
| 61 | 1-(2-chloro-4-trifluoromethylphenyl)-4-cyano-5-propionamidopyrazole |
| 62 | 5-n-butyramido-1-(2-chloro-4-trifluoromethylphenyl)-4-cyanopyrazole |
| 63 | 1-(2-chloro-4-trifluoromethylphenyl)-4-cyano-5-(3-methylbutyramido)pyrazole |
| 64 | 1-(2-chloro-4-trifluoromethylphenyl)-4-cyano-5-cyclopropylcarbonamidopyrazole |
| 65 | 5-acetamido-1-(2-chloro-4-trifluoromethylphenyl)-4-cyanopyrazole |
| 66 | 5-acetamido-1-(4-n-butyl-2,3,5,6-tetrafluorophenyl)-4-cyanopyrazole |
| 67 | 5-acetamido-4-cyano-1-(4-ethyl-2,3,5,6-tetrafluorophenyl)pyrazole |
| 68 | 4-cyano-1-(4-methyl-2,3,5,6-tetrafluorophenyl)-5-propionamidopyrazole |
| 69 | 4-cyano-5-diacetylamino-1-(4-ethyl-2,3,5,6-tetrafluorophenyl)pyrazole |
| 70 | 5-acetamido-1-(4-bromo-2,3-dichlorophenyl)-4-cyanopyrazole |
| 71 | 5-acetamido-4-cyano-1-(2-nitro-4-trifluoromethylphenyl)pyrazole |
| 72 | 5-acetamido-4-cyano-1-(2,6-dichloro-4-trifluoromethylphenyl)pyrazole |
| 73 | 4-cyano-1-(2,6-dichloro-4-trifluoromethylphenyl)-5-propionamidopyrazole |
| 74 | 5-acetamido-4-cyano-1-(pentafluorophenyl)pyrazole |
| 75 | 4-cyano-5-propionamido-1-(2,4,6-trichlorophenyl)pyrazole |
| 76 | 4-cyano-1-(2,4-dichlorophenyl)-5-propionamidopyrazole |
| 77 | 5-isobutyramido-1-(2-chloro-4-trifluoromethylphenyl)-4-cyanopyrazole |
| 78 | 4-cyano-5-dichloroacetamido-1-(2,3,4-trichlorophenyl)-pyrazole |
| 79 | 4-cyano-5-cyclobutylcarbonamido-1-(2,3,4-trichlorophenyl)pyrazole |
| 80 | 5-(4-chlorobutyramido)-4-cyano-1-(2,3,4-trichlorophenyl)pyrazole |
| 81 | 4-cyano-1-(2,3-dichlorophenyl)-5-propionamidopyrazole |
| 82 | 4-cyano-5-di(phenoxycarbonyl)amino-1-(2,3,5,6-tetrafluoro-4-trifluoromethylphenyl)pyrazole |
| 83 | 1-(2-chloro-4-trifluoromethylphenyl)-4-cyano-5-di(phenoxycarbonyl)aminopyrazole |
| 84 | 1-(2-chloro-4-n-propylphenyl)-4-cyano-5-diacetylaminopyrazole |
| 85 | 4-cyano-5-diacetylamino-1-(2,6-dibromo-4-trifluoromethylphenyl)pyrazole |
| 86 | 5-acetamido-4-cyano-1-(2,6-dibromo-4-trifluoromethylphenyl)pyrazole |
| 87 | 1-(2-chloro-4-trifluoromethylphenyl)-4-cyano-5-pentanamidopyrazole |
| 88 | 5-acetamido-4-cyano-1-(2,3,4,6-tetrafluorophenyl)pyrazole |
| 89 | 4-cyano-5-(3-methylbutyramido)-1-(2,3,5,6-tetrafluoro-4-trifluoromethylphenyl)pyrazole |
| 90 | 5-isobutoxycarbonylamino-4-cyano-1-(2,3,4-trichlorophenyl)pyrazole |
| 91 | 5-acetamido-1-(2-chloro-4-n-propylphenyl)-4-cyanopyrazole |
| 92 | 1-(2-chloro-4-trifluoromethylphenyl)-4-cyano-5-cyclohexylcarbonamidopyrazole |
| 93 | 1-(2-chloro-4-trifluoromethylphenyl)-4-cyano-5-(2-methylbutyramido)pyrazole |
| 94 | 5-(5-chloropentanamido)-4-cyano-1-(2,3,4-trichlorophenyl)pyrazole |

| No | Compound |
|---|---|
| 95 | 4-cyano-5-cyclohexylcarbonamido-1-(2,6-dichloro-4-trifluoromethylphenyl)pyrazole |
| 96 | 1-(2-chloro-4-trifluoromethylphenyl)-4-cyano-5-(2,2-dimethylpropionamido)pyrazole |
| 97 | 4-cyano-1-(2,6-dichloro-4-trifluoromethylphenyl)-5-(3-methylbutyramido)pyrazole |
| 98 | 5-n-butyramido-4-cyano-1-(2,6-dichloro-4-trifluoromethylphenyl)pyrazole |
| 99 | 1-(2-chloro-4-trifluoromethylphenyl)-4-cyano-5-(2-ethylbutyramido)pyrazole |
| 100 | 4-cyano-1-(2,6-dibromo-4-trifluoromethylphenyl)-5-propionamidopyrazole |
| 101 | 5-(3-chloro-2,2-dimethylpropionamido)-4-cyano-1-(2,3,4-trichlorophenyl)pyrazole |
| 102 | 4-cyano-5-dichloroacetamido-1-(2,6-dichloro-4-trifluoromethylphenyl)pyrazole |
| 103 | 1-(2-chloro-4-trifluoromethylphenyl)-4-cyano-5-dichloroacetamidopyrazole |
| 104 | 4-cyano-1-(2,6-dichloro-4-trifluoromethylphenyl)-5-isobutyramidopyrazole |
| 105 | 4-cyano-5-cyclopropylcarbonamido-1-(2,6-dichloro-4-trifluoromethylphenyl)pyrazole |
| 106 | 1-(2-chloro-4-trifluoromethylphenyl)-4-cyano-5-heptanamidopyrazole |
| 107 | 4-cyano-5-cyclopentylcarbonamido-1-(2,6-dichloro-4-trifluoromethylphenyl)pyrazole |
| 108 | 4-cyano-1-(2,6-dichloro-4-trifluoromethylphenyl)-5-heptanamidopyrazole |
| 109 | 4-cyano-1-(2,6-dichloro-4-trifluoromethylphenyl)-5-methoxycarbonylaminopyrazole |
| 110 | 4-cyano-1-(2,6-dichloro-4-trifluoromethylphenyl)-5-pentanamidopyrazole |
| 111 | 1-(2-chloro-4-trifluoromethylphenyl)-4-cyano-5-cyclopentylcarbonamidopyrazole |
| 112 | 4-cyano-1-(2,6-dichloro-4-trifluoromethylphenyl)-5-(2-methylbutyramido)pyrazole |
| 113 | 4-cyano-5-(2-methylpentanamido)-1-(2,3,4-trichlorophenyl)-pyrazole |
| 114 | 5-acetamido-4-cyano-1-(2,4-dichloro-6-methylphenyl)pyrazole |
| 115 | 4-cyano-1-(2,4-dichloro-6-methylphenyl)-5-propionamidopyrazole |
| 116 | 5-acetamido-1-(4-chloro-2,3,5,6-tetrafluorophenyl)-4-cyanopyrazole |
| 117 | 1-(4-chloro-2,3,5,6-tetrafluorophenyl)-4-cyano-5-propionamidopyrazole |
| 118 | 4-cyano-5-propionamido-1-(2,3,4,6-tetrafluorophenyl)-pyrazole |
| 119 | 4-cyano-5-cyclobutylcarbonamido-1-(2,6-dichloro-4-trifluoromethylphenyl)pyrazole |
| 120 | 4-cyano-1-(2,6-dichloro-4-trifluoromethylphenyl)-5-(2,2-dimethylpropionamido)pyrazole |
| 121 | 1-(2-chloro-4-trifluoromethylphenyl)-4-cyano-5-cyclobutylcarbonamidopyrazole |
| 122 | 4-cyano-1-(2-nitro-4-trifluoromethylphenyl)-5-propionamidopyrazole |
| 123 | 4-cyano-1-(2,6-dichloro-4-trifluoromethylphenyl)-5-(2-ethylbutyramido)pyrazole |
| 124 | 4-cyano-5-isopropoxycarbonylamino-1-(2,3,5,6-tetrafluoro-4-trifluoromethylphenyl)pyrazole |
| 125 | 5-(4-chloropentanamido)-4-cyano-1-(2,3,4-trichlorophenyl)-pyrazole |
| 126 | 1-(2-chloro-4-trifluoromethylphenyl)-4-cyano-5-(2-methylpentanamido)pyrazole |
| 127 | 1-(2-chloro-4-trifluoromethylphenyl)-4-cyano-5-(2-ethyl-3-methylbutyramido)pyrazole |
| 128 | 5-acetamido-4-cyano-1-(2,6-dichloro-4-ethylphenyl)pyrazole |
| 129 | 4-cyano-5-succinimido-1-(2,3,4-trichlorophenyl)pyrazole |
| 130 | 4-cyano-5-diacetylamino-1-(2,6-dichloro-4-trifluoromethylphenyl)pyrazole |
| 131 | 4-cyano-5-dibutyrylamino-1-(2,3,4-trichlorophenyl)pyrazole |
| 132 | 4-cyano-5-glutarimido-1-(2,3,4-trichlorophenyl)pyrazole |
| 133 | 4-cyano-5-dipentanoylamino-1-(2,3,4-trichlorophenyl)pyrazole |
| 134 | 4-cyano-5-di(3-methylbutyryl)amino-1-(2,3,4-trichlorophenyl)pyrazole |
| 135 | 5-(N—acetyl-N—propionyl)amino-4-cyano-1-(2,3,4-trichlorophenyl)pyrazole |
| 136 | 4-cyano-5-diheptanoylamino-1-(2,3,4-trichlorophenyl)pyrazole |
| 137 | 5-(N—acetyl-N—cyclopropylcarbonyl)amino-4-cyano-1-(2,3,4-trichlorophenyl)pyrazole |
| 138 | 5-(N—acetyl-N—2-ethylbutyryl)amino-4-cyano-1-(2,3,4-trichlorophenyl)pyrazole |
| 139 | 4-cyano-5-diisobutyrylamino-1-(2,3,4-trichlorophenyl)-pyrazole |
| 140 | 1-(2-chloro-4-isopropylphenyl)-4-cyano-5-diacetylamino-pyrazole |
| 141 | 5-(N—acetyl-N—heptanoyl)amino-4-cyano-1-(2,3,4-trichlorophenyl)pyrazole |
| 142 | 5-(N—acetyl-N—isobutyryl)amino-1-(2,3,4-trichlorophenyl)-4-cyanopyrazole |
| 143 | 1-(2-chloro-4-trifluoromethylphenyl)-4-cyano-5-dipropionylaminopyrazole |
| 144 | 4-cyano-1-(2,6-dichloro-4-trifluoromethylphenyl)-5-dipropionylaminopyrazole |
| 145 | 4-cyano-1-(2,6-dichloro-4-trifluoromethylphenyl)-5-succinimidopyrazole |
| 146 | 1-(2-chloro-4-trifluoromethylphenyl)-4-cyano-5-succinimidopyrazole |
| 147 | 4-cyano-1-(2,6-dichloro-4-trifluoromethylphenyl)-5-glutarimidopyrazole |
| 148 | 4-cyano-5-(N—isobutyryl-N—propionyl)amino-1-(2,3,4-trichlorophenyl)pyrazole |
| 149 | 5-(N—acetyl-N—propionyl)amino-1-(2-chloro-4-trifluoromethylphenyl)-4-cyanopyrazole |
| 150 | 4-cyano-5-diacetylamino-1-(2,4-dichloro-6-methylphenyl)-pyrazole |
| 151 | 5-(N—acetyl-N—pentanoyl)amino-4-cyano-1-(2,3,4-trichlorophenyl)pyrazole |
| 152 | 1-(4-n-butyl-2,3,5,6-tetrafluorophenyl)-4-cyano-5-diacetylaminopyrazole |
| 153 | 4-cyano-5-diacetylamino-1-pentafluorophenylpyrazole |
| 154 | 4-cyano-5-diacetylamino-1-(2,3,4,6-tetrafluorophenyl)-pyrazole |
| 155 | 5-(N—acetyl-N—methoxycarbonyl)amino-4-cyano-1-(2,3,4-trichlorophenyl)pyrazole |
| 156 | 1-(2-chloro-4-methylphenyl)-4-cyano-5-diacetylaminopyrazole |
| 157 | 4-cyano-5-methylsuccinimido-1-(2,3,4-trichlorophenyl)-pyrazole |
| 158 | 1-(2-chloro-4-trifluoromethylphenyl)-4-cyano-5-glutarimidopyrazole |
| 159 | 4-cyano-1-(2,6-dichloro-4-trifluoromethylphenyl)-5-di(phenoxycarbonyl)aminopyrazole |
| 160 | 5-acetamido-1-(2-bromo-4-trifluoromethylphenyl)-4-cyanopyrazole |
| 161 | 1-(2-chloro-4-methylphenyl)-5-(3-chlorobutyramido)-4-cyanopyrazole |
| 162 | 4-cyano-1-(2,6-dichloro-4-trifluoromethylphenyl)-5-(2-methylpentanamido)pyrazole |
| 163 | 1-(4-n-butyl-2,3,5,6-tetrafluorophenyl)-4-cyano-5-propionamidopyrazole |
| 164 | 4-cyano-1-(2,6-dichloro-4-trifluoromethylphenyl)-5-(2-ethyl-3-methylbutyramido)pyrazole |
| 165 | 1-(2-bromo-4-trifluoromethylphenyl)-4-cyano-5-diacetylaminopyrazole |
| 166 | 1-(2-chloro-4-trifluoromethylphenyl)-4-cyano-5-di(3-methylbutyryl)aminopyrazole |
| 167 | 1-(4-chloro-2,3,5,6-tetrafluorophenyl)-4-cyano-5-diacetylaminopyrazole |
| 168 | 4-cyano-5-(N—isobutyryl-N—methoxycarbonyl)amino-1-(2,3,4-trichlorophenyl)pyrazole |
| 169 | 4-cyano-5-diacetylamino-1-(2-nitro-4-trifluoromethylphenyl)pyrazole |
| 170 | 4-cyano-1-(2,6-dichloro-4-trifluoromethylphenyl)-5-(4-ethoxycarbonylbutyramido)pyrazole |
| 171 | 4-cyano-1-(4-methyl-2,3,6-trichlorophenyl)-5-propionamidopyrazole |
| 172 | 5-acetamido-1-[4-sec-butyl-2,3,5,6-tetrafluorophenyl]-4-cyanopyrazole |
| 173 | 5-acetamido-4-cyano-1-(2,3,5,6-tetrafluoro-4-vinylphenyl)-pyrazole |
| 174 | 1-[4-sec-butyl-2,3,5,6-tetrafluorophenyl]-4-cyano-5-diacetylaminopyrazole |
| 175 | 1-(2-chloro-4-n-propylphenyl)-4-cyano-5-propionamidopyrazole |
| 176 | 1-[4-sec-butyl-2,3,5,6-tetrafluorophenyl]-4-cyano-5-propionamidopyrazole |
| 177 | 4-cyano-1-(2,3-dichloro-4-methylphenyl)-5-propionamidopyrazole |
| 178 | 5-acetamido-4-cyano-1-(3,5-difluoro-2,4,6-trichlorophenyl)-pyrazole |
| 179 | 5-acetamido-1-(4-bromo-2,3,5,6-tetrafluorophenyl)-4- |

-continued

| No | Compound |
|---|---|
| | cyanopyrazole |
| 180 | 5-acetamido-4-cyano-1-(2,3-dichloro-4-methylphenyl)-pyrazole |
| 181 | 4-cyano-5-diacetylamino-1-(2,3,4,6-tetrachlorophenyl)pyrazole |
| 182 | 4-cyano-5-diacetylamino-1-(2,3-dichloro-4-methylphenyl)pyrazole |
| 183 | 4-cyano-5-di(3-methylbutyryl)amino-1-(2,3,5,6-tetrafluoro-4-trifluoromethyl)pyrazole |
| 184 | 1-(2-chloro-4-trifluoromethylphenyl)-4-cyano-5-(2-methylcyclopropylcarbonamido)pyrazole |
| 185 | 4-cyano-5-cyclopropylcarbonamido-1-(2,3,4,6-tetrachlorophenyl)pyrazole |
| 186 | 4-cyano-5-(2-methylcyclopropylcarbonamido)-1-(2,3,5,6-tetrafluoro-4-trifluoromethylphenyl)pyrazole |
| 187 | 4-cyano-1-(2,6-dichloro-4-trifluoromethylphenyl)-5-(2-methylcyclopropylcarbonamido)pyrazole |
| 188 | 4-cyano-5-(2,2-dimethylsuccinimido)-1-(2,3,4-trichlorophenyl)pyrazole |
| 189 | 4-cyano-1-(2,6-dichloro-4-trifluoromethylphenyl)-5-di-(3-methylbutyryl)aminopyrazole |

The numbers 1 to 189 are assigned to the above compounds for identification and reference hereafter; compounds hereinafter identified by numbers are as indicated above.

Particularly preferred compounds according to the present invention are, referring to the identification by numbers hereinbefore indicated, Compounds Nos. 1, 2, 3, 5 to 10, 13 to 18, 20, 22 to 25, 27 to 31, 36, 40 to 44, 47, 54, 55, 57 to 65, 67, 68, 69, 72, 73, 75, 76, 77, 87, 89, 93, 96 to 99, 104, 105, 109, 110, 112, 113, 116, 117, 120, 123, 126, 128, 130, 131, 133, 134, 135, 137, 138, 139, 142, 143, 144, 148, 149, 151, 155, 162, 166, 167, 168, 178, 181, 183 to 187 and 189.

In experiments on herbicidal activity carried out on representative compounds of general formula II, the following results have been obtained:

EXPERIMENT 1

Test Methods (a) Test Procedure (A)

The solutions of the test compounds were prepared by dissolving the test compounds in acetone. Application was from a standard laboratory herbicide sprayer using a flat fan jet travelling at 1.6 m.p.h. (2.6 km/hour) and delivering the equivalent of 530 liters of spray fluid per hectare, the spray pressure being 2.81 kg/cm$^2$ (40 pounds/inch$^2$). The solutions of the test compounds were prepared by dissolving 0.256 g of test compound in acetone and making up with more acetone to a volume of 34 ml, equivalent to an application rate of 4000 g of test compound per hectare. Solutions equivalent to application rates of 2000, 1000, 500, 250, 125, 63, 31, 16, 8 and 4 g/ha of test compound were then prepared by two-fold dilution with acetone.

Test Procedure (B)

The procedure described in Test Procedure (A) above was used except that a solution of test compound in acetone equivalent to an application rate of 2000 g/ha was prepared and solutions equivalent to application rates of 500, 125, 31 and 8 g/ha of test compounds were then prepared by four-fold serial dilution with acetone.

(b) Weed Control: Pre-emergence application

Weed seeds were sown on the surface of John Innes No. 1 potting compost (7 parts by volume of sterilized loam, 3 parts by volume of peat and 2 parts by volume of fine grit) in 9 cm diameter bitumenised paper pots. The quantities of seeds per pot were as follows:

| Weed species | Approximate number seeds/pot |
|---|---|
| (i) Broad leafed weeds | |
| *Sinapis arvensis* | 30–40 |
| *Polygonum lapathifolium* | 30–40 |
| *Stellaria media* | 30–40 |
| (ii) Grass weeds | |
| *Avena fatua* | 15–20 |
| *Alopecurus myosuroides* | 30–40 |
| *Echinochloa crus-galli* | 20–30 |

The test compounds were applied to the uncovered seeds as described above in Procedures (A) or (B) and the seeds were covered with 25 ml of sharp sand after spraying. A single pot of each weed species was allocated to each treatment, with unsprayed controls and controls sprayed with acetone alone. After treatment, the pots were kept in the greenhouse and were watered overhead.

Assessment Procedures

Assessment Procedure (i)

Visual assessment of weed control activity was made 19 to 28 days after spraying in comparison with unsprayed controls. The results were expressed as the minimum effective dose (MED) in kg/ha which gave 90% reduction in growth or kill of the weeds in comparison with plants in the control pots.

Assessment Procedure (ii)

Visual assessment of percentage weed destruction was made 19 to 28 days after spraying in comparison with unsprayed controls. The percentage weed destruction figures were then plotted against application rates on logarithmic-arithmetic paper to calculate the effective dose (ED$_{90}$) in kg/ha which produced 90% destruction of weeds.

The results obtained are presented below in Tables I and II.

(c) Weed Control: Post-emergence application

Weed species were grown and then transplanted at the seedling stage into John Innes No. 1 potting compost in 9 cm diameter bitumenised paper pots, except for *Avena fatua*, which was sown directly in the test pot and not transplanted. The plants were then grown in the greenhouse until ready for spraying with the test compounds. The number of plants per pot and the growth stage of the plant at spraying were as follows:

| Weed species | Number of plants/pot | Growth stages at spraying |
|---|---|---|
| (i) Broad leafed weeds | | |
| *Polygonum lapathifolium* | 5 | 1–1½ pairs of leaves |
| *Stellaria media* | 5 | 4–6 leaves |
| *Abutilon theophrasti* | 3 | 2 pairs of leaves |
| (ii) Grass weeds | | |
| *Avena fatua* | 10 | 1 leaf |
| *Alopecurus myosuroides* | 5 | 1½ leaves |
| *Echinochloa crus-galli* | 5 | 1–2 leaves |

The test compounds were applied to the plants as described above in Procedures (A) or (B). A single pot of each weed species was allocated to each treatment, with unsprayed controls and controls sprayed with acetone alone. After spraying, the pots were kept in the greenhouse and watered overhead, commencing 24 hours after spraying. Assessment of the control of the growth of the weeds was made 19 to 28 days after spraying by Assessment Procedure (i) or (ii) described in (b) above. The results obtained are presented below in Tables III and IV.

EXPERIMENT 2

Test Method

Test Procedure

The solutions of the test compounds were prepared by dissolving the test compounds in acetone. Application was from a standard laboratory herbicide sprayer using a flat fan jet travelling at 1.6 m.p.h. (2.6 km/hour) and delivering the equivalent of 530 liters of spray fluid per hectare, the spray pressure being 2.81 kg/cm$^2$ (40 pounds/inch$^2$). The solutions of the test compounds were prepared by dissolving 0.0755 g of test compound in acetone (20 ml), equivalent to an application rate of 2000 g of test compound per hectare. Solutions equivalent to application rates of 500, 125, 32, 8 and 2 g/ha test compound were then prepared by four-fold serial dilution with acetone.

(b) Weed Control: Pre-emergence application

Weeds seeds were sown on the surface of John Innes No. 1 potting compost (7 parts by volume of sterilized loam, 3 parts by volume of peat and 2 parts by volume of fine grit) in 7 cm-square plastic pots. The quantities of seeds per pot were as follows:

| Weed species | Approximate number of seeds/pot |
|---|---|
| (i) Broad leafed weeds | |
| Chenopodium album | 50 |
| Sinapis arvensis | 30–40 |
| Abutilon theophrasti | 15 |
| Ipomea purpurea | 8 |
| (ii) Grass weeds and sedges | |
| Avena fatua | 15–20 |
| Echinochloa crus-galli | 30 |
| Cyperus rotundus | 3 nuts |

The test compounds were applied as described above and the seeds were covered with 25 ml of sharp sand after spraying. A single pot of each weed species was allocated to each treatment, with unsprayed controls and controls sprayed with acetone alone. After treatment, the pots were kept in the greenhouse and watered overhead. Visual assessment of percentage weed destruction was made 21 days after spraying, in comparison with unsprayed controls. The percentage weed destruction figures were then plotted against application rates on logarithmic-arithmetic paper to calculate the effective dose (ED$_{90}$) which produced 90% destruction of weeds. The results obtained are presented below in Table V.

(c) Weed Control: Post-emergence application

Weed species were grown and then transplanted at the seedling stage into John Innes No. 1 potting compost in 7 cm-square plastic pots, except for Avena fatua, which was sown directly in the test pot and not transplanted. The plants were then grown in the greenhouse until ready for spraying with the test compounds. The number of plants per pot and the growth stage of the plant at spraying were as follows:

| Weed species | Number of plants/pot | Growth stage at spraying |
|---|---|---|
| (i) Broad leafed weeds | | |
| Chenopodium album | 4 | 4 leaves |
| Sinapis arvensis | 4 | 2 leaves |
| Abutilon theophrasti | 3 | 1–2 leaves |
| Ipomea purpurea | 3 | 2 leaves |
| (ii) Grass weeds and sedges | | |
| Avena fatua | 10 | 1–2 leaves |
| Echinochloa crus-galli | 4 | 1–2 leaves |
| Cyperus rotundus | 3 | 2–3 leaves |

The test compounds were applied as described above. A single pot of each weed species was allocated to each treatment, with unsprayed controls and controls sprayed with acetone alone. After spraying, the pots were kept in the greenhouse and watered overhead, commencing 24 hours after spraying. Visual assessment of percentage weed destruction in comparison with unsprayed controls was made 14 days after spraying. The ED$_{90}$ values were then calculated as described above. The results obtained are presented below in Table VI.

| KEY TO WEED SPECIES |
|---|
| (a) GRASS WEEDS AND SEDGES |
| Af = *Avena fatua* |
| Ec = *Echinochloa crus-galli* |
| Am = *Alopecurus myosuroides* |
| Cr = *Cyperus rotundus* |
| (b) BROAD LEAF WEEDS |
| Sm = *Stellaria media* |
| Pl = *Polygonum lapathifolium* |
| Sa = *Sinapis arvensis* |
| At = *Abutilon theophrasti* |
| Ca = *Chenopodium album* |
| Ip = *Ipomea purpurea* |

TABLE I

| Test Compound No. | Test Procedure | PRE-EMERGENCE MED (g/ha) [Assessment Procedure (i)] | | | | | | Application rates applied (g/ha) |
|---|---|---|---|---|---|---|---|---|
| | | Sm | Pl | Sa | Af | Ec | Am | |
| 1 | A | 250 | 63 | 63–125 | 125–250 | 125 | 250 | 16–1000 |
| 2 | A | 250 | 63–125 | 31–63 | 125–250 | 250 | 250 | 8–2000 |
| 3 | A | 500 | 31–63 | 125 | 125–250 | 125 | 125–250 | 4–2000 |
| 4 | A | NR | 2000 | 500 | 4000 | 2000 | >4000 | 500–4000 |
| 5 | A | 31 | 16 | 16–31 | 63 | 8–16 | 63 | 8–2000 |
| 6 | A | >2000 | 125 | 250 | 500–1000 | 125 | 500–1000 | 8–2000 |
| 7 | A | >>1000 | 125–250 | 125 | >>1000 | 250–500 | 1000 | 4–1000 |
| 8 | A | 1000 | 125–250 | 125–250 | >1000 | 250–500 | 1000 | 4–1000 |
| 9 | A | 16–31 | 31 | 8 | 63–125 | 31–63 | 63–125 | 4–1000 |
| 10 | A | 125–500 | 250 | 125 | 250–500 | 250–500 | 250–500 | 4–1000 |
| 11 | A | NR | 250 | 1000–2000 | >>2000 | 500–1000 | >>2000 | 16–2000 |
| 12 | B | 2000 | 125–250 | 31 | >2000 | >>2000 | 500–2000 | 8–2000 |
| 13 | B | >>2000 | 125–500 | 125 | >>2000 | 500–2000 | >>2000 | 8–2000 |
| 14 | A | 31–63 | 63 | 31 | 63–125 | 63 | 63–125 | 31–1000 |
| 15 | A | 125–250 | 63–125 | 16–31 | 250 | 31–63 | 63 | 4–2000 |

TABLE I-continued

| Test Compound No. | Test Procedure | PRE-EMERGENCE MED (g/ha) [Assessment Procedure (i)] | | | | | | Application rates applied (g/ha) |
|---|---|---|---|---|---|---|---|---|
| | | Sm | Pl | Sa | Af | Ec | Am | |
| 16 | A | 125 | 63 | 31–63 | 125–250 | 31–63 | 63–125 | 4–1000 |
| 17 | B | 500–2000 | 125–500 | 125–500 | >2000 | 500–2000 | >2000 | 8–2000 |
| 18 | B | 500–2000 | 125–500 | 31–125 | 500 | 125 | 500 | 8–2000 |
| 19 | B | 2000 | 125–500 | 31 | >2000 | 500–2000 | >>2000 | 8–2000 |
| 20 | B | >2000 | 500–2000 | 125–500 | 500–2000 | 500–2000 | 2000 | 8–2000 |
| 21 | A | NR | 500–1000 | 125–250 | >1000 | 500–1000 | >1000 | 4–1000 |
| 26 | B | 500 | 125–500 | 31–125 | 500–2000 | 125–500 | 2000 | 8–2000 |
| 31 | A | 31–63 | 63–125 | 63 | 63–125 | 63–125 | 63–125 | 4–1000 |
| 32 | B | 1000–2000 | 500–1000 | 500–1000 | 1000–2000 | 500–1000 | 2000 | 8–4000 |

TABLE II

| Test Compound No. | Test Procedure | PRE-EMERGENCE ED90 (g/ha) [Assessment Procedure (ii)] | | | | | | Application rates applied (g/ha) |
|---|---|---|---|---|---|---|---|---|
| | | Sm | Pl | Sa | Af | Ec | Am | |
| 22 | B | 1700 | 300 | 1000 | >2000 | 1000 | >>2000 | 8–2000 |
| 23 | B | 2000 | 125 | 1700 | 1900 | 1700 | 1900 | 8–2000 |
| 24 | B | 250 | 74 | 280 | 1400 | 125 | 380 | 8–2000 |
| 25 | B | 170 | 79 | 18 | 1500 | 250 | 500 | 8–2000 |
| 27 | B | 250 | 60 | 31 | 96 | 58 | 125 | 8–2000 |
| 28 | B | NR | 2000 | 2000 | NR | 2000 | NR | 8–2000 |
| 29 | B | 330 | 18 | 300 | 90 | 80 | 350 | 8–2000 |
| 30 | B | >2000 | 380 | 380 | 2000 | 310 | 1700 | 8–2000 |
| 33 | B | 1800 | 500 | 250 | >>2000 | 770 | >2000 | 8–2000 |

TABLE III

| Test Ccompound No. | Test Procedure | POST-EMERGENCE MED (g/ha) [Assessment Procedure (i)] | | | | | | | Application rates applied (g/ha) |
|---|---|---|---|---|---|---|---|---|---|
| | | Sm | Pl | At | Af | Ec | Am | Cr | |
| 1 | A | 63–125 | 16 | <16 | >>1000 | 1000 | >1000 | >>1000 | 16–1000 |
| 2 | A | 31–63 | 8–16 | 8 | 2000 | 1000–2000 | 1000–2000 | >>2000 | 8–2000 |
| 3 | A | 63–125 | 16 | <4 | 1000 | 125–250 | 1000 | >2000 | 4–2000 |
| 4 | A | NR | <500 | <500 | NR | NR | >4000 | NR | 500–4000 |
| 5 | A | 63–125 | 16 | <8 | 500 | 250–500 | 250–500 | 2000 | 8–2000 |
| 6 | A | NR | 63 | <8 | >>2000 | 500–1000 | 2000 | >>2000 | 8–2000 |
| 7 | A | >>1000 | 63–125 | 16 | >>1000 | 500–1000 | >>1000 | — | 4–1000 |
| 8 | A | >>1000 | 63–125 | 16 | >>1000 | 500–1000 | NR | — | 4–1000 |
| 9 | A | 8 | 4–8 | <4 | 250 | 125–250 | 250 | 1000 | 4–1000 |
| 10 | A | 16 | 8–16 | <4 | 1000 | 1000 | 1000 | >1000 | 4–1000 |
| 11 | A | NR | 63–125 | <16 | >>2000 | >2000 | >2000 | NR | 16–2000 |
| 12 | B | >>2000 | 31 | <8 | >>2000 | 500 | >>2000 | >>2000 | 8–2000 |
| 13 | B | >2000 | 125–500 | 8–31 | NR | 500 | >>2000 | NR | 8–2000 |
| 14 | A | 31–63 | <31 | 500 | 500 | 500 | 1000 | >1000 | 31–1000 |
| 15 | A | 63–125 | 8–16 | <4 | 2000 | 500–1000 | 500–1000 | <2000 | 4–2000 (2000 only for Cr) |
| 16 | A | 63–125 | 16–31 | <4 | 500–1000 | 500 | 500–1000 | >1000 | 4–1000 |
| 17 | B | 125–500 | 8 | <8 | >2000 | 500–2000 | >2000 | >>2000 | 8–2000 |
| 18 | B | 125 | 8 | <8 | 2000 | 125 | 2000 | >2000 | 8–2000 |
| 19 | B | >2000 | 8–31 | <8 | 2000 | 500 | >2000 | NR | 8–2000 |
| 20 | B | >2000 | 31–125 | <8 | >2000 | 500 | >>2000 | >>2000 | 8–2000 |
| 21 | A | NR | 125–250 | 8–16 | >>1000 | >>1000 | >>1000 | >>1000 | 4–1000 |
| 26 | B | 125–500 | 8–31 | <8 | >2000 | 500 | 2000 | >>2000 | 8–2000 |
| 31 | A | 16 | 8–16 | <4 | 1000 | 1000 | 1000 | >1000 | 4–1000 |
| 32 | B | 2000 | 250 | 125 | >>4000 | >4000 | NR | >>4000 | 8–4000 |

TABLE IV

| Test Compound No. | Test Procedure | POST-EMERGENCE ED90 (g/ha) [Assessment Procedure (ii)] | | | | | | | Application rates applied (g/ha) |
|---|---|---|---|---|---|---|---|---|---|
| | | Sm | Pl | At | Af | Ec | Am | Cr | |
| 22 | B | >>2000 | 58 | 31 | >>2000 | >2000 | >>2000 | NR | 8–2000 |
| 23 | B | >>2000 | 25 | 20 | >>2000 | 1600 | >>2000 | NR | 8–2000 |
| 24 | B | 74 | 8 | <8 | >>2000 | 1200 | 1200 | >>2000 | 8–2000 |
| 25 | B | 41 | <8 | <8 | >2000 | 1700 | 2000 | >>2000 | 8–2000 |
| 27 | B | 17 | <8 | <8 | 1100 | 200 | 500 | 2000 | 8–2000 |
| 28 | B | >>2000 | 16 | <8 | >>2000 | >2000 | >>2000 | >>2000 | 8–2000 |
| 29 | B | 12 | <8 | <8 | 94 | 16 | 58 | 2000 | 8–2000 |
| 30 | B | 1400 | 31 | <8 | >>2000 | 400 | 500 | 2000 | 8–2000 |
| 33 | B | 500 | 125 | 14 | >>2000 | >>2000 | >>2000 | NR | 8–2000 |

TABLE V

| Test Compound No. | PRE-EMERGENCE ED90 (g/ha) | | | | | | | Application rates applied (g/ha) |
| --- | --- | --- | --- | --- | --- | --- | --- | --- |
| | Ca | Sa | At | Ip | Af | Ec | Cr | |
| 34 | 8 | 70 | 18 | 1300 | 2000 | 125 | >2000 | 8–2000 |
| 35 | — | 60 | 60 | 500 | >2000 | 500 | >2000 | 8–2000 |
| 36 | 8 | 115 | 70 | 1100 | >>2000 | 240 | >>2000 | 8–2000 |
| 37 | — | 72 | 22 | 500 | >2000 | 460 | NR | 8–2000 |
| 38 | — | 400 | 31 | 500 | 2000 | 180 | 2000 | 8–2000 |
| 39 | — | 125 | 8 | 200 | 2000 | 125 | 1100 | 8–2000 |
| 40 | — | 8 | 8 | 27 | 32 | 27 | 125 | 2–500 |
| 41 | — | 300 | 420 | >2000 | 125 | 31 | 1250 | 8–2000 |
| 42 | — | 31 | 94 | 2000 | 125 | 27 | 500 | 8–2000 |
| 43 | — | 26 | 31 | 1100 | 105 | 20 | 125 | 8–2000 |
| 44 | — | 125 | 125 | 2000 | 240 | 115 | 125 | 8–2000 |
| 45 | — | 270 | 1050 | NR | >>2000 | 1100 | NR | 8–2000 |
| 46 | — | 500 | 390 | 1900 | 1450 | 480 | >>2000 | 8–2000 |
| 47 | — | 31 | 31 | 250 | 500 | 31 | 500 | 8–2000 |
| 48 | — | 74 | 60 | >2000 | 2000 | 300 | >>2000 | 8–2000 |
| 49 | — | 180 | 1000 | >2000 | >>2000 | 500 | >>2000 | 8–2000 |
| 50 | — | 1100 | 660 | >>2000 | >>2000 | 1000 | NR | 8–2000 |
| 51 | — | <8 | 31 | 500 | 220 | 125 | 260 | 8–2000 |
| 52 | — | 1700 | 2000 | >2000 | >>2000 | >2000 | >2000 | 8–2000 |
| 53 | — | 70 | 32 | 500 | 2000 | 500 | >>2000 | 8–2000 |
| 54 | — | 2 | 27 | 125 | 125 | 31 | 460 | 2–500 |
| 55 | — | 64 | 32 | 2000 | 160 | 125 | 500 | 8–2000 |
| 56 | — | 31 | 64 | 2000 | 500 | 125 | >2000 | 8–2000 |
| 57 | — | 120 | 44 | >500 | 125 | 66 | 500 | 2–500 |
| 58 | 125 | 29 | 8 | 32 | 125 | 120 | 480 | 2–500 |
| 59 | 125 | 240 | 31 | 1600 | 2000 | 500 | >>2000 | 8–2000 |
| 60 | 125 | 430 | 125 | 50 | >>2000 | 500 | >>2000 | 8–2000 |
| 61 | — | 27 | 8 | 27 | 125 | 29 | 125 | 2–500 |
| 62 | — | 17 | 8 | 56 | 125 | 31 | 125 | 2–500 |
| 63 | 2 | 93 | 32 | 420 | 125 | 120 | 500 | 2–500 |
| 64 | <2 | 7 | 7 | 100 | 32 | 30 | 125 | 2–500 |
| 65 | — | 31 | 125 | 125 | 125 | 86 | >125 | 2–125 |
| 66 | — | 110 | 125 | >>2000 | NR | 1700 | NR | 8–2000 |
| 67 | — | 120 | 120 | 1100 | 2000 | 220 | 500 | 8–2000 |
| 68 | — | 31 | 31 | 450 | >>2000 | 240 | 1200 | 8–2000 |
| 69 | — | 8 | 8 | 780 | 2000 | 500 | 500 | 8–2000 |
| 70 | — | <8 | 31 | 500 | 500 | 125 | >2000 | 8–2000 |
| 71 | — | 320 | 205 | 1600 | 2000 | 450 | >>2000 | 8–2000 |
| 72 | — | 32 | 29 | 110 | 125 | 120 | 430 | 8–2000 |
| 73 | — | <8 | <8 | 125 | 110 | 40 | 110 | 8–2000 |
| 74 | — | 1500 | 270 | >2000 | 860 | 320 | 500 | 8–2000 |
| 75 | — | 110 | 100 | 720 | 840 | 180 | 840 | 8–2000 |
| 76 | — | 100 | 31 | 500 | 500 | 160 | 500 | 8–2000 |
| 77 | — | 6 | 6 | 82 | 94 | 31 | 107 | 2–500 |
| 78 | 400 | 125 | <8 | 500 | >>2000 | 900 | >2000 | 8–2000 |
| 79 | — | 70 | 18 | 240 | 240 | 62 | 2000 | 8–2000 |
| 80 | — | 400 | 180 | 1800 | 2000 | 1900 | NR | 8–2000 |
| 81 | 32 | 500 | 100 | 900 | 1700 | 480 | 2000 | 8–2000 |
| 82 | — | 115 | 31 | 2000 | 2000 | 500 | 500 | 8–2000 |
| 83 | — | 250 | 250 | 500 | 1800 | 500 | 500 | 8–2000 |
| 84 | — | 210 | 32 | >2000 | >>2000 | >2000 | NR | 8–2000 |
| 85 | 240 | 50 | 32 | 62 | 500 | 400 | >500 | 2–500 |
| 86 | <2 | 11 | 32 | 125 | 500 | 500 | NR | 2–500 |
| 87 | 32 | 60 | 28 | 420 | 125 | 120 | 500 | 2–500 |
| 88 | — | 500 | 400 | 500 | 500 | 470 | 2000 | 8–2000 |
| 89 | — | 120 | 260 | >>500 | 125 | 125 | >>500 | 2–500 |
| 90 | — | 1900 | 500 | >>2000 | >>2000 | 2000 | >>2000 | 8–2000 |
| 91 | — | 1000 | 32 | >>2000 | >>2000 | 1800 | >>2000 | 8–2000 |
| 92 | — | 120 | 110 | >>500 | >>500 | >>500 | >>500 | 2–500 |
| 93 | — | 8 | 7 | 66 | 100 | 31 | 125 | 2–500 |
| 94 | — | 430 | 220 | 2000 | >2000 | 1800 | 1800 | 8–2000 |
| 95 | — | 500 | 120 | >>500 | >>500 | 500 | >>500 | 2–500 |
| 96 | — | 125 | 32 | >500 | >>500 | >>500 | NR | 2–500 |
| 97 | 32 | 110 | 32 | 58 | 125 | 110 | 125 | 8–2000 |
| 98 | — | 10 | 12 | 32 | 70 | 70 | — | 2–500 |
| 99 | — | 8 | 8 | 125 | 110 | 50 | — | 2–500 |
| 100 | 16 | 8 | 31 | 125 | 125 | 240 | >500 | 2–500 |
| 101 | <8 | <8 | <8 | >2000 | 2000 | >2000 | NR | 8–2000 |
| 102 | 125 | 16 | 8 | 125 | 450 | 450 | >500 | 2–500 |
| 103 | 100 | 8 | 32 | 430 | >>500 | 500 | NR | 2–500 |
| 104 | 8 | 7 | 7 | 32 | 32 | 29 | 125 | 2–500 |
| 105 | 13 | 8 | 7 | 55 | 31 | 31 | 32 | 2–500 |
| 106 | 8 | 120 | 110 | 500 | >500 | 190 | — | 2–500 |
| 107 | 31 | 120 | 29 | 125 | 125 | 125 | — | 2–500 |
| 108 | 8 | 58 | 31 | 390 | 500 | 500 | — | 2–500 |
| 109 | 58 | 12 | 5 | 58 | 125 | 110 | — | 2–500 |
| 110 | 31 | 54 | 15 | 100 | 125 | 240 | — | 2–500 |
| 111 | 47 | 32 | 27 | 125 | 125 | 120 | 500 | 2–500 |
| 112 | 8 | 12 | 8 | 56 | 56 | 62 | 170 | 2–500 |

TABLE V-continued

| Test Compound No. | PRE-EMERGENCE ED90 (g/ha) | | | | | | | Application rates applied (g/ha) |
|---|---|---|---|---|---|---|---|---|
| | Ca | Sa | At | Ip | Af | Ec | Cr | |
| 113 | <8 | 8 | 32 | 900 | 125 | 490 | 2000 | 8–2000 |
| 114 | <8 | 500 | 125 | 2000 | 2000 | 1100 | >>2000 | 8–2000 |
| 115 | <8 | 32 | 32 | 2000 | 500 | 490 | 2000 | 8–2000 |
| 116 | <2 | 125 | 32 | 210 | 160 | 450 | 500 | 2–500 |
| 117 | <2 | 8 | 45 | 210 | 62 | 120 | 210 | 2–500 |
| 118 | 8 | 500 | 2000 | 2000 | 125 | 500 | 800 | 8–2000 |
| 119 | 2 | 30 | 8 | 62 | 32 | 32 | 120 | 2–500 |
| 120 | 2 | 70 | 50 | >500 | >500 | 500 | >>500 | 2–500 |
| 121 | 2 | 8 | 8 | 70 | 68 | 32 | 125 | 2–500 |
| 122 | 32 | 500 | 42 | 640 | 640 | 280 | 2000 | 8–2000 |
| 123 | <2 | 30 | 8 | 68 | 46 | 30 | 125 | 2–500 |
| 129 | — | 32 | 125 | >>500 | 230 | >>500 | NR | 2–500 |
| 130 | — | 32 | 14 | 18 | 125 | 125 | 500 | 2–500 |
| 131 | — | 31 | 32 | 500 | 470 | 120 | 2000 | 8–2000 |
| 132 | — | 115 | >500 | >500 | NR | 500 | NR | 2–500 |
| 133 | — | 430 | 120 | 2000 | 1900 | 490 | >2000 | 8–2000 |
| 134 | <8 | <8 | <8 | 1800 | 500 | 440 | 2000 | 8–2000 |
| 135 | — | 31 | 8 | 110 | 110 | 110 | — | 2–500 |
| 136 | — | 450 | 500 | >>500 | 340 | >500 | — | 2–500 |
| 137 | <8 | <8 | 30 | 110 | 120 | 170 | >2000 | 8–2000 |
| 138 | <8 | 14 | 29 | 260 | 230 | 170 | >2000 | 8–2000 |
| 139 | 8 | 8 | 14 | 125 | 430 | 220 | 500 | 8–2000 |
| 140 | <8 | <8 | <8 | 500 | >2000 | 160 | NR | 8–2000 |
| 141 | <8 | 32 | 58 | 270 | 1700 | 500 | 2000 | 8–2000 |
| 142 | <8 | <8 | <8 | 125 | 490 | 125 | 1900 | 8–2000 |
| 143 | 31 | 12 | 2 | 125 | 120 | 110 | — | 2–500 |
| 144 | 2 | <2 | 5 | 125 | 120 | 110 | >500 | 2–500 |
| 145 | 2 | 8 | 125 | 125 | 110 | >500 | >>500 | 2–500 |
| 146 | 8 | 32 | 500 | 160 | 500 | >>500 | >500 | 2–500 |
| 147 | 8 | 220 | 1000 | 2000 | 125 | >>2000 | NR | 8–2000 |
| 148 | <2 | 29 | 18 | 70 | 230 | 70 | 300 | 2–500 |
| 149 | <2 | 8 | 2 | 70 | 125 | 70 | 120 | 2–500 |
| 150 | 8 | 500 | 120 | 500 | 500 | 1800 | NR | 8–2000 |
| 151 | <2 | 300 | 58 | 500 | 500 | 480 | >500 | 2–500 |
| 152 | 8 | 210 | 125 | >>2000 | >>2000 | 2000 | >>2000 | 8–2000 |
| 153 | 120 | 2000 | 280 | >2000 | 2000 | 500 | 2000 | 8–2000 |
| 154 | 8 | 840 | 490 | 640 | 640 | 490 | 2000 | 8–2000 |

TABLE VI

| Test Compound No. | POST-EMERGENCE ED90 (g/ha) | | | | | | | Application rates applied (g/ha) |
|---|---|---|---|---|---|---|---|---|
| | Ca | Sa | At | Ip | Af | Ec | Cr | |
| 34 | 8 | 54 | 8 | 270 | >2000 | >2000 | >2000 | 8–2000 |
| 35 | <8 | 8 | <8 | 300 | >>2000 | 2000 | >>2000 | 8–2000 |
| 36 | <8 | 410 | <8 | 27 | >>2000 | 500 | >>2000 | 8–2000 |
| 37 | 90 | 500 | 8 | 30 | >>2000 | 1100 | >>2000 | 8–2000 |
| 38 | 31 | 1200 | <8 | 2000 | >>2000 | 900 | >2000 | 8–2000 |
| 39 | 15 | 270 | <8 | <8 | >2000 | 470 | 2000 | 8–2000 |
| 40 | 2 | 8 | <2 | 8 | 25 | 110 | 500 | 2–500 |
| 41 | 16 | 330 | <8 | 31 | 125 | 270 | >2000 | 8–2000 |
| 42 | 89 | 115 | 22 | 1600 | 500 | 125 | 460 | 8–2000 |
| 43 | 80 | 76 | <8 | 1500 | 125 | 76 | 1700 | 8–2000 |
| 44 | <8 | 18 | <8 | 18 | 240 | 80 | 2000 | 8–2000 |
| 45 | 500 | 2000 | <8 | 1000 | NR | >>2000 | NR | 8–2000 |
| 46 | 31 | 410 | 18 | 125 | >>2000 | >>2000 | >>2000 | 8–2000 |
| 47 | <8 | 31 | <8 | 31 | 1300 | 500 | 2000 | 8–2000 |
| 48 | 125 | 245 | 14 | 840 | >>2000 | >2000 | NR | 8–2000 |
| 49 | 70 | 500 | 23 | 500 | >>2000 | >2000 | NR | 8–2000 |
| 50 | 54 | 500 | 15 | 500 | >>2000 | >>2000 | NR | 8–2000 |
| 51 | <8 | 125 | <8 | 31 | 2000 | 500 | >>2000 | 8–2000 |
| 52 | 8 | 460 | <8 | 1700 | >>2000 | >2000 | NR | 8–2000 |
| 53 | 8 | 125 | <8 | 110 | NR | >2000 | NR | 8–2000 |
| 54 | 2 | 95 | 6 | 15 | 500 | 125 | >>500 | 2–500 |
| 55 | <8 | 60 | <8 | 27 | 1600 | 125 | 2000 | 8–2000 |
| 56 | 32 | 310 | 32 | 24 | 500 | 125 | 2000 | 8–2000 |
| 57 | 8 | 260 | 7 | 110 | >500 | 120 | >500 | 2–500 |
| 58 | 29 | 125 | 2 | 2 | >500 | 230 | >>500 | 2–500 |
| 59 | <8 | 2000 | <8 | 32 | >2000 | 2000 | NR | 8–2000 |
| 60 | 31 | 1700 | 28 | 31 | 2000 | 1600 | NR | 8–2000 |
| 61 | <2 | 74 | 2 | 6 | 125 | 74 | 500 | 2–500 |
| 62 | 2 | 110 | <2 | 8 | 125 | 120 | 500 | 2–500 |
| 63 | 2 | 125 | 6 | 3 | 500 | 450 | >500 | 2–500 |
| 64 | <2 | 32 | <2 | 7 | 125 | 60 | 500 | 2–500 |
| 65 | 8 | 125 | 2 | 7 | >>125 | 86 | NR | 2–125 |
| 66 | 1650 | 1450 | 23 | >2000 | >>2000 | >>2000 | NR | 8–2000 |
| 67 | <8 | 125 | <8 | 8 | >2000 | 500 | 2000 | 8–2000 |

TABLE VI-continued

| Test Compound No. | Ca | Sa | At | Ip | Af | Ec | Cr | Application rates applied (g/ha) |
|---|---|---|---|---|---|---|---|---|
| 68 | 31 | 300 | <8 | 82 | >>2000 | 1800 | 2000 | 8-2000 |
| 69 | 95 | 125 | <8 | 27 | >>2000 | 250 | 2000 | 8-2000 |
| 70 | 15 | 1600 | <8 | 47 | >2000 | >2000 | >>2000 | 8-2000 |
| 71 | 125 | 450 | 31 | 500 | >2000 | 2000 | >>2000 | 8-2000 |
| 72 | 20 | 64 | 8 | 27 | 500 | 125 | 900 | 8-2000 |
| 73 | <8 | 32 | <8 | <8 | 125 | 125 | 500 | 8-2000 |
| 74 | 78 | 2000 | 125 | 1900 | 2000 | 1450 | >2000 | 8-2000 |
| 75 | 31 | 460 | <8 | 120 | >>2000 | 480 | >2000 | 8-2000 |
| 76 | 125 | 125 | <8 | 400 | 1100 | 450 | >>2000 | 8-2000 |
| 77 | 2 | 48 | 2 | 26 | 125 | 85 | 500 | 2-500 |
| 78 | 125 | 90 | 68 | 125 | >2000 | 2000 | >>2000 | 8-2000 |
| 79 | 56 | 500 | 8 | 210 | 1200 | 500 | >2000 | 8-2000 |
| 80 | 125 | 32 | 70 | 500 | >>2000 | >>2000 | NR | 8-2000 |
| 81 | 340 | 2000 | 8 | 125 | >>2000 | 1800 | >>2000 | 8-2000 |
| 82 | 31 | 2000 | <8 | 500 | >>2000 | 2000 | NR | 8-2000 |
| 83 | 31 | 500 | 125 | 125 | >>2000 | 2000 | NR | 8-2000 |
| 84 | 125 | 1500 | 32 | 1400 | >>2000 | 2000 | NR | 8-2000 |
| 85 | 14 | 100 | 8 | 17 | >>500 | 500 | >>500 | 2-500 |
| 86 | 27 | 125 | 8 | 27 | >500 | 500 | >>500 | 2-500 |
| 87 | 8 | 100 | 7 | 32 | 500 | 500 | >>500 | 2-500 |
| 88 | <8 | 2000 | <8 | 125 | >2000 | 500 | >>2000 | 8-2000 |
| 89 | 20 | 370 | 32 | >500 | 500 | 125 | >>500 | 2-500 |
| 90 | 125 | 1600 | 32 | 1600 | >>2000 | >>2000 | NR | 8-2000 |
| 91 | 2000 | >2000 | 8 | >>2000 | >>2000 | 2000 | >>2000 | 8-2000 |
| 92 | 92 | 32 | 32 | 500 | >>500 | >>500 | NR | 2-500 |
| 93 | 2 | 12 | <2 | 22 | 125 | 32 | 450 | 2-500 |
| 94 | 460 | 190 | 25 | 420 | >>2000 | >2000 | NR | 8-2000 |
| 95 | 32 | 370 | 27 | 125 | >>500 | >>500 | NR | 2-500 |
| 96 | 125 | >500 | 32 | 500 | NR | NR | NR | 2-500 |
| 97 | 125 | 380 | <8 | 125 | 500 | D 420 | 2000 | 8-2000 |
| 98 | 2 | 2 | <2 | 2 | 230 | 110 | 230 | 2-500 |
| 99 | 6 | 8 | 6 | 6 | 500 | 125 | >500 | 2-500 |
| 100 | 26 | 66 | 2 | 60 | >500 | 450 | >>500 | 2-500 |
| 101 | 2000 | 170 | <8 | 500 | >>2000 | >>2000 | NR | 8-2000 |
| 102 | 8 | 8 | 6 | 8 | 500 | 125 | >500 | 2-500 |
| 103 | 27 | 8 | 32 | 32 | >500 | 230 | >>500 | 2-500 |
| 104 | 7 | 13 | <2 | 8 | 62 | 100 | 500 | 2-500 |
| 105 | 8 | 8 | 2 | <2 | 125 | 125 | 125 | 2-500 |
| 106 | 8 | 60 | 8 | 32 | >>500 | >>500 | >>500 | 2-500 |
| 107 | 26 | 125 | 7 | 26 | >500 | >>500 | >>500 | 2-500 |
| 108 | 15 | 47 | <2 | 8 | >>500 | >>500 | >>500 | 2-500 |
| 109 | 8 | 32 | <2 | <2 | 125 | 110 | 500 | 2-500 |
| 110 | 12 | 125 | 6 | <2 | 500 | >500 | >>500 | 2-500 |
| 111 | 15 | 32 | 8 | 68 | >500 | >500 | >>500 | 2-500 |
| 112 | 8 | 15 | 2 | 8 | 500 | 230 | >500 | 2-500 |
| 113 | 60 | 125 | 70 | 100 | >>2000 | >2000 | >>2000 | 8-2000 |
| 114 | 900 | 2000 | 125 | 180 | >>2000 | >>2000 | >>2000 | 8-2000 |
| 115 | 500 | >2000 | 32 | 2000 | >2000 | 2000 | NR | 8-2000 |
| 116 | 125 | 125 | 32 | 160 | >500 | >500 | >>500 | 2-500 |
| 117 | 12 | 56 | 14 | 125 | 500 | 260 | >500 | 2-500 |
| 118 | 500 | 900 | 2000 | 110 | 500 | 500 | 1100 | 8-2000 |
| 119 | 8 | 45 | 6 | 7 | 125 | 210 | >500 | 2-500 |
| 120 | 125 | 210 | 42 | 125 | >>500 | NR | NR | 2-500 |
| 121 | 68 | 53 | 8 | 110 | 500 | 120 | >500 | 2-500 |
| 122 | 125 | 260 | 32 | 110 | 2000 | 2000 | >>2000 | 8-2000 |
| 123 | 8 | 17 | 2 | 8 | 500 | 440 | >500 | 2-500 |
| 129 | 125 | 2 | 8 | 125 | >500 | >>500 | >500 | 2-500 |
| 130 | 8 | 125 | 2 | 27 | 400 | 110 | >500 | 2-500 |
| 131 | 8 | 32 | <8 | 32 | 750 | 125 | >>2000 | 8-2000 |
| 132 | 500 | 32 | 24 | 125 | >>500 | >>500 | NR | 2-500 |
| 133 | 125 | 280 | 8 | 800 | >>2000 | 1200 | >>2000 | 8-2000 |
| 134 | <8 | 500 | < | <8 | >2000 | >>2000 | NR | 8-2000 |
| 135 | 6 | 100 | 125 | 125 | >500 | 380 | >500 | 2-500 |
| 136 | 125 | 32 | 8 | 500 | >>500 | >>500 | NR | 2-500 |
| 137 | 8 | 30 | <8 | <8 | 500 | 110 | >2000 | 8-2000 |
| 138 | <8 | 32 | <8 | 40 | 2000 | 450 | >2000 | 8-2000 |
| 139 | 8 | 65 | <8 | 25 | 500 | 240 | >2000 | 8-2000 |
| 140 | 125 | 240 | 14 | 32 | >>2000 | >2000 | NR | 8-2000 |
| 141 | 8 | 240 | 32 | 30 | >2000 | >2000 | >>2000 | 8-2000 |
| 142 | <8 | 70 | <8 | 32 | 2000 | 740 | >2000 | 8-2000 |
| 143 | 7 | 50 | 7 | 12 | 300 | 125 | 500 | 2-500 |
| 144 | 2 | 25 | 5 | 6 | 125 | 110 | 125 | 2-500 |
| 145 | 125 | 8 | 12 | 7 | >500 | >500 | >>500 | 2-500 |
| 146 | 16 | 8 | 14 | 18 | 125 | NR | >>500 | 2-500 |
| 147 | 500 | 32 | 30 | 500 | 2000 | >>2000 | NR | 8-2000 |
| 148 | 8 | 32 | 7 | 12 | >500 | 330 | >>500 | 2-500 |
| 149 | 8 | 53 | 2 | 60 | 230 | 160 | >500 | 2-500 |
| 150 | 500 | >2000 | 32 | 420 | >>2000 | 2000 | NR | 8-2000 |
| 151 | 32 | 430 | 6 | 8 | 460 | NR | >>500 | 2-500 |

TABLE VI-continued

| Test Compound No. | POST-EMERGENCE ED90 (g/ha) | | | | | | | Application rates applied (g/ha) |
|---|---|---|---|---|---|---|---|---|
| | Ca | Sa | At | Ip | Af | Ec | Cr | |
| 152 | 125 | 840 | 500 | >2000 | >>2000 | NR | NR | 8–2000 |
| 153 | 280 | >>2000 | 500 | 640 | 2000 | 1000 | >>2000 | 8–2000 |
| 154 | 500 | >2000 | 240 | 110 | 1800 | 1800 | NR | 8–2000 |

The following symbols which appear in the above Tables have the following meanings:

">>" means much greater than
">" means greater than
"<" means less than
"NR" means no reduction at any dose rate applied
"-" means not tested According to a feature of the present invention, there is provided a method for controlling the growth of weeds (i.e. undesired vegetation) at a locus which comprises applying to the locus a herbicidally effective amount of at least one N-phenylpyrazole derivative of general formula II. For this purpose, the N-phenylpyrazole derivatives are normally used in the form of herbicidal compositions (i.e. in association with compatible diluents or carriers suitable for use in herbicidal compositions), for example as hereinafter described.

The compounds of general formula II show herbicidal activity against dicotyledonous (i.e. broad-leafed) and monocotyledonous (e.g. grass) weeds by pre- and-/or, post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula II may be used to control the growth of broad-leafed weeds, for example, Aethusa cynapium, Abutilon theophrasti, Amaranthus retroflexus, Amsinckia intermedia, Anagallis arvensis, Anthemis arvensis, Atriplex patula, Bidens pilosa, Brassica nigra, Capsella bursa-pastoris, Chenopodium album, Chrysanthemum segetum, Cirsium arvense, Datura stramonium, Desmodium tortuosum, Emex australis, Euphorbia helioscopia, Fumaria officinalis, Galeopsis tetrahit, galium aparine, Geranium dissectum, Ipomea purpurea, Lamium pupureum, lapsana communis, Matricaria inodora, Monochoria vaginalis, Papaver rhoeas, Physalis longifolia, Plantago lanceolata, Polygonum spp., (e.g. Polygonum lapathifolium, Polygonum aviculare, Polygonum convolvulus and Polygonum persicaria), Portulaca oleracea, Raphanus raphanistrum, Rotala indica, Rumex obtusifolius, Saponaria vaccaria, Scandix pectenveneris Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis and Xanthium strumarium, and grass weeds, for example, Alopercurus myosuroides, Apera spica-venti, Agrostis stolonifera, Avena fatua, Avena ludoviciana, Brachiaria spp., Bromus sterilis, Bromus tectorum, Cenchrus spp., Cynodon dactylon, Digitaria sanquinalis, Echinochloa crusgalli, Eleusine indica, Setaria viridis and Sorghum halepense and sedges, for example Cyperus esculentus, Cyperus iria and Cyperus rotundus, and Eleocharis acicularis.

The amounts of compounds of general formula II applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 10 kg of active material per hectare give good results. However, it is to be understood that higher or lower application rates may be used, depending upon the particular problem of weed control encountered.

The compounds of general formula II may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates between 0.01 kg and 4.0 kg, and preferably between 0.01 kg and 2.0 kg, of active material per hectare are particularly suitable. More particularly, the compounds of general formula II may be used to control selectively the growth of broad leafed weeds, for example to control the growth of those broad leafed species hereinbefore mentioned, by pre, or more especially, post-emergence application in a non-directional fashion, e.g. by non-directional spraying, to an area used for growing cereal crops, e.g. wheat, barley, oats, maize and rice before or after emergence of both the crop and weeds and to control selectively the growth of broad-leafed and grass weeds, for example to control the growth of those broad-leafed weed species hereinbefore mentioned, by pre-emergence application in a non-directional fashion, e.g. by non-directional spraying, to an area to be used for growing soya beans or cotton before the emergence of both the crop and weeds.

For these purposes, i.e. the selective control of broad-leafed weeds by pre- or post-emergence application to an area used for growing cereal crops or by pre-emergence application to an area to be used for growing soya beans or cotton, application rates between 0.01 and 4.0 kg, and preferably between 0.01 kg and 2.0 kg, of active material per hectare are particularly suitable.

The compounds of general formula II may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 10.0 kg, and preferably between 1.0 kg and 4.0 kg, of active material per hectare.

The compounds of general formula II may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g. by directional or non-directional spraying) at application rates between 2.0 kg and 10.0 kg, and preferably between 4.0 and 10.0 kg, of active material per hectare are particularly suitable for this purpose.

When used to control the growth of weeds by pre-emergence application, the compounds of general formula II may be incorporated into the soil in which the weeds are expected to emerge. It will be appreciated that when the compounds of general formula II are used to control the growth of weeds by post-emergence application, i.e. by application to the aerial or exposed portions of emerged weeds, the compounds of general formula II will also normally come into contact with the soil and may also then exercise a pre-emergence control on later-germinating weeds in the soil.

Where especially prolonged weed control is required, the application of the compounds of general formula II may be repeated if required.

According to a further feature of the present invention, there are provided compositions suitable for herbicidal use comprising one or more of the N-phenylpyrazole derivatives of general formula II in association with, and preferably homogeneously dispersed in, one or more compatible herbicidally-acceptable diluents or carriers (i.e. diluents or carriers of the type generally accepted in the art as being suitable for use in herbicidal compositions and which are compatible with compounds of general formula II). The term "homogeneously dispersed" is used to include compositions in which the compounds of general formula II are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula II.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates.

Suitably, herbicidal compositions according to the present invention may comprise from 0.05% to 10% of surface-active agent but, if desired, herbicidal compositions according to the present invention may comprise higher proportions of surface-active agent, for example up to 15% in liquid emulsifiable suspension concentrates and up to 25% in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula II with solid diluents or by impregnating the solid diluents or carriers with solutions of the compounds of general formula II in volatile solvents, evaporating the solvents and, if necessary, grinding the products so as to obtain powders. Granular formulations may be prepared by absorbing the compounds of general formula II (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agent (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula II may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of one or more compounds of general formula II, from 2 to 10% w/v of surface-active agent, from 0.1 to 5% w/v of thickener and from 15 to 87.9% by volume of water; wettable powders which comprise from 10 to 90% w/w of one or more compounds of general formula II, from 2 to 10% w/w of surface-active agent and from 10 to 88% w/w of solid diluent or carrier; liquid water soluble concentrates which comprise from 10 to 30% w/v of one or more compounds of general formula II, from 5 to 25% w/v of surface-active agent and from 45 to 85% by volume of water-miscible solvent, e.g. dimethylformamide; liquid emulsifiable suspension concentrates which comprise from 10 to 70% w/v of one or more compounds of general formula II, from 5 to 15% w/v of surface-active agent, from 0.1 to 5% w/v of thickener and from 10 to 84.9% by volume of organic solvent; granules which comprise from 2 to 10% w/w of one or more compounds of general formula II, from 0.5 to 2% w/w of surface active agent and from 88 to 97.5% w/w of granular carrier, and emulsifiable concentrates which comprise from 0.05 to 90% w/v, and preferably from 1 to 60% w/v, of one or more compounds of general formula II, from 0.01 to 10% w/v, and preferably from 1 to 10% w/v, of surface-active agent and from 9.99 to 99.4%, and preferably from 39 to 98.99%, by volume of organic solvent.

Herbicidal compositions according to the present invention may also comprise the compounds of general formula II in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor[α-chloro-2,6-diethyl-N-(methoxymethyl)acetanilide], asulam[methyl(4-aminobenzenesulphonyl)-carbamate], alloxydim Na[sodium salt of 2-(1-allyloxyiminobutylidene)-5,5-dimethyl-4-methoxycarbonylcyclohexane-1,3-dione], atrazine[2-chloro-4-ethylamino-6-isopropylamino-1,3,5-triazine], barban[4-chlorobut-2-ynyl N-(3-chlorophenyl)carbamate], benzoylprop-ethyl[ethyl N-benzoyl-N-(3,4-dichlorophenyl)-2-aminopropionate], bromoxynil[3,5-dibromo-4-hydroxybenzonitrile], butachlor[N-(butoxymethyl)-α-chloro-2,6-diethylacetanilide], butylate[S-ethyl N,N-diisobutyl(thiocarbamate)], carbetamide[D-N-ethyl-2-(phenylcarbamoyloxy)propionamide], chlorfenprop-methyl[methyl 2-chloro-3-(4-chlorophenyl)propionate], chlorpropham[isopropyl N-(3-chlorophenyl)carbamate], chlortoluron[N'-(3-chloro-4-methylphenyl)-N,N-dimethylurea], cyanazine[2-chloro-4-(1-cyano-1-methylethylamino)-6-ethylamino-1,3,5-triazine], cycloate[N'-cyclohexyl-N-ethyl-S-ethyl(thiocarbamate)], 2,4-D[2,4-dichlorophenoxyacetic acid], dalapon[2,2-dichloropropionic acid], 2,4-DB[4-(2,4-dichlorophenoxy)butyric acid], desmedipham[3-(ethoxycarbonylamino)phenyl N-phenyl-carbamate], diallate[S-2,3-dichloroallyl-N,N-di-isopropyl(thiocarbamate)], dicamba[3,6-dichloro-2-methoxybenzoic acid], dichlorprop[(±)-2-(2,4-dichlorophenoxy)propionic acid], difenzoquat[1,2-dimethyl-3,5-diphenyl-pyrazolium salts], dimefuron{4-[2-chloro-4-(3,3-dimethylureido)-phenyl]-2-t-butyl-1,3,4-oxadiazolin-5-one}, dinitramine[N¹,N¹-diethyl-2,6-dinitro-4-trifluoromethyl-m-phenylenediamine], diuron[N'-(3,4-dichlorophenyl)-N,N-dimethylurea], EPTC[S-ethyl N,N-dipropyl(thiocarbamate)], ethofumesate[2-ethoxy-2,3-dihydro-3,3-dimethylbenzofuran-5-yl methylsulphonate], flamprop-isopropyl[isopropyl(±)-2-(N-benzoyl-3-chloro-4-fluoroanilino)propionate], flampropmethyl[methyl(±)-2-N-benzoyl-3-chloro-4-fluoroanilino)-propionate], fluometuron[N'-(3-trifluoromethylphenyl)-N,N-dimethylurea], ioxynil[4-hydroxy-3,5-di-iodobenzonitrile], isoproturon[N'-(4-isopropylphenyl)-N,N-dimethylurea], linuron[N-(3,4-dichlorophenyl)-N-methoxy-N-methylurea], MCPA[4-chloro-2-methylphenoxyacetic acid], MCPB[4-(4-chloro-2-methylphenoxy)-butyric acid], mecoprop[(±)-2-(4-chloro-2-methylphenoxy)propionic acid], metamitron[4-amino-3-methyl-6-phenyl-1,2,4-triazin-5(4H)-one], methabenzthiazuron[N-(benzothiazol-2-yl)-N,N'-dimethylurea], metribuzin[4-amino-6-t-butyl-3-(methylthio)-1,2,4-triazin-5(4H)-one], molinate[S-ethyl N,N-hexamethylene(-thiocarbamate)], oxadiazon[3-(2,4-dichloro-5-isopropoxyphenyl)-5-t-butyl-1,3,4-oxadiazolin-2-one], paraquat[1,1'-dimethyl-4,4'-bipyridylium salts], pebulate[S-propyl N-butyl-N-ethyl(thiocarbamate)], phenmedipham[3-(methoxycarbonylamino)phenyl N-(3-methylphenyl)carbamate], prometryne[4,6-bisisopropylamino-2-methylthio-1,3,5-triazine], propachlor[α-chloro-N-isopropylacetanilide], propanil[N-(3,4-dichlorophenyl)propionamide], propham[isopropyl N-phenylcarbamate], pyrazone[5-amino-4-chloro-2-phenylpyridazin-3(2H)-one], simazine[2-chloro-4,6-bisethylamino-1,3,5-triazine], TCA (trichloroacetic acid), thiobencarb[S-(4-chlorobenzyl)-N,N-diethylthiolcarbamate], tri-allate[S-2,3,3-trichloroallyl N,N-di-isopropyl(thiocarbamate)] and trifluralin[2,6-dinitro-N,N-dipropyl-4-trifluoromethylaniline]; insecticides, e.g. carbaryl[naphth-1-yl N-methylcarbamate]; synthetic pyrethroids e.g. permethrin and cypermethrin; and fungicides, e.g. 2,6-dimethyl-4-tridecyl-morpholine, methyl N-(1-butyl-carbamoyl-benzimidazol-2-yl)carbamate, 1,2-bis-(3-methoxycarbonyl-2-thioureido)benzene, isopropyl 1-carbamoyl-3-(3,5-dichlorophenyl)-hydantoin and 1-(4-chloro-phenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the N-phenyl-pyrazole derivatives of general formula II or, as is preferred, a herbicidal composition as hereinbefore described, and preferably a herbicidal concentrate which must be diluted before use, comprising at least one of the N-phenylpyrazole derivatives of general formula II within a container for the aforesaid derivative or derivatives of general formula II, or a said herbicidal composition, and instructions physically associated with the aforesaid container setting out the manner in which the aforesaid derivative or derivatives of general formula II or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally-lacquered, and plastics materials, bottles of glass and plastics materials and, when the contents of the container is a solid, for example granular, herbicidal compositions, boxes, for example of cardboard, plastics materials and metal, or sacks. The containers will normally be of sufficient capacity to contain amounts of the N-phenylpyrazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 10 kg of active material per hectare in the manner and for the purposes hereinbefore described.

The following Examples illustrate herbicidal compositions according to the present invention.

EXAMPLE 1

5-Acetamido-4-cyano-1-(2,3,4-trichlorophenyl)-pyrazole was formulated as a water soluble concentrate containing

| | |
|---|---|
| 5-acetamido-4-cyano-1-(2,3,4-trichlorophenyl)-pyrazole | 10% w/v (weight/volume) |
| Ethylan KEO (nonylphenyl/ethylene oxide condensate containing 9–10 moles of ethylene oxide per mol of phenol) | 10% w/v |
| Dimethylformamide to | 100% by volume, | by dissolving the Ethylan KEO in a portion of dimethylformamide and then adding the active ingredient with heating and stirring until dissolved. The resulting solution was then made up to 100% by volume by adding the rest of the dimethylformamide.

5 Liters of the above formulation may be dissolved in 200 liters of water and sprayed post-emergence onto 1 hectare of an emerged crop of spring-sown wheat to control *Amaranthus retroflexus, Setaria viridis, Polygonum lapathifolium, Abutilon theophrasti* and *Solanum nigrum*.

The 5-acetamido-4-cyano-1-(2,3,4-trichlorophenyl)-pyrazole may, if desired, be replaced in the above water soluble concentrate by any other compound of general formula II.

EXAMPLE 2

A wettable powder was formed from:

| | |
|---|---|
| 5-acetamido-4-cyano-1-(2,3,4-trichlorophenyl)pyrazole | 50% w/w (weight/weight) |
| Ethylan BCP (a nonylphenol/ethylene oxide condensate containing 9 moles of ethylene oxide per mol of phenol) | 5% w/w |
| Aerosil (silicon dioxide of microfine particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder which may be diluted with water and applied at an application rate of 2 kg of wettable powder in 300 liters of spray fluid per hectare to control the growth of *Galium aparine, Veronica persica, Viola arvensis, Stellaria media* and *Galeopsis tetrahit* by post-emergence application in an emerged crop of winter wheat.

Similar wettable powders may be prepared as described above by replacing the 5-acetamido-4-cyano-1-(2,3,4-trichlorophenyl)pyrazole by other compounds of general formula II.

EXAMPLE 3

An aqueous suspension concentrate was formed from:

| | |
|---|---|
| 5-acetamido-4-cyano-1-(2,3,4-trichlorophenyl)pyrazole | 50% w/v |
| Ethylan BCP | 1.0% w/v |
| Sopropon T36 (sodium salt of polycarboxylic acid) | 0.2% w/v |
| Ethylene glycol | 5% w/v |
| Rhodigel 23 (polysaccharide xanthan gum thickener) | 0.15% w/v |
| distilled water to | 100% by volume | by intimately mixing the ingredients and grinding in a ball-mill for 24 hours. The concentrate thus obtained may be dispersed in water and applied at an application rate of 1 kg of aqueous suspension concentrate in 300 liters of spray fluid per hectare to control the growth of *Galium aparine, Veronica persica, Viola arvensis, Stellaria media* and *Galeopsis tetrahit* by post-emergence application in an emerged crop of winter barley.

Similar aqueous suspension concentrates may be prepared as described above by replacing the 5-acetamido-4-cyano-1-(2,3,4-trichlorophenyl)-pyrazole by other compounds of general formula II.

EXAMPLE 4

An emulsifiable suspension concentrate was formed from:

| | |
|---|---|
| 5-acetamido-4-cyano-1-(2,3,4-trichlorophenyl)pyrazole | 50% w/v |
| Ethylan TU (a nonyl phenol/ethylene oxide condensate containing 10 moles of ethylene oxide per mol of phenol) | 10% w/v |
| Bentone 38 (an organic derivative of special magnesium montmorillonite thickener) | 0.5% w/v |
| Aromasol H (an aromatic solvent consisting predominantly of isomeric | to 100% by volume | by intimately mixing the ingredients and grinding in a ball-mill for 24 hours. The emulsifiable suspension concentrate thus obtained may be diluted with water and applied at an application rate of 1.5 kg of emulsifiable suspension concentrate in 100 liters of spray fluid per hectare to control the growth of *Setaria viridis, Polygonum convolvulus,* and *Chenopodium album* by post-emergence application in an emerged crop of springsown wheat.

Similar emulsifiable suspension concentrates may be prepared as described above by replacing the 5-acetamido-4-cyano-1-(2,3,4-trichlorophenyl)pyrazole by other compounds of general formula II.

EXAMPLE 5

Granules were formed from:

| | |
|---|---|
| 5-acetamido-4-cyano-1-(2,3,4-trichlorophenyl)pyrazole | 5% w/w |
| Ethylan BCP | 1% w/w |
| Oleic acid | 1% w/w |
| Aromasol H | 12% w/w |
| 30/60 Attapulgite granules (sorptive silica clay) | 81% w/w | by mixing the phenylpyrazole, Ethylan BCP, oleic acid and Aromasol H and spraying the mixture onto the Attapulgite granules. The granules thus obtained may be applied at an application rate of 20 kg of granules per hectare to control the growth of *Echinochloa crus-galli, Eleocharis acicularis* and *Monochoria vaginalis* by pre-emergence application or application to seedling weeds in a crop of transplanted paddy rice.

Similar granules may be prepared as described above by replacing the 5-acetamido-4-cyano-1-(2,3,4-trichlorophenyl)pyrazole by other compounds of general formula II.

EXAMPLE 6

A water soluble concentrate was formed from:

| | |
|---|---|
| 5-acetamido-4-cyano-1-(2,3,4-trichlorophenyl)pyrazole | 10% w/v |
| Ethylan KEO | 10% w/v |
| Dimethylformamide | to 100% by volume | by dissolving the Ethylan KEO in a portion of dimethylformamide and then adding the pyrazole derivative with heating and stirring until dissolved. The resulting solution was then made up to 100% by volume with dimethylformamide by adding the rest of the dimethylformamide. The water soluble concentrate thus obtained may be diluted with water and applied at an application rate of 10 liters of water soluble concentrate in 200 to 2000 liters of spray fluid per hectare to control the growth of *Galium aparine, Veronica persica, Viola arvensis* and *Galeopsis tetrahit* by post-emergence application in an emerged crop of winter wheat at the tillering growth stage.

EXAMPLE 7

A wettable powder was formed from:

| | |
|---|---|
| 5-acetamido-4-cyano-1-(2,3,4-trichlorophenyl)pyrazole | 90% w/w |
| Arylan S (sodium dodecyl benzene sulphonate) | 2% w/w |
| Darvan No. 2 (sodium lignosulphate) | 5% w/w |
| Celite PF | 3% w/w | by mixing the ingredients and grinding the mixture in a hammer-mill to give a wettable powder which may be diluted with water and applied at an application rate of 1 kg of wettable powder in 300 liters of spray fluid per hectare to control the growth of *Galium aparine, Veronica persica, Viola arvensis* and *Galeopsis tetrahit* by post-emergence application in an emerged crop of winter wheat.

Similar wettable powders may be prepared as described above by replacing the 5-acetamido-4-cyano-1-(2,3,4-trichlorophenyl)pyrazole by other compounds of general formula II.

EXAMPLE 8

A wettable powder containing 50% w/w of 5-acetamido-4-cyano-1-(2,3,4-trichlorophenyl)pyrazole, prepared as hereinbefore described in Example 2, may be diluted with water and applied at an application rate of 0.1 kg of wettable powder in 300 liters of spray fluid per hectare to control the growth of *Abutilon theophrasti* and *Polygonum convolvulus* by post-emergence application at the early seedling growth stage of these weeds in a crop of spring wheat.

EXAMPLE 9

A wettable powder containing 50% w/w of 5-acetamido-4-cyano-1-(2,3,4-trichlorophenyl)pyrazole, prepared as described in Example 2, may be diluted with water and applied at an application rate of 20 kg of wettable powder in 600 liters of spray fluid per hectare to produce a total herbicidal effect on vegetation at a locus which is not a crop-growing area.

EXAMPLE 10

A wettable powder containing 50% w/w of acylamino-N-phenylpyrazole derivative was prepared as hereinbefore described in Example 2 but replacing the 5-acetamido-4-cyano-1-(2,3,4-trichlorophenyl)pyrazole by 1-(2-chloro-4-trifluoromethylphenyl)-4-cyano-5-propionamidopyrazole. This wettable powder may be diluted with water and applied at an application rate of 0.02 kg of wettable powder in 300 liters of spray fluid per hectare to control the growth of *Abutilon theophrasti* and *Polygonum convolvulus* by post-emergence application at the early seedling stage of these weeds in an emerged crop of spring wheat.

EXAMPLE 11

An emulsifiable concentrate was formed from:

| | |
|---|---|
| 5-acetamido-4-cyano-1-(2,3,5,6-tetrafluoro-4-trifluoromethyl-phenyl)pyrazole | 10% w/v |
| Arylan CA (60% calcium dodecylbenzene sulphonate) | 3% w/v |
| Soprophor BSU (polyarylphenol ethoxylate) | 7% w/v |
| Isophorone | 30% w/v |
| Solvesso 150 (solvent mixture containing predominantly $C_{10}$–$C_{13}$ aromatic isomers) | to 100% by volume | by dissolving the Arylan CA and Soprophor BSU in the isophorone and then adding the phenylpyrazole with gentle heating and stirring. The Solvesso 150 was then added to the resulting solution to 100% by volume. The emulsifiable concentrate thus obtained may be diluted with water and applied at a rate of 2 liters of emulsifiable concentrate in 200 liters of spray fluid per hectare to control the growth of Digitaria sanguinalis, Chenopodium album, Abutilon theophrasti, Polygonum lapathifolium, Amaranthus retroflexus and Setaria viridis in a crop of soya beans by application before emergence of both the crop and weeds.

According to a further feature of the present invention, the compounds of general formula II wherein $R^1$ represents an $R^9C(=O)$— group, wherein $R^9$ represents a straight- or branched-chain alkyl group containing from 1 to 7 carbon atoms, a straight- or branched-chain alkoxy group containing from 1 to 4 carbon atoms or a straight- or branched-chain alkenyloxy group containing 3 or 4 carbon atoms, alkyl and alkoxy groups within the definition of $R^9$ being unsubstituted or substituted by a straight- or branched-chain alkoxy group containing from 1 to 4 carbon atoms, an alkoxycarbonyl group containing from 2 to 5 carbon atoms, or one or more halogen, e.g. chlorine, atoms, or $R^9$ represents a cycloalkyl group containing from 3 to 6 carbon atoms, unsubstituted or substituted by a methyl or ethyl group or $R^9$ represents a phenoxy group, $R^2$ represents a hydrogen atom or an $R^9C(=O)$— group, wherein $R^9$ is as hereinbefore defined, which is identical to the group $R^9C(=O)$ represented by $R^1$, and $R^3$, $R^4$, $R^5$, $R^6$ and $R^7$ are as hereinbefore defined, i.e. compounds of the general formula:

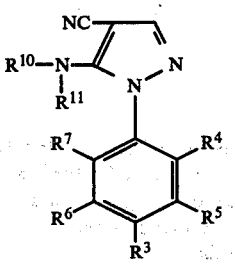

IIA wherein $R^{10}$ represents an $R^9C(=O)$— group, wherein $R^9$ is as hereinbefore defined, $R^{11}$ represents a hydrogen atom or an $R^9C(=O)$— group, wherein $R^9$ is as hereinbefore defined and is identical to the group represented by the symbol $R^9$ in the definition of the symbol $R^{10}$, and $R^3$, $R^4$, $R^5$, $R^6$ and $R^7$ are as hereinbefore defined, are prepared by the reaction of a compound of the general formula:

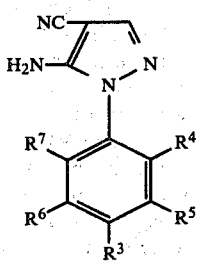

III wherein $R^3$, $R^4$, $R^5$, $R^6$ and $R^7$ are as hereinbefore defined, with a compound of the general formula:

$$R^9COX \quad \text{IV}$$

wherein X represents a chlorine or bromine atom and $R^9$ is as hereinbefore defined, or with a compound of the general formula:

$$(R^9CO)_2O \quad \text{V}$$

wherein $R^9$ is as hereinbefore defined, in the absence or presence of a suitable inert organic solvent, for example a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. to the reflux temperature of the reaction medium, to give a compound of general formula IIA wherein $R^{10}$ is as hereinbefore defined and $R^{11}$ represents either a hydrogen atom or an $R^9C(=O)$— group, wherein $R^9$ is as hereinbefore defined, depending upon the reaction conditions chosen and/or the use of an excess of the compound of general formula IV or V. If desired, an alkali metal derivative of the compound of general formula III may be used.

According to a further feature of the present invention, the compounds of general formula II wherein $R^1$ represents an $R^8C(=O)$— group, wherein $R^8$ represents a hydrogen atom, $R^2$ represents a hydrogen atom and $R^3$, $R^4$, $R^5$, $R^6$ and $R^7$ are as hereinbefore defined, i.e. compounds of the general formula:

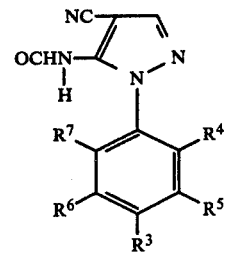

IIB wherein $R^3$, $R^4$, $R^5$, $R^6$ and $R^7$ are as hereinbefore defined, are prepared by reaction of a compound of general formula III, wherein $R^3$, $R^4$, $R^5$, $R^6$ and $R^7$ are as hereinbefore defined, with formic acid, in a suitable inert organic solvent, for example a ketone, e.g. methylisobutyl ketone, or an aromatic hydrocarbon, e.g. benzene or toluene, at the reflux temperature of the reaction mixture.

According to a further feature of the present invention, the compounds of general formula II wherein $R^1$ represents an $R^8C(=O)$— group, wherein $R^8$ represents a hydrogen atom, $R^2$ represents a hydrogen atom or an $R^8C(=O)$— group, wherein $R^8$ represents a hydrogen atom, and $R^3$, $R^4$, $R^5$, $R^6$ and $R^7$ are as hereinbefore defined, i.e. compounds of the general formula:

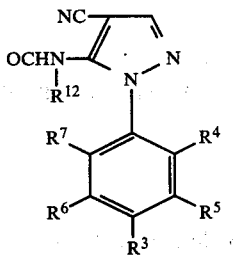

wherein $R^{12}$ represents a hydrogen atom or an HC(=O)— group and $R^3$, $R^4$, $R^5$, $R^6$ and $R^7$ are as hereinbefore defined, are prepared by the reaction of a compound of general formula III, wherein $R^3$, $R^4$, $R^5$, $R^6$ and $R^7$ are as hereinbefore defined, with formylacetic anhydride (which may be prepared from formic acid and acetic anhydride), in the absence or presence of a suitable inert organic solvent, for example a ketone, e.g. acetone, or an aromatic hydrocarbon, e.g. benzene or toluene, and optionally in the presence of an acid-binding agent, for example pyridine, triethylamine or an alkali metal, e.g. sodium or potassium, carbonate or bicarbonate, at a temperature from 0° C. to the reflux temperature of the reaction mixture, to give a compound of general formula II C wherein $R^3$, $R^4$, $R^5$, $R^6$ and $R^7$ are as hereinbefore defined and $R^{12}$ represents a hydrogen atom or an HC(=O)— group, depending upon the reaction conditions chosen and/or the use of an excess of formylacetic anhydride.

According to a further feature of the present invention, the compounds of general formula II wherein $R^1$ represents an $R^8$C(=O)— group, wherein $R^8$ is as hereinbefore defined, $R^2$ represents a hydrogen atom and $R^3$, $R^4$, $R^5$, $R^6$ and $R^7$ are as hereinbefore defined, i.e. compounds of the general formula:

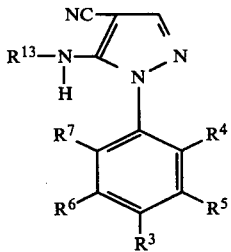

wherein $R^{13}$ represents an $R^8$C(=O)— group, wherein $R^8$ is as hereinbefore defined, and $R^3$, $R^4$, $R^5$, $R^6$ and $R^7$ are as hereinbefore defined, are prepared by the selective removal by hydrolysis of an $R^9$C(=O)— group represented by the symbol $R^{11}$ of a compound of general formula II A (wherein $R^3$, $R^4$, $R^5$, $R^6$, $R^7$ and $R^{10}$ are as hereinbefore defined) or an HC(=O)— group represented by the symbol $R^{12}$ of a compound of general formula II C (wherein $R^3$, $R^4$, $R^5$, $R^6$ and $R^7$ are as hereinbefore defined). Hydrolysis is effected under mild conditions, for example by treatment with an aqueous-ethanolic solution or suspension of an alkali metal, e.g. sodium or potassium, bicarbonate, or with aqueous ammonia.

According to a further feature of the present invention, the compounds of general formula II wherein $R^1$ represents an $R^8$C(=O)— group, wherein $R^8$ represents a straight- or branched-chain alkoxy group containing from 1 to 4 carbon atoms unsubstituted or substituted by an alkoxy group containing from 1 to 4 carbon atoms, an alkoxycarbonyl group containing from 2 to 5 carbon atoms, or one or more halogen, e.g. chlorine, atoms, $R^2$ represents a hydrogen atom and $R^3$, $R^4$, $R^5$, $R^6$ and $R^7$ are as hereinbefore defined, i.e. compounds of the general formula:

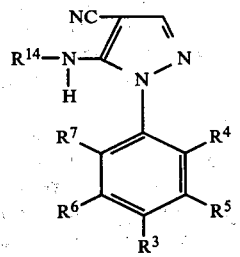

wherein $R^{14}$ represents an $R^{15}$C(=O)— group, wherein $R^{15}$ represents a straight- or branched-chain alkoxy group containing from 1 to 4 carbon atoms unsubstituted or substituted by an alkoxy group containing from 1 to 4 carbon atoms, an alkoxycarbonyl group containing from 2 to 5 carbon atoms, or one or more halogen, e.g. chlorine, atoms, and $R^3$, $R^4$, $R^5$, $R^6$ and $R^7$ are as hereinbefore defined, are prepared by the reaction of a compound of the general formula:

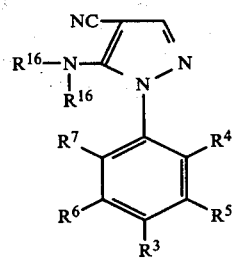

wherein $R^{16}$ represents a group $R^{17}$ C(=O), wherein $R^{17}$ represents a group within the definition of $R^{15}$ as hereinbefore defined or a phenoxy group, and $R^3$, $R^4$, $R^5$, $R^6$ and $R^7$ are as hereinbefore defined, with a compound of the general formula:

$R^{15}$OH    VI wherein $R^{15}$ is as hereinbefore defined, to replace one of the groups represented by the symbol $R^{16}$ by a hydrogen atom, to replace the other group represented by the symbol $R^{16}$ by a group within the definition of $R^{14}$ when $R^{16}$ represents a group $R^{17}$ C(=O) wherein $R^{17}$ represents a phenoxy group, and, if desired, to replace the other group represented by the symbol $R^{16}$ by another group represented by the symbol $R^{14}$ and $R^{16}$ represents a group $R^{17}$ C(=O), wherein $R^{17}$ represents a group within the definition of $R^{15}$. As will be apparent to those skilled in the art, the desired compound of general formula II E is obtained by selection of the appropriate compounds of general formulae II F and VI. The reaction may be effected in water or a suitable inert aqueous-organic or organic solvent, for example an alkanol containing 1 to 4 carbon atoms, e.g. ethanol, or an aromatic hydrocarbon, e.g. benzene or toluene, or which is preferably an excess of the compound of general formula VI, at a temperature from ambient temperature to the reflux temperature of the reaction mixture and, if necessary, at elevated pressure, and optionally in the presence of a base, for example an alkali metal alkoxide, e.g. of the compound of general formula VI.

According to a further feature of the present invention, the compounds of general formula II wherein $R^1$ represents an $R^8 C(=O)-$ group, wherein $R^8$ is as hereinbefore defined, $R^2$ represents an $R^8 C(=O)-$ group, wherein $R^8$ is as hereinbefore defined, which may be the same as, or different to, the $R^8 C(=O)-$ group represented by the symbol $R^1$ and $R^3$, $R^4$, $R^5$, $R^6$ and $R^7$ are as hereinbefore defined, i.e. compounds of the general formula:

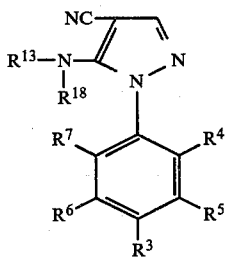
IIG wherein $R^3$, $R^4$, $R^5$, $R^6$, $R^7$ and $R^{13}$ are as hereinbefore defined and $R^{18}$ represents an $R^8 C(=O)-$ group, wherein $R^8$ is as hereinbefore defined, which may be the same as, or different to, the $R^8 C(=O)-$ group represented by the symbol $R^{13}$, are prepared by the reaction of an alkali metal, e.g. sodium or potassium, derivative of a compound of general formula II A, wherein $R^3$, $R^4$, $R^5$, $R^6$, $R^7$ and $R^{10}$ are as hereinbefore defined and $R^{11}$ represents a hydrogen atom, or of a compound of general formula II B, wherein $R^3$, $R^4$, $R^5$, $R^6$ and $R^7$ are as hereinbefore defined, i.e. a compound of general formula II D wherein $R^3$, $R^4$, $R^5$, $R^6$, $R^7$ and $R^{13}$ are as hereinbefore defined, with formic acid, formylacetic anhydride or a compound of general formula IV, wherein $R^9$ and X are as hereinbefore defined. Reaction may be effected in a suitable aprotic solvent, e.g. dimethylformamide, at a temperature from laboratory temperature to the reflux temperature of the reaction mixture.

According to a further feature of the present invention, the compounds of general formula II wherein $R^1$ and $R^2$ together represent $-OC-(CR^aR^b)_m-CO-$ and $R^3$, $R^4$, $R^5$, $R^6$, $R^7$, $R^a$, $R^b$ and m are as hereinbefore defined, are prepared by the reaction of a compound of general formula III, wherein $R^3$, $R^4$, $R^5$, $R^6$ and $R^7$ are as hereinbefore defined, with a compound of the general formula:

$$XOC-(CR^aR^b)_m-COX \qquad VII$$

wherein X, $R^a$, $R^b$ and m are as hereinbefore defined, or with a compound of the general formula:

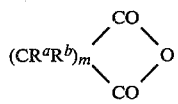
VIII wherein $R^a$, $R^b$ and m are as hereinbefore defined, in the absence or presence of a suitable inert organic solvent, for example a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. to the reflux temperature of the reaction medium. If desired, an alkali metal derivative of the compound of general formula III may be used.

Alkali metal derivatives of compounds of general formula III or II D may be prepared in situ by reaction of the compounds of general formula III or II D, wherein $R^3$, $R^4$, $R^5$, $R^6$, $R^7$ and $R^{13}$ are as hereinbefore defined, with an alkali metal, e.g. sodium or potassium, hydride, in a suitable inert aprotic solvent, e.g. dimethylformamide, at a temperature from laboratory temperature to the reflux temperature of the reaction mixture.

The compounds of general formula III, wherein $R^3$, $R^4$, $R^5$, $R^6$ and $R^7$ are as hereinbefore defined, may be prepared by the process which comprises the cyclisation of a compound of the general formula:

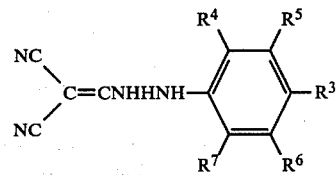
IX wherein $R^3$, $R^4$, $R^5$, $R^6$ and $R^7$ are as hereinbefore defined. Cyclisation may be effected in the presence of an inert organic solvent, for example an alcohol containing from 1 to 4 carbon atoms, e.g. ethanol, acetic acid or ethoxyethanol, at a temperature of from ambient temperature to the reflux temperature of the reaction mixture.

Compounds of general formula IX may be prepared by the reaction of a compound of the general formula:

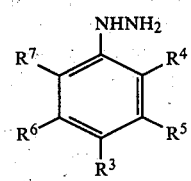
X wherein $R^3$, $R^4$, $R^5$, $R^6$ and $R^7$ are as hereinbefore defined, or an acid addition salt thereof, e.g. the hydrochloride, with a compound of the general formula:

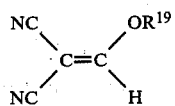
XI wherein $R^{19}$ represents a straight- or branched-chain alkyl group containing from 1 to 4 carbon atoms, preferably ethyl.

The reaction of a compound of general formula X with a compound of general formula XI may be effected in the presence of an inert organic solvent, for example an alkanol containing from 1 to 4 carbon atoms, e.g. ethanol, acetic acid or ethoxyethanol, and at a temperature from ambient temperature to the reflux temperature of the reaction mixture and optionally in the presence of an alkali metal, e.g. sodium or potassium, acetate, carbonate or bicarbonate. When an acid addition salt of the compound of general formula X is used, the reaction with the compound of general formula XI is effected in the presence of an alkali metal, e.g. sodium or potassium, acetate, carbonate or bicarbonate.

The compounds of general formula III may be prepared by reaction of a compound of general formula X with a compound of general formula XI without isolation of an intermediate compound of general formula IX from the reaction mixture. When the reaction of a compound of general formula X with a compound of general formula XI is effected in acetic acid, in the absence or presence of an alkali metal, e.g. sodium or potassium, acetate, the intermediate compound of general formula IX may separate from the reaction mixture, depending upon the solubility of the intermediate compound of general formula IX in the reaction medium, and may, if desired, be isolated before being cyclised as hereinbefore described to a compound of general formula III, preferably by heating in an inert organic solvent, e.g. ethoxyethanol, at the reflux temperature of the reaction mixture.

Compounds of general formulae X and XI may be prepared by methods known per se. (By the term 'methods known per se' as used in the present specification is meant methods heretofore used or described in the chemical literature).

The following Examples and Reference Examples illustrate the preparation of compounds of general formula II.

EXAMPLE 12

Compounds 1 and 5

5-Amino-4-cyano-1-(2,3,4-trichlorophenyl)pyrazole (28.7 g) was heated at reflux in acetic anhydride (150 ml) for 8 hours. The reaction mixture was then evaporated to dryness and the solid residue was suspended in ethanol (250 ml). Saturated aqueous sodium bicarbonate solution was then added to give a pH of 8 and the suspension was then stirred magnetically for 16 hours. The solid obtained was separated by filtration, washed with water and dried, to give 5-acetamido-4-cyano-1-(2,3,4-trichlorophenyl)pyrazole (23.7 g), m.p. 222°–224° C., in the form of an off-white powder.

By proceeding in a similar manner but replacing the acetic anhydride by propionic anhydride, there was prepared 4-cyano-5-propionamido-1-(2,3,4-trichlorophenyl)pyrazole, m.p. 189°–190° C., after crystallisation from toluene.

EXAMPLE 13

Compound 2

5-Amino-4-cyano-1-(2,3,4-trichlorophenyl)pyrazole (2.9 g) was heated at reflux in acetic anhydride (30 ml) for 24 hours. The reaction mixture was then evaporated to dryness under reduced pressure (20 mmHg), to give a brown solid, which was then triturated with diethylether (20 ml) and boiled with ethanol (25 ml) for one hour. The insoluble material (1.5 g) was separated by filtration and crystallized from toluene (10 ml) to give 4-cyano-5-diacetylamino-1-(2,3,4-trichlorophenyl)pyrazole (1.2 g), m.p. 163°–165° C., in the form of a colourless crystalline solid.

EXAMPLE 14

Compound 1

4-Cyano-5-diacetylamino-1-(2,3,4-trichlorophenyl)pyrazole (0.2 g) in ethanol (5 ml) containing saturated aqueous sodium bicarbonate solution (4 drops), was heated at reflux for 20 minutes. The reaction mixture was then evaporated to dryness under reduced pressure (20 mmHg) to give a fawn coloured powder which was crystallized from ethanol (2 ml), to give 5-acetamido-4-cyano-1-(2,3,4-trichlorophenyl)pyrazole (0.09 g), m.p. 222°–224° C., in the form of a colourless crystalline solid.

EXAMPLE 15

Compound 1

5-Amino-4-cyano-1-(2,3,4-trichlorophenyl)pyrazole (2.9 g) in acetylchloride (15 mg) was heated at reflux for 2 hours. The reaction mixture was then filtered and the solid residue was triturated with acetyl chloride (10 ml), to give 5-acetamido-4-cyano-1-(2,3,4-trichlorophenyl)pyrazole (2.0 g), m.p. 220°–223° C., in the form of a colourless powder.

EXAMPLE 16

Compounds 3 and 6

5-Amino-4-cyano-1-(2,3,5,6-tetrafluoro-4-trifluoromethylphenyl)pyrazole (6.5 g) in acetic anhydride (30 ml) was heated at reflux for 3.5 hours. The reaction mixture was then evaporated to dryness and the solid residue was dissolved in ethanol (50 ml). Saturated aqueous sodium bicarbonate solution was then added to give a pH of 7–8 and the solution was then evaporated to dryness. The solid residue was triturated with hexane (20 ml) to give an off-white powder which was crystallized from toluene (50 ml) to give 5-acetamido-4-cyano-1-(2,3,5,6-tetrafluoro-4-trifluoromethylphenyl)pyrazole (1.4 g), m.p. 153°–154° C., in the form of colourless crystals.

By proceeding in a similar manner, but replacing the 5-amino-4-cyano-1-(2,3,5,6-tetrafluoro-4-trifluoromethylphenyl)pyrazole by 5-amino-4-cyano-1-(2,4,6-trichlorophenyl)pyrazole, there was prepared 5-acetamido-4-cyano-1-(2,4,6-trichlorophenyl)pyrazole, m.p. 163°–164° C., in the form of colourless crystals, after crystallisation from toluene.

EXAMPLE 17

Compound 4

Sodium hydride (0.5 g) was added to a solution of 5-amino-4-cyano-1-(2,3,4-trichlorophenyl)pyrazole (5.8 g) in dimethylformamide (20 ml). After the initial exothermic reaction had subsided, the solution was heated on a steam-bath for 5 minutes and then cooled to 10° C. Phenyl chloroformate (2.8 ml) was then added slowly in small portions with occasional cooling with water to keep the temperature below 50° C. The mixture was then heated on a steam-bath for 10 minutes, cooled and evaporated to dryness. The solid residue was treated with diethyl ether (300 ml). The ethereal suspension was filtered and the filtrate was evaporated to dryness. The solid residue thus obtained was boiled in ethanol (200 ml) and separated by filtration, to give 4-cyano-5-di(phenoxycarbonyl)amino-1-(2,3,4-trichlorophenyl)pyrazole (1.7 g), m.p. 206°–208° C., in the form of colourless crystals.

EXAMPLE 18

Compound 6

5-Amino-4-cyano-1-(2,4,6-trichlorophenyl)pyrazole (10 g) in acetic anhydride (52 ml) was heated at reflux for 8 hours. The reaction mixture was then cooled and evaporated to dryness and the residue was crystallised from toluene to give a solid (7.0 g), m.p. 155°–159° C., which was recrystallised from toluene (50 ml) to give 5-acetamido-4-cyano-1-(2,4,6-trichlorophenyl)pyrazole (5.0 g), m.p. 163°–164° C., in the form of colourless crystals.

EXAMPLE 19

Compounds 7 and 8

5-Amino-4-cyano-1-(4-methyl-2,3,5,6-tetrafluorophenyl)pyrazole (5.4 g) in acetic anhydride (30 ml) was heated at reflux for 10 hours. The reaction mixture was evaporated to dryness and the residue was evaporated in the presence of toluene (4×20 ml) and xylene (50 ml) to give a white semi-solid, which was dissolved in toluene (20 ml). Insoluble material was removed by filtration and the filtrate was evaporated to dryness to give an orange semi-solid (4.2 g) which was triturated with diethyl ether. The suspension thus obtained was filtered and the precipitate was washed with diethyl ether to give 4-cyano-5-diacetylamino-1-(4-methyl-2,3,5,6-tetrafluorophenyl)pyrazole (1.8 g), m.p. 132°–133° C., in the form of a colourless solid.

The filtrate from the filtration of the suspension obtained by trituration of the orange semi-solid with diethyl ether, deposited a solid precipitate on standing. This precipitate was removed by filtration and the filtrate thus obtained was diluted with hexane to precipitate 5-acetamido-4-cyano-1-(4-methyl-2,3,5,6-tetrafluorophenyl)pyrazole (0.9 g), m.p. 161°–163° C., in the form of a colourless solid.

EXAMPLE 20

Compound 9

5-Amino-4-cyano-1-(2,3,6-trichloro-4-trifluoromethylphenyl)pyrazole (3.74 g) in acetic anhydride (20 ml) was heated at reflux for 6 hours. The reaction mixture was then evaporated under reduced pressure to remove unreacted acetic anhydride. The residual oil was dissolved in dichloromethane (50 ml) and filtered. The filtrate was evaporated to give a foam, which was then suspended in water (70 ml). The suspension was filtered and the filtrate deposited a solid on standing. The solid was collected by filtration and washed with water to give 5-acetamido-4-cyano-1-(2,3,6-trichloro-4-trifluoromethylphenyl)pyrazole (0.4 g), m.p. 177°–178° C., in the form of a fawn-coloured solid.

EXAMPLE 21

Compound 10

5-Amino-4-cyano-1-(2,3,4,6-tetrachlorophenyl)pyrazole (7.1 g) in acetic anhydride (40 ml) was heated at reflux for 17 hours. The reation mixture was then evaporated to dryness and the residue was evaporated in the presence of toluene (3×500 ml) to give a brown oil. The brown oil was triturated with diethyl ether. A solid precipitated and was collected and washed with diethyl ether to give a colourless solid (2.4 g), m.p. 110° C. The solid thus obtained was crystallised from toluene (25 ml) to give 5-acetamido-4-cyano-1-(2,3,4,6-tetrachlorophenyl)pyrazole (1.3 g; containing 0.2M of toluene), m.p. 115° C., in the form of colourless crystals. The diethyl ether filtrate and washings and the toluene filtrate were combined and evaporated to dryness. The residue thus obtained was triturated with diethyl ether (50 ml). The solid which precipitated was collected by filtration to give a second crop of 5-acetamido-4-cyano-1-(2,3,4,6-tetrachlorophenyl)-pyrazole (2.5 g; containing 0.2M of toluene), m.p. 115° C. in the form of a colourless solid.

EXAMPLE 22

Compounds 11, 12, 13, 22, 23, 20 and 21

Acetyl chloride (34 ml) was added to a stirred suspension of 5-amino-1-(2-chloro-4-methylphenyl)-4-cyanopyrazole (8.0 g) in chloroform (34 ml) at 0° C. A solution of pyridine (5.4 ml) in chloroform (34 ml) was then added to the suspension thus obtained over 10 minutes, with stirring at 0° C. to 2° C. maintained by external cooling. The reaction mixture was then stirred at laboratory temperature for 2.5 hours and the solution thus obtained was evaporated to dryness. The residue was dissolved in ethanol (100 ml) and basified with aqueous ammonia (d: 0.880). The basified solution was heated at reflux for 10 minutes and then evaporated to dryness. The residue was dissolved in dichloromethane (500 ml) and water (500 ml) and the organic layer was separated, washed successively once with water, twice with 2N hydrochloric acid and twice with water, dried over anhydrous magnesium sulphate and evaporated. The colourless solid thus obtained was crystallised from toluene (30 ml) to give 5-acetamido-1-(2-chloro-4-methylphenyl)-4-cyanopyrazole (6.54 g), m.p. 146°–147° C., in the form of colourless crystals.

By proceeding in a similar manner but replacing the 5-amino-1-(2-chloro-4-methylphenyl)-4-cyanopyrazole by the hereinafter indicated appropriately substituted phenylpyrazole, there were obtained: 5-Acetamido-1-(4-allyl-2,3,5,6-tetrafluorophenyl)-4-cyanopyrazole, m.p. 90°–91.5° C., in the form of colourless crystals, after crystallisation from aqueous ethanol, from 1-(4-allyl-2,3,5,6-tetrafluorophenyl)-5-amino-4-cyanopyrazole; 5-Acetamido-1-(2-chloro-4-ethylphenyl)-4-cyanopyrazole, m.p. 140°–141° C., in the form of buff-coloured crystals, after crystallisation from toluene, from 5-amino-1-(2-chloro-4-ethylphenyl)-4-cyanopyrazole; 5-Acetamido-4-cyano-1-(2,3-dichlorophenyl)pyrazole, m.p. 246°–248° C., in the form of colourless crystals, after crystallisation from a mixture of toluene and ethanol, from 5-amino-4-cyano-1-(2,3-dichlorophenyl)pyrazole; 5-Acetamido-4-cyano-1-(2,4-dichlorophenyl)pyrazole, m.p. 188°–190° C., in the form of colourless crystals, after crystallisation from a mixture of toluene and ethanol, from 5-amino-4-cyano-1-(2,4-dichlorophenyl)pyrazole [described by P. L. Southwick and B. Dhawan J. Heter. Chem. 12 1199–1205 (1975)].

By proceeding in a similar manner, but replacing the acetyl chloride by the hereinafter indicated acid chloride and the 5-amino-1-(2-chloro-4-methylphenyl)-4-cyanopyrazole by 5-amino-4-cyano-1-(2,3,4-trichlorophenyl)pyrazole, and carrying out the reaction at 20° C. rather than 0° C., there were prepared: 4-Cyano-5-n-hexanamido-1-(2,3,4-trichlorophenyl)pyrazole, m.p. 114°–114.5° C., in the form of colourless crystals, after crystallisation from aqueous ethanol, from n-hexanoyl chloride; 4-Cyano-5-n-octanamido-1-(2,3,4-trichlorophenyl)pyrazole, m.p. 134°–136° C., in the form of colourless crystals, after crystallisation from aqueous ethanol (50%), from n-octanoyl chloride.

EXAMPLE 23

Compound 14

5-Amino-4-cyano-1-(2,3,4-trichlorophenyl)pyrazole (172.5 g) in propionyl chloride (600 ml) was heated at reflux for 17 hours. The reaction mixture was evaporated to dryness and the residue was evaporated in the presence of toluene (3×500 ml) to give a dark gum. This gum was stirred with diethyl ether (1000 ml) and the solid which precipitated was collected by filtration and washed with diethyl ether to give a fawn-coloured solid (97 g), m.p. 127°–129° C. The solid thus obtained was crystallised from toluene (300 ml) to give a colourless solid (13.8 g), m.p. 250°–251° C. The toluene mother liquors were cooled and the solid which precipitated was collected by filtration and washed with diethyl ether to give 4-cyano-5-dipropionylamino-1-(2,3,4-trichlorophenyl)pyrazole (15.0 g), m.p. 133°–134° C., in the form of colourless crystals.

EXAMPLE 24

Compounds 15, 16, 17, 18, 24, 19, 25, 26, 27, 33, 28, 29 and 30 n-Butyryl chloride (4.7 ml) was added to a stirred suspension of 5-amino-4-cyano-1-(2,3,4-trichlorophenyl)pyrazole (5.8 g) in chloroform (30 ml) at 0° C. and a solution of pyridine (3.2 ml) in chloroform (30 ml) was then added over 10 minutes, with stirring at 0°–5° C. maintained by external cooling, to the suspension thus obtained. The reaction mixture was then stirred for 17 hours at laboratory temperature. Saturated aqueous potassium bicarbonate solution (100 ml) was added at 20° C. to the clear solution thus obtained and the mixture was stirred vigorously for 1 hour. The chloroform layer was separated, washed with 2N hydrochloric acid and water, and evaporated to give an oil. This oil was dissolved in ethanol (150 ml) and saturated aqueous potassium bicarbonate solution (25 ml) was added. The solution thus obtained was heated at reflux for 1.5 hours and evaporated to dryness. The residue was dissolved in dichloromethane, washed with water, dried over anhydrous magnesium sulphate and evaporated to dryness, to give an oil (5.5 g) which was crystallised from toluene (25 ml) to give 5-n-butyramido-4-cyano-1-(2,3,4-trichlorophenyl)pyrazole (1.7 g), m.p. 117°–118° C., in the form of colourless crystals.

By proceeding in a similar manner but replacing the n-butyryl chloride by the hereinafter indicated acid chloride, there were obtained:

4-Cyano-5-isobutyramido-1-(2,3,4-trichlorophenyl)pyrazole, m.p. 159°–160° C., in the form of colourless crystals, after crystallisation from aqueous ethanol, from isobutyryl chloride.

4-Cyano-5-n-pentanamido-1-(2,3,4-trichlorophenyl)pyrazole, m.p. 127°–128° C., in the form of colourless crystals, after crystallisation from toluene, from n-valeryl chloride;

4-Cyano-5-(3-methylbutyramido)-1-(2,3,4-trichlorophenyl)pyrazole, m.p. 147°–148° C., in the form of colourless crystals, after crystallisation from toluene, from isovaleryl chloride; (±)4-Cyano-5-(2-methylbutyramido)-1-(2,3,4-trichlorophenyl)pyrazole, m.p. 186°–187° C., in the form of colourless crystals, after crystallisation from toluene, from (±)2-methylbutyryl chloride;

4-Cyano-5-n-heptanamido-1-(2,3,4-trichlorophenyl)pyrazole, m.p. 114°–116° C., in the form of colourless crystals, after crystallisation from toluene, from n-heptanoyl chloride.

By proceeding in a similar manner but replacing the n-butyryl chloride by the hereinafter indicated acid chloride and carrying out the addition of pyridine at 20° C. rather than 0° C., there were prepared:

4-Cyano-5-(2-ethylbutyramido)-1-(2,3,4-trichlorophenyl)pyrazole, m.p. 182°–183° C., in the form of yellow crystals, after crystallisation from a mixture of ethyl acetate and hexane (1:6 by volume), from 2-ethylbutyryl chloride;

4-Cyano-5-cyclopentylcarbonamido-1-(2,3,4-trichlorophenyl)pyrazole, m.p. 168°–170° C., in the form of colourless crystals, after crystallisation from toluene, from cyclopentylcarbonyl chloride;

4-Cyano-5-cyclopropylcarbonamido-1-(2,3,4-trichlorophenyl)pyrazole, m.p. 219°–221° C., in the form of colourless crystals, after crystallisation from toluene, from cyclopropylcarbonyl chloride;

(±)-4-Cyano-5-(2-ethylhexanamido)-1-(2,3,4-trichlorophenyl)pyrazole, m.p. 128.5° C., in the form of colourless crystals after crystallisation from a mixture of diethyl ether and hexane, from (±)-2-ethylhexanoyl chloride.

By proceeding in a similar manner but replacing the n-butyryl chloride by the hereinafter indicated acid chloride and stirring the reaction mixture at its reflux temperature, there was prepared:

4-Cyano-5-(2,2-dimethylpropionamido)-1-(2,3,4-trichlorophenyl)pyrazole, m.p. 210°–211° C., in the form of colourless crystals, after crystallisation from toluene, from trimethylacetyl chloride.

By proceeding in a similar manner but replacing the n-butyryl chloride with propionyl chloride and the 5-amino-4-cyano-1-(2,3,4-trichlorophenyl)pyrazole by the hereinafter indicated appropriately substituted phenyl pyrazole there were prepared:

4-Cyano-5-propionamido-1-(2,3,5,6-tetrafluoro-4-trifluoromethylphenyl)pyrazole, m.p. 114°–116° C., in the form of colourless crystals, from 5-amino-4-cyano-1-(2,3,5,6-tetrafluoro-4-trifluoromethylphenyl)pyrazole;

1-(2-Chloro-4-ethylphenyl)-4-cyano-5-propionamidopyrazole, m.p. 110°–111.5° C., in the form of colourless crystals, after crystallisation from toluene, from 5-amino-1-(2-chloro-4-ethylphenyl)-4-cyanopyrazole.

EXAMPLE 25

Compound 31

5-Amino-4-cyano-1-(2,3,4,6-tetrachlorophenyl)pyrazole (7.1 g) in propionyl chloride (40 ml) was heated at reflux for 16 hours. The reaction mixture was evaporated to dryness and the residue was dissolved in ethanol (250 ml), basified with saturated aqueous potassium bicarbonate solution (50 ml) and heated at reflux for 2 hours. The solution was evaporated to dryness and dissolved in a mixture of dichloromethane (250 ml) and water (250 ml). The organic layer was separated, washed once with water (250 ml), dried over anhydrous magnesium sulphate and evaporated to dryness to give a red gum (8.0 g), which was crystallised from toluene (25 ml) to give 4-cyano-5-propionamido-1-(2,3,4,6-tetrachlorophenyl)pyrazole (2.5 g), m.p. 203°–204° C., in the form of colourless crystals.

EXAMPLE 26

Compound 32

5-Amino-4-cyano-1-(2,3,4-trichlorophenyl)pyrazole (2.9 g) was added to a stirred solution of acetic anhydride (10 ml) and formic acid (10 ml) at laboratory temperature. The stirring was continued for 6 hours.

The reaction mixture was then allowed to stand at room temperature for 64 hours and was then diluted with diethyl ether. The solution was filtered, washed once with water, dried over anhydrous sodium sulphate and evaporated to give a gum (1.0 g). The gum was chromatographed on a silica column (3×30 cm) eluated with a mixture of dichloromethane and gradually increasing amounts (from 0 to 100% by volume) of ethyl acetate.

Evaporation of first 1000 ml of eluate gave unreacted 5-amino-4-cyano-1-(2,3,4-trichlorophenyl)pyrazole (0.13 g).

Evaporation of the next 500 ml of eluate gave a solid which was triturated with toluene to give 4-cyano-5-formamido-1-(2,3,4-trichlorophenyl)pyrazole (0.34 g), m.p. 190°-192° C., in the form of colourless crystals.

EXAMPLE 27

Compounds 4, 82, 83 and 159

Phenyl chloroformate (141 g) was added to a stirred suspension of 5-amino-4-cyano-1-(2,3,4-trichlorophenyl)pyrazole (86.3 g) in chloroform (600 ml) at −5° C. to −3° C. A solution of pyridine (71 g) in chloroform (100 ml) was added with stirring at 0° C. to 5° C. maintained by external cooling. The reaction mixture was then stirred at laboratory temperature for 16 hours. The reaction mixture was then filtered and the solid product washed with chloroform to give 4-cyano-5-di(phenoxycarbonyl)amino-1-(2,3,4-trichlorophenyl)pyrazole (135.6 g), m.p. 205.5°-206.5° C., in the form of a colourless solid.

By proceeding in a similar manner but replacing the 5-amino-4-cyano-1-(2,3,4-trichlorophenyl)pyrazole by the hereinafter indicated appropriately substituted phenylpyrazole there were obtained: 4-Cyano-5-di(phenoxycarbonyl)amino-1-(2,3,5,6-tetrafluoro-4-trifluoromethylphenyl)pyrazole, m.p. 233°-235° C., after crystallization from a mixture of ethylacetate-acetonitrile, in the form of colourless crystals, from 5-amino-4-cyano-1-(2,3,5,6-tetrafluoro-4-trifluoromethylphenyl)pyrazole. 1-(2-Chloro-4-trifluoromethylphenyl)-4-cyano-5-di(-phenoxycarbonyl)aminopyrazole, m.p. 156°-158° C., after crystallization from toluene, in the form of colourless crystals, from 5-amino-1-(2-chloro-4-trifluoromethylphenyl)-4-cyanopyrazole;

4-Cyano-1-(2,6-dichloro-4-trifluoromethylphenyl)-5-di(phenoxycarbonyl)aminopyrazole, 190°-192° C., after crystallisation from a mixture of ethyl acetate and hexane, in the form of colourless crystals, from 5-amino-4-cyano-1-(2,6-dichloro-4-trifluoromethylphenyl)-pyrazole.

EXAMPLE 28

Compounds 84, 91, 85, 86, 69, 140, 165, 160, 102, 103, 129, 145, 146, 157, 132, 147, 170, 158, 131, 133, 134, 139, 136, 166, 172, 174, 182, 180, 183, 188 and 189

Acetyl chloride (11.5 ml) was added to a stirred suspension of 5-amino-1-(2-chloro-4-n-propylphenyl)-4-cyanopyrazole (3.02 g) in chloroform (25 ml) at 0° C. A solution of pyridine (1.85 ml) in cloroform (5 ml) was then added to the reaction mixture at 0°-5° C. The reaction mixture was then warmed to laboratory temperature and allowed to stand overnight. The solution was then diluted with dichloromethane (50 ml) and washed with hydrochloric acid (2N; 50 ml) and twice with water (2×50 ml) and dried over anhydrous magnesium sulphate and evaporated to give a solid. This solid was chromatographed on a silica (Merck, 230-400 mesh; pressure 25 lb in$^{-2}$) eluted with dichloromethane and gradually increasing amounts of ethyl acetate (from 0 to 10% by volume). Evaporation of the eluate containing the faster moving component gave 1-(2-chloro-4-n-propylphenyl)-4-cyano-5-diacetylaminopyrazole (1.08 g), m.p. 110°-112° C., in the form of colourless crystals. Evaporation of the eluate containing the slower moving component gave 5-acetamido-1-(2-chloro-4-n-propylphenyl)-4-cyanopyrazole (0.86 g), m.p. 143°-144° C., after crystallisation from ethanol, in the form of a colourless solid.

By proceeding in a similar manner but replacing the 5-amino-1-(2-chloro-4-n-propylphenyl)-4-cyanopyrazole by the hereinafter appropriately substituted phenylpyrazole, there were obtained:

4-Cyano-5-diacetylamino-1-(2,6-dibromo-4-trifluoromethylphenyl)-pyrazole, m.p. 164°-165° C., in the form of colourless crystals, and 5-acetamido-4-cyano-1-(2,6-dibromo-4-trifluoromethylphenyl) pyrazole, m.p. 229°-230° C., in the form of colourless crystals, following chromatography using diethyl ether and hexane mixture (1:1 v/v) as eluant, from 5-amino-4-cyano-1-(2,6-dibromo-4-trifluoromethylphenyl)-pyrazole.

4-Cyano-5-diacetylamino-1-(4-ethyl-2,3,5,6-tetrafluorophenyl)pyrazole m.p. 112.5°-113.5° C. in the form of a colourless solid, following chromatography using hexanediethyl ether (1:1) as eluent, from 5-amino-4-cyano-1-(4-ethyl-2,3,5,6-tetrafluorophenyl)pyrazole.

1-(2-Chloro-4-isopropylphenyl)-4-cyano-5-diacetylaminopyrazole, m.p. 99°-101° C., in the form of a colourless crystalline solid, following chromatography using dichloromethane as eluent, from 5-amino-1-(2-chloro-4-isopropylphenyl)-4-cyanopyrazole.

1-(2-Bromo-4-trifluoromethylphenyl)-4-cyano-5-diacetylamino-pyrazole, m.p. 127°-128° C., in the form of colourless crystals, and 5-acetamido-1-(2-bromo-4-trifluoromethylphenyl)-4-cyanopyrazole, m.p. 186°-187° C., after crystallisation from a mixture of diethyl ether and hexane (1:1), in the form of colourless crystals, following chromatography using dichloromethane containing gradually increasing amounts of diethyl ether (0–100%), from 5-amino-1-(2-bromo-4-trifluoromethylphenyl)-4-cyanopyrazole.

By processing in a similar manner but replacing the substituted phenylpyrazole and/or the acetyl chloride there were prepared the following:

| Compound No. | Acid halide in place of acetyl chloride | Substituted phenylpyrazole in place of 5-amino-1-(2-chloro-4-n-propylphenyl)-4-cyanopyrazole | Form | Observations |
| --- | --- | --- | --- | --- |
| 102 | dichloroacetyl chloride | 5-amino-4-cyano-1-(2,6-dichloro-4-trifluoromethylphenyl)-pyrazole | Colourless solid m.p. 171-172° C. | Recrystallisation from ethyl acetate hexane |
| 103 | dichloroacetyl | 5-amino-1-(2-chloro-4- | Colourless solid | |

-continued

| Compound No. | Acid halide in place of acetyl chloride | Substituted phenylpyrazole in place of 5-amino-1-(2-chloro-4-n-propylphenyl)-4-cyanopyrazole | Form | Observations |
|---|---|---|---|---|
| | chloride | trifluoromethylphenyl)-4-cyanopyrazole | m.p. 176–177° C. | |
| 129 | succinyl chloride | 5-amino-4-cyano-1-(2,3,4-trichlorophenyl)pyrazole | Pale yellow crystals m.p. 206–208° C. | Chloroform Chromatography |
| 145 | succinyl chloride | 5-amino-4-cyano-1-(2,6-dichloro-4-trifluoromethyl-phenyl)pyrazole | light brown crystals m.p. 240–242° C. | Recrystallisation from toluene |
| 146 | succinyl chloride | 5-amino-1-(2-chloro-4-trifluoro-methylphenyl)-4-cyanopyrazole | Colourless crystals m.p. 172–173° C. | Dichloromethane Chromatography, recrystallisation from ethyl acetate - petroleum ether b.p. 60–80° C. |
| 157 | (±)methylsuccinyl chloride | 5-amino-4-cyano-1-(2,3,4-trichlorophenyl)pyrazole | Colourless crystals m.p. 176–177° C. | Recrystallisation from toluene - petroleum ether (b.p. 60–80° C.) |
| 132 | glutaryl chloride | 5-amino-4-cyano-1-(2,3,4-trichlorophenyl)pyrazole | Colourless needles m.p. 203–205° C. | Recrystallisation from ethyl acetate - hexane |
| 147 | glutaryl chloride | 5-amino-4-cyano-1-(2,6-dichloro-4-trifluoromethyl-phenyl)pyrazole | Fine white powder m.p. 184–186° C. | Chromatography using 99:1 dichloromethane - ethyl acetate as eluant |
| 170 | 4-ethoxycarbonylbutyryl chloride | 5-amino-4-cyano-1-(2,6-dichloro-4-trifluoromethyl-phenyl)pyrazole | Colourless powder m.p. 144–145° C. | |
| 158 | glutaryl chloride | 5-amino-1-(2-chloro-4-trifluoromethylphenyl)-4-cyanopyrazole | Colourless crystals m.p. 155–156° C. | Recrystallisation from toluene - petroleum ether (b.p. 60–80° C.) for '170' and '158' |
| 131 | butyryl chloride | 5-amino-4-cyano-1-(2,3,4-trichlorophenyl)-pyrazole | Colourless crystals m.p. 90–92° C. | |
| 133 | valeryl chloride | 5-amino-4-cyano-1-(2,3,4-trichlorophenyl)-pyrazole | Colourless crystals m.p. 97–99° C. | Chromatography using dichloromethane as eluant |
| 134 | isovaleryl chloride | 5-amino-4-cyano-1-(2,3,4-trichlorophenyl)-pyrazole | Colourless solid m.p. 82–84° C. | Recrystallisation from toluene - petroleum ether (b.p. 60–80° C.) |
| 139 | isobutyryl chloride | 5-amino-4-cyano-1-(2,3,4-trichlorophenyl)-pyrazole | Colourless crystals m.p. 98–100° C. | Chromatography using dichloromethane as eluant Recrystallisation from petroleum ether (b.p. 60–80° C.) |
| 136 | heptanoyl chloride | 5-amino-4-cyano-1-(2,3,4-trichlorophenyl)-pyrazole | Colourless crystals m.p. 43–44° C. | |
| 166 | isovaleryl chloride | 5-amino-1-(2-chloro-4-trifluoromethylphenyl)-4-cyanopyrazole | off-white solid m.p. 55–56° C. | Dichloromethane chromatograph Reaction at reflux temperature |
| 174, 172 | acetyl chloride | 5-amino-1-(4-sec-butyl-2,3,5,6-tetrafluoromethyl-phenyl)-4-cyanopyrazole | Colourless solid m.p. 97–99° C. Colourless solid m.p. 101.5–103.5° C. | Chromatography using 1:1 diethyl ether - hexane as eluant |
| 182, 180 | acetyl chloride | 5-amino-4-cyano-1-(2,3-dichloro-4-methylphenyl)-pyrazole (described in GB 2,070,604 A) | Colourless solid m.p. 146–148° C. Colourless solid m.p. 198–200° C. | Crystallisation from toluene |
| 183 | isovaleryl chloride | 5-amino-4-cyano-1-(2,3,5,6-tatrafluoro-4-trifluoromethylphenyl)-pyrazole | Off-white solid m.p. 64–65° C. | Chromatography using dichloro-methane-petroleum ether (b.p. 60–80° C.) 1:1 as eluant |
| 188 | 2,2-dimethyl-succinyl chloride | 5-amino-4-cyano-1-(2,3,4-trichloro-phenyl)pyrazole | Colourless crystals m.p. 162–163° C. | Recrystallisation from ethyl acetate-petroleum ether (b.p. 60–80° C.) |
| 189 | isovaleryl chloride | 5-amino-4-cyano-2,6-dichloro-4-trifluoromethyl-phenyl)pyrazole | Colourless crystals m.p. 94–95° C. | Chromatography using dichloro-methane as eluant. Recrystallisation |

| Compound No. | Acid halide in place of acetyl chloride | Substituted phenylpyrazole in place of 5-amino-1-(2-chloro-4-n-propylphenyl)-4-cyanopyrazole | Form | Observations |
|---|---|---|---|---|
| | | | | from ethyl acetate-petroleum ether (60–80° C.) |

EXAMPLE 29

Compounds 46, 47, 48, 49, 50, 51, 90, 54, 55, 56, 109 and 124

A stirred mixture of 4-cyano-5-di(phenoxycarbonyl)amino-1-(2,3,4-trichlorophenyl)pyrazole (prepared as described in Example 27; 20 g) in 2-ethoxyethanol (400 ml) was heated at reflux for 4 hours. The reaction mixture was evaporated to dryness and the residue crystallized from ethyl acetate-n-hexane to give 4-cyano-5-[(2-ethoxy)ethoxycarbonylamino]-1-(2,3,4-trichlorophenyl)pyrazole (10 g), m.p. 122°–124° C., in the form of colourless crystals. The mother liquors were evaporated to dryness and the residue chromatographed on aluminium oxide (120 g; May & Baker grade) using dichloromethane as eluent. Evaporation of the eluate and crystallisation of the residue from ethyl acetate-n-hexane gave a further quantity of 4-cyano-[5-(2-ethoxy)ethoxycarbonylamino]-1-(2,3,4-trichlorophenyl)pyrazole (3 g).

By proceeding in a similar manner but replacing the 2-ethoxyethanol by the hereinafter indicated alcohol, there were prepared the following 4-cyano-5-alkoxycarbonylamino-1-(2,3,4-trichlorophenyl)pyrazoles identified by compound number:

| Compound No. | Alcohol in place of 2-ethoxyethanol | Form |
|---|---|---|
| 47 | methanol | Colourless crystals m.p. 205–206° C. |
| 48 | isopropanol | Colourless crystals m.p. 132–133° C. |
| 49 | n-butanol | Colourless crystals m.p. 125–127° C. |
| 50 | n-propanol | Colourless crystals m.p. 122–123° C. |
| 51 | ethanol | Colourless crystals m.p. 124–125° C. |
| 90 | isobutanol | Colourless crystals m.p. 109–110° C. |

By proceeding in a similar manner but replacing the 4-cyano-5-di(phenoxycarbonyl)amino-1-(2,3,4-trichlorophenyl) pyrazole by the appropriately substituted bis-phenylcarbamate, and replacing the 2-ethoxyethanol by the hereinafter indicated alcohol, there were prepared:

1-(2-Chloro-4-trifluoromethylphenyl)-4-cyano-5-methoxycarbonylaminopyrazole, m.p. 163°–164° C., after crystallisation from ethyl acetate-n-hexane, in the form of colourless crystals, from 1-(2-chloro-4-trifluoromethylphenyl)-4-cyano-5-di(phenoxycarbonyl)aminopyrazole (prepared as described in Example 27) and methanol.

4-Cyano-5-methoxycarbonylamino-1-(2,3,5,6-tetrafluoro-4-trifluoromethylphenyl)pyrazole, m.p. 114°–115° C., after crystallisation from n-hexane-diethyl ether, in the form of colourless crystals, from 4-cyano-di(phenoxycarbonyl)amino-1-(2,3,5,6-tetrafluoro-4-trifluoromethylphenyl)pyrazole and methanol.

4-Cyano-5-ethoxycarbonylamino-1-(2,3,5,6-tetrafluoro-4-trifluoromethylphenyl)pyrazole, m.p. 102°–103° C., after crystallisation from ethyl acetate-n-hexane, in the form of colourless crystals, from 4-cyano-5-di(phenoxycarbonyl)amino-1-(2,3,5,6-tetrafluoro-4-trifluoromethylphenyl)pyrazole and ethanol.

4-Cyano-1-(2,6-dichloro-4-trifluoromethylphenyl)-5-methoxycarbonylaminopyrazole, m.p. 149°–150° C., after crystallisation from a mixture of diethyl ether and hexane, in the form of colourless crystals, from methanol. 4-Cyano-5-isopropoxycarbonylamino-1-(2,3,5,6-tetrafluoro-4-trifluoromethylphenyl)pyrazole, m.p. 106°–107° C., after crystallisation from a mixture of ethyl acetate and hexane in the form of colourless crystals, from isopropanol.

EXAMPLE 30

Compound 52

Sodium (0.5 g) was added to a stirred mixture of 4-cyano-5-di(phenoxycarbonyl)amino-1-(2,3,4-trichlorophenyl)pyrazole (prepared as described in Example 27; 25 g) in t-butanol (400 ml) and the mixture was heated at reflux for 15 minutes. Solid carbon dioxide pellets were then added to the cooled reaction mixture to adjust the pH to 7. The neutralized reaction mixture was filtered and the filtrate evaporated under reduced pressure to give an oil which was crystallised from ethyl acetate-n-hexane to give 5-t-butoxycarbonylamino-4-cyano-1-(2,3,4-trichlorophenyl)pyrazole (11.0 g), m.p. 140°–141° C., in the form of colourless crystals.

EXAMPLE 31

Compound 53

A solution of sodium 2-propenyloxide in allyl alcohol [30 ml; prepared by dissolving sodium metal (1.0 g) in allyl alcohol (40 ml)] was added to a stirred solution of 4-cyano-5-di(phenoxycarbonyl)amino-1-(2,3,4-trichlorophenyl)pyrazole (15 g) in tetrahydrofuran (300 ml). The mixture was stirred for 15 minutes at laboratory temperature then solid carbon dioxide pellets added to adjust the pH of the solution to pH7. The neutralized solution was filtered through diatomaceous earth and then evaporated under reduced pressure and the residue crystallised from a mixture of ethyl acetate and hexane to give 4-cyano-5-(2-propenyloxycarbonylamino)-1-(2,3,4-trichlorophenyl)pyrazole, m.p. 154°–155° C., in the form of colourless crystals.

EXAMPLE 32

Compound 47

A solution of methyl chloroformate (0.4 g) in acetonitrile (5 ml) was added to a stirred mixture of 5-amino-4-cyano-1-(2,3,4-trichlorophenyl)pyrazole (1 g) and sodium carbonate (0.5 g) in acetonitrile (10 ml) at laboratory temperature. After 72 hours the reaction mixture was filtered and the filtrate evaporated to give a yellow solid. The solid was chromatographed on a silica column (Merck 230–400 mesh; pressure 25 lb in$^{-2}$) eluted with dichloromethane-ethyl acetate (19:1). Evaporation of the eluate containing the faster moving component gave 4-cyano-5-methoxycarbonylamino-1-(2,3,4-trichlorophenyl)(0.12 g), m.p. 204°–205° C., after crystallisation from ethyl acetate-n-hexane, in the form of colourless crystals.

EXAMPLE 33

Compounds 57, 58, 59, 60, 130, 150, 153, 169, 167 and 181

By proceeding in a similar manner to that hereinbefore described in Example 13 but replacing the substituted phenylpyrazole by the hereinafter indicated appropriately substituted phenylpyrazoles and chromatography on silica column (Merck 230–400 mesh; pressure 25 lb in$^{-2}$) using dichloromethane as eluent and with recrystallisation from toluene-petroleum ether (b.p. 60°–80° C.), there were prepared the following 4-cyano-5-diacetylamino-1-(sub.phenyl)pyrazoles identified by Compound number:

| Compound No | Substituted phenylpyrazole in place of 5-amino-4-cyano-1-(2,3,4-trichlorophenyl) pyrazole used in Example 13 | Form |
|---|---|---|
| 57 | 5-amino-4-cyano-1-(2,3,5,6-tetrafluoro-4-trifluoromethylphenyl)pyrazole | Colourless crystals m.p. 133–135° C. |
| 58 | 5-amino-1-(2-chloro-4-trifluoromethylphenyl)-4-cyanopyrazole | Colourless crystals m.p. 128–130° C. |
| 59 | 5-amino-4-cyano-1-(2,4,6-trichlorophenyl)pyrazole | Colourless crystals m.p. 130–131° C. |
| 60 | 5-amino-4-cyano-1-(2,4-dichlorophenyl)pyrazole | Colourless m.p. 113–114° C. [J. Hetero Chem 12, 1199–1205 (1975)] |
| 130 | 5-amino-4-cyano-1-(2,6-dichloro-4-trifluoromethylphenyl)pyrazole | Colourless crystals m.p. 103–105° C. |
| 150 | 5-amino-4-cyano-1-(2,4-dichloro-6-methylphenyl)pyrazole | Colourless crystals m.p. 119–120° C. |
| 153 | 5-amino-4-cyano-1-pentafluorophenylpyrazole (described in British Published Patent Specification No 2070604 A) | Colourless crystals m.p. 122–123° C. |
| 169 | 5-amino-4-cyano-1-(2-nitro-4-trifluoromethylphenyl)pyrazole (described in British Published Patent Specification No 2070604 A) | Pale yellow crystals m.p. 182–183° C. Recrystallisation from ethyl acetate-petroleum ether (b.p. 60–80° C.) |
| 167 | 5-amino-1-(4-chloro-2,3,5,6-tetrafluorophenyl)pyrazole | Colourless crystals m.p. 144–146° C. |
| 181 | 5-amino-4-cyano-1-(2,3,4,6-tetrachlorophenyl)pyrazole | Colourless crystals m.p. 130–132° C. |

EXAMPLE 34

Compounds 35, 37, 36, 66, 67, 70, 71, 72, 65, 88, 114, 128, 116, 173, 178 and 179

By proceeding in a similar manner to that hereinbefore described in Example 22 but replacing the substituted phenylpyrazole by the appropriate phenylpyrazole substituted as hereinafter indicated, there were prepared the following 5-acetamido-4-cyano-1-(Sub.-phenyl)pyrazoles identified by Compound number:

| Compound No. | Phenyl substitution in place of 5-amino-1-(2-chloro-4-methylphenyl)4-cyanopyrazole used in Example 22 | Form | Observations on recrystallisation |
|---|---|---|---|
| 35 | 4-methyl-2,3,6-trichloro | Fawn-coloured crystals m.p. 171–173° C. | toluene |
| 37 | 2-chloro-4-isopropyl | Cream-coloured crystals m.p. 133–134° C. | — |
| 36 | 2,3-dichloro-4-ethyl | Cream-coloured crystals m.p. 175–176.5° C. | toluene |
| 66 | 4-n-butyl-2,3,5,6-tetrafluoro | Colourless solid m.p. 128–129° C. | — |
| 67 | 4-ethyl-2,3,5,6-tetrafluoro | Colourless crystals m.p. 138.5–140° C. | ethanol-water |
| 70 | 4-bromo-2,3-dichloro | Off-white | toluene |

-continued

| Compound No. | Phenyl substitution in place of 5-amino-1-(2-chloro-4-methylphenyl)4-cyanopyrazole used in Example 22 | Form | Observations on recrystallisation |
|---|---|---|---|
|  | [described in GB 2070604A] | solid m.p. 225–228° C. |  |
| 71 | 2-nitro-4-trifluoromethyl [described in GB 2070604A] | Pale yellow solid m.p. 220–222° C. | — |
| 72 | 2,6-dichloro-4-trifluoromethyl | Colourless crystals m.p. 207–208.5° C. | toluene |
| 74 | pentafluoro [described in GB 2070604A] | Off-white solid m.p. 201–203° C. | toluene |
| 65 | 2-chloro-4-trifluoromethyl | Colourless crystals m.p. 191–193° C. | ethanol-water |
| 88 | 2,3,4,6-tetrafluoro [described in GB 2070604A] | Pale green solid m.p. 215–217° C. | toluene |
| 114 | 2,4-dichloro-6-methyl | Colourless crystals m.p. 168–170° C. | toluene-hexane |
| 128 | 2,6-dichloro-4-ethyl | Colourless crystals m.p. 158–160° C. | toluene |
| 116 | 4-chloro-2,3,5,6-tetrafluoro | Colourless solid m.p. 206–208° C. | toluene-hexane |
| 173 | 2,3,5,6-tetrafluoro-4-vinyl | Pale yellow solid m.p. 149.5–151.5° C. | aqueous ethanol |
| 178 | 3,5-difluoro-2,4,6-trichloro | Colourless crystals m.p. 226–228° C. | toluene |
| 179 | 4-bromo-2,3,5,6-tetrafluoro | Colourless crystals m.p. 218–220° C. | toluene |

EXAMPLE 35

Compounds 68, 73, 38, 39, 40, 75, 76, 81, 115, 117, 118 163, 175, 176 and 171

By proceeding in a similar manner to that hereinbefore described in Example 22 but replacing the acetyl chloride by propionyl chloride and the substituted phenylpyrazole by the appropriate phenylpyrazole substituted as hereinafter indicated, there were prepared the following 5-propionamido-4-cyano-1-(sub.phenyl)-pyrazoles identified by Compound number:

| Compound No | Phenyl substitution in place of 5-amino-1-(2-chloro-4-methylphenyl)-4-cyanopyrazole used in Example 22 | Form | Observations |
|---|---|---|---|
| 68 | 4-methyl-2,3,5,6-tetrafluoro | Colourless crystals m.p. 148.5–150° C. | ethanol-water |
| 73 | 2,6-dichloro-4-trifluoromethyl | Colourless crystals m.p. 179–180.5° C. | toluene |
| 38 | — | Fawn-coloured crystals m.p. 138–139° C. | toluene |
| 39 | 2-chloro-4-isopropyl | Cream-coloured solid m.p. 120–122° C. | — |
| 40 | 2,3,6-trichloro-4-trifluoromethyl | Colourless crystalline solid m.p. 181–182° C. | — |
| 75 | 2,4,6-trichloro | Colourless crystals m.p. 161–163° C. | toluene-hexane |
| 76 | 2,4-dichloro [J. Heter. Chem. 12 1199–1205 (1975)] | Colourless crystals m.p. 156–158° C. | toluene |
| 81 | 2,3-dichloro | Colourless solid m.p. 174–175° C. | toluene |

-continued

| Compound No | Phenyl substitution in place of 5-amino-1-(2-chloro-4-methylphenyl)-4-cyanopyrazole used in Example 22 | Form | Observations |
|---|---|---|---|
| 115 | 2,4-dichloro-6-methyl | Colourless solid m.p. 163–165° C. | toluene-hexane |
| 117 | 4-chloro-2,3,5,6-tetrafluoro | Colourless solid m.p. 158–160° C. | toluene-hexane |
| 118 | 2,3,4,6-tetrafluoro (described in GB 2070604 A) | Off-white solid m.p. 193–195° C. | toluene |
| 163 | 4-n-butyl-2,3,5,6-tetrafluoro | Oil | Chromatography on a silica column (Merck 230–400 mesh; 10 lb in$^{-2}$) using 1:1 diethyl ether-hexane as eluant. |
| 175 | 2-chloro-4-n-propyl | Colourless solid m.p. 101–103° C. | |
| 176 | 4-sec-butyl-2,3,5,6-tetrafluoro | Colourless solid m.p. 96.5–98.5° C. | |
| 171 | 4-methyl-2,3,6-trichloro | Colourless crystals m.p. 150–151° C. | toluene |

EXAMPLE 36

By proceeding in a similar manner to that hereinbefore described in Example 22 but replacing the acetyl chloride by isobutyryl chloride and the substituted phenylpyrazole by 5-amino-1-(2-chloro-4-trifluoromethylphenyl)4-cyanopyrazole, there was prepared:

| Compound No. | Phenyl substitution in place of 5-amino-1-(2-chloro-4-methylphenyl)-4-cyanopyrazole used in Example 22 | Form | Observations |
|---|---|---|---|
| 77 | 2-chloro-4-trifluoromethyl | Colourless solid m.p. 169–171° C. | reaction at 20° C. rather than 0° C. |

EXAMPLE 37

Compounds 78, 79, 45, 34 and 113

By proceeding in a similar manner to that hereinbefore described in Example 24 but replacing the n-butyryl chloride by the hereinafter indicated acid halide, there were prepared the following 4-cyano-5-(sub.carbonamido)-1-(2,3,4-trichlorophenyl)pyrazoles identified by Compound number:

| Compound No. | Acid halide in place of n-butyryl chloride used in Example 24 | Form | Observations |
|---|---|---|---|
| 78 | dichloroacetyl chloride | Colourless crystals m.p. 159–160° C. | Addition of pyridine at 20° C. rather than 0° C. Recrystallisation from toluene |
| 79 | cyclobutylcarbonyl chloride | Colourless crystals m.p. ¾-186° C. | Addition of pyridine at 20° C. rather than 0° C. Recrystallisation from ethyl acetate |
| 45 | cyclohexylcarbonyl chloride | Colourless crystals m.p. 149–151° C. | Addition of pyridine at 20° C. rather than 0° C. |
| 34 | (±)-2-ethyl-3-methyl-butyryl chloride | Colourless crystals m.p. 155–156° C. | Recrystallisation from toluene - petroleum ether (b.p. 80–100° C.) Stirring at reflux. Recrystallisation from toluene |
| 113 | (±)-2-methyl-pentanoyl chloride | Orange powder m.p. 134–136° C. | Stirring at reflux. Recrystallisation from toluene-hexane |

EXAMPLE 38

Compounds 41, 42, 43, 44, 89 and 186

By proceeding in a similar manner to that hereinbefore described in Example 24 but replacing the n-butyryl chloride by the hereinafter indicated acid halide and the substituted phenylpyrazole by 5-amino-1-(2,3,5,6-tetrafluoro-4-trifluoromethylphenyl)-4-cyano-pyrazole, there were prepared the following 4-cyano-5-(sub. carbonamido)-1-(2,3,5,6-tetrafluoro-4-trifluoromethylphenyl)-pyrazoles identified by Compound number:

| Compound No. | Acid halide in place of n-butyryl chloride used in Example 24 | Form | Observations |
|---|---|---|---|
| 41 | — | Colourless crystals m.p. 99–101° C. | Addition of pyridine at 20° C. rather than 0° C. Recrystallisation from cyclohexane |
| 42 | isobutyryl chloride | Colourless crystals m.p. 149–151° C. | |
| 43 | cyclopropylcarbonyl chloride | Colourless crystals m.p. 148–149° C. | Addition of pyridine at 20° C. rather than 0° C. Recrystallisation from toluene |
| 44 | 2-ethylbutyryl chloride | Colourless crystals m.p. 138–139° C. | |
| 89 | isovaleryl chloride | Colourless crystals m.p. 148–150° C. | Stirring at reflux. Recrystallisation from toluene |
| 186 | (±)-cis,trans-2-methylcyclopropylcarbonyl chloride | Colourless crystals m.p. 220–222° C. | Stirring at reflux Recrystallisation from ethyl acetate-petroleum ether (b.p. 60–80° C.) |

EXAMPLE 39

Compounds 92, 93, 96, 106, 111, 87, 99, 121, 61, 62, 63, 64, 126, 127 and 184

By proceeding in a similar manner to that hereinbefore described in Example 24 but replacing the n-butyryl chloride by the hereinafter indicated acid halide and the substituted phenylpyrazole by 5-amino-1-(2-chloro-4-trifluoromethylphenyl)-4-cyanopyrazole, there were prepared the following 4-cyano-5-(sub.carbonamido)-1-(2-chloro-4-trifluoromethylphenyl)pyrazoles identified by Compound number:

| Compound No. | Acid halide in place of n-butyryl chloride used in Example 24 | Form | Observations |
|---|---|---|---|
| 92 | cyclohexycarbonyl chloride | Colourless solid m.p. 160–161° C. | |
| 93 | (±)2-methylbutyryl chloride | Colourless crystals m.p. 132–133° C. | |
| 96 | pivaloyl chloride | Colourless crystals m.p. 190–192° C. | Addition of pyridine at 20° C. rather than 0° C. Recrystallisation from ethyl acetate - petroleum ether (b.p. 60–80° C.) |
| 106 | heptanoyl chloride | Colourless crystals m.p. 88–89° C. | |
| 111 | cyclopentylcarbonyl chloride | Buff-coloured crystals m.p. 119–120° C. | |
| 87 | Valeryl chloride | Colourless crystals m.p. 87–89° C. | |
| 99 | 2-ethylbutyryl chloride | Colourless crystals m.p. 165–166° C. | Reaction at reflux temperature. Acetonitrile as solvent. Recrystallisation from ethyl acetate - petroleum ether (b.p. 60–80° C.) |
| 121 | cyclobutylcarbonyl chloride | Colourless crystals m.p. 161–162° C. | |
| 61 | propionyl chloride | Colourless crystals m.p. 154–156° C. | Addition of pyridine at 20° C. rather than 0° C. Recrystallisation from toluene |
| 62 | — | Colourless crystals m.p. 135–137° C. | Addition of pyridine at 20° C. rather than 0° C. Recrystallisation from ethyl acetate-petroleum ether (b.p. 60–80° C.) |
| 63 | isovaleryl chloride | Colourless crystals m.p. 108–109° C. | |
| 64 | cyclopropylcarbonyl chloride | Colourless crystals m.p. 156–158° C. | Addition of pyridine at 20° C. rather than 0° C. Recrystallisation from toluene |

-continued

| Compound No. | Acid halide in place of n-butyryl chloride used in Example 24 | Form | Observations |
|---|---|---|---|
| 126 | (±)2-methylpentanoyl chloride | Colourless crystals m.p. 99–101° C. | Reaction at reflux temperature Recrystallisation from toluene-hexane |
| 127 | (±)-2-ethyl-3-methylbutyryl chloride | Colourless crystals m.p. 172–174° C. | Reaction at reflux temperature. Recrystallisation from ethyl acetate - petroleum ether (b.p. 60–80° C.) |
| 184 | (±)-cis,trans-2-methylcyclo-propylcarbonyl chloride | Colourless crystals m.p. 130–132° C. | Reaction at reflux temperature. Column chromatography ether-hexane (1:1) as eluent |

EXAMPLE 40

Compounds 98, 112, 119, 104, 105, 110, 120, 123, 164, 162, 95, 97, 107, 108 and 187

By proceeding in a similar manner to that hereinbefore described in Example 24 but replacing the n-butyryl chloride by the hereinafter indicated acid halide and the substituted phenylpyrazole by 5-amino-1-(2,6-dichloro-4-trifluoromethylphenyl)-4-cyanopyrazole, there were prepared the following 4-cyano-5-(sub.carbonamido)-1-(2,6-dichloro-4-trifluoromethylphenyl)-pyrazoles identified by Compound number:

| Compound No. | Acid halide in place of n-butyryl chloride used in Example 24 | Form | Observations |
|---|---|---|---|
| 98 | — | Colourless powder m.p. 168–170° C. | Reaction at reflux temperature. Recrystallisation from toluene |
| 112 | (±)2-methylbutyryl chloride | Colourless crystals m.p. 132–133° C. | Reaction at reflux temperature. Acetonitrile as solvent. Recrystallisation from ethyl acetate - petroleum ether (b.p. 60–80° C.) |
| 119 | cyclobutylcarbonyl chloride | Colourless crystals m.p. 199–200° C. | |
| 104 | isobutyryl chloride | Colourless solid m.p. 172–173° C. | Reaction at reflux temperature Recrystallisation from toluene |
| 105 | cyclopropylcarbonyl chloride | Colourless solid m.p. 203–205° C. | |
| 110 | valeryl chloride | Colourless crystals m.p. 135–137° C. | |
| 120 | pivaloyl chloride | Colourless crystals m.p. 200–201° C. | Reaction at reflux temperature Recrystallisation from ethyl acetate - petroleum ether (b.p. 60–80° C.) |
| 123 | 2-ethylbutyryl chloride | Buff-coloured crystals m.p. 175–176° C. | |
| 164 | (±)2-ethyl-3-methylbutyryl chloride | Buff-coloured crystals m.p. 195–196° C. | |
| 162 | (±)-2-methylpentanoyl chloride | Pale yellow crystals m.p. 131–135° C. | Reaction at reflux temperature. Dichloromethane chromatography |
| 95 | cyclohexylcarbonyl chloride | Colourless crystals m.p. 182–184° C. | Addition of pyridine at 20° C. rather than 0° C. Recrystallisation from ethyl acetate-petroleum ether (b.p. 60–80° C.) |
| 97 | isovaleryl chloride | Colourless solid m.p. 178–179° C. | |
| 107 | cyclopentylcarbonyl chloride | Colourless crystals m.p. 195–196° C. | |
| 108 | heptanoyl chloride | Colourless crystals m.p. 111–112° C. | |
| 187 | (±)-cis,trans-2-methylcyclopropyl-carbonyl chloride | Colourless crystals m.p. 189–190° C. | Reaction at reflux temperature using acetonitrile as solvent. Recrystallisation from ethyl acetate-petroleum ether |

-continued

| Compound No. | Acid halide in place of n-butyryl chloride used in Example 24 | Form | Observations |
|---|---|---|---|
| | | | (b.p. 60–80° C.) |

EXAMPLE 41

Compounds 100, 122 and 177

By proceeding in a similar manner to that hereinbefore described in Example 24 but replacing the substituted phenyl pyrazole by the hereinafter indicated appropriate substituted phenylpyrazole, there were prepared the following compounds:

4-Cyano-1-(2,6-dibromo-4-trifluoromethylphenyl)-5-propionamidopyrazole, m.p. 160°–161° C., in the form of colourless crystals, from 5-amino-4-cyano-1-(2,6-dibromo-4-trifluoromethylphenyl)pyrazole.

4-Cyano-1-(2,nitro-4-trifluoromethylphenyl)-5-propionamidopyrazole, m.p. 162°–163° C., after crystallisation from a mixture of ethyl acetate and petroleum ether (bp 60°–80° C.), from 5-amino-4-cyano-1-(2-nitro-4-trifluoromethylphenyl)pyrazole (described in British Published Patent Specification No. 2,070,604A).

4-Cyano-1-(2,3-dichloro-4-methylphenyl)-5-propionamidopyrazole, m.p. 173°–174° C., after crystallisation from toluene, in the form of colourless crystals, from 5-amino-4-cyano-1-(2,3-dichloro-4-methylphenyl)pyrazole (described in Published British Patent Specification No. 2,070,604A).

EXAMPLE 42

Compounds 135, 137, 138, 141, 142, 151, 148, 149, 143, 144, 155, 168 and 156

Sodium hydride (480 mg; 50% dispersion in oil) was added in portions over 5 minutes to a stirred solution of 5-acetamido-4-cyano-1-(2,3,4-trichlorophenyl)pyrazole (3.3 g) in dry dimethylformamide (20 ml), under nitrogen, at a temperature of −10° C. to 0° C. The stirring was continued at 0° C. for 1.5 hours after which time evolution of hydrogen had ceased. A solution of propionyl chloride (1.01 g) in dry dimethylformamide (10 ml) was added to the reaction mixture over 10 minutes at a temperature of 0° C. The reaction mixture was stirred at 5° C. overnight, then poured onto a mixture of ice and dilute hydrochloric acid, to precipitate a white solid. The solid was filtered off, washed with water and dissolved in dichloromethane, the dichloromethane solution was dried over anhydrous magnesium sulphate and evaporated to give an oil (3.7 g). The oil was chromatographed on a silica column (Merck 230–400 mesh; pressure 10 lb in$^{-2}$) using dichloromethane as eluent. Evaporation of the eluate containing the major component gave a solid (2.7 g) which was crystallised from a mixture of toluene and petroleum ether (bp 60°–80° C.) to give 5-(N-acetyl-N-propionyl)amino-1-(2,3,4-trichlorophenyl)pyrazole (1.8 g), m.p. 114°–115° C. in the form of colourless crystals.

By proceeding in a similar manner, there were prepared the following:

| Compound No | Chloride Reactant | Pyrazole Reactant |
|---|---|---|
| 137 | cyclopropylcarbonyl chloride reacted with | Compound 1 |
| 138 | 2-ethylbutyryl chloride | Compound 1 |
| 141 | heptanoyl chloride | Compound 1 |
| 142 | isobutyryl chloride | Compound 1 |
| 151 | valeryl chloride | Compound 1 |
| 148 | isobutyryl chloride | Compound 5 |
| 149 | propionyl chloride | Compound 65 |
| 143 | propionyl chloride | Compound 61 |
| 144 | propionyl chloride | Compound 73 |
| 155 | acetyl chloride | Compound 47 |
| 168 | isobutyryl chloride | Compound 47 |
| 156 | acetyl chloride | Compound 11 |

| Compound No. | Form | Observations |
|---|---|---|
| 137 | Colourless crystals m.p. 124–127° C. | Chromatography using dichloromethane as eluant |
| 138 | Colourless crystals m.p. 129–130° C. | Chromatography using 1:1 dichloromethane - petroleum ether (b.p. 60–80° C.) Recrystallisation from petroleum ether (b.p. 60–80° C.) |
| 141 | Colourless crystals m.p. 58–60° C. | Chromatography using dichloromethane as eluant |
| 142 | Colourless solid m.p. 124–125° C. | |
| 151 | Colourless solid m.p. 86–88° C. | Recrystallisation from petroleum ether (b.p. 60–80° C.) Chromatography using 2:1 dichloromethane - petroleum ether (b.p. 60–80° C.) |
| 148 | Colourless crystals m.p. 102–103° C. | Recrystallisation from toluene and petroleum ether |
| 149 | Colourless crystals m.p. 105–106° C. | Chromatography using dichloromethane as eluant |
| 143 | Cream coloured solid m.p. 119–120° C. | |
| 144 | Colourless crystals m.p. 101–102° C. | Ambient temperature. Tetrahydrofuran as solvent. Recrystallisation from toluene - hexane |
| 155 | Colourless crystals m.p. 148–150° C. | |
| 168 | Colourless crystals m.p. 114–115° C. | Tetrahydrafuran as solvent. Recrystallisation from ethyl acetate - hexane. |
| 156 | Off white crystals m.p. 103–105° C. | Recrystallisation from aqueous ethanol after reaction in tetrahydrofuran |

EXAMPLE 43

Compounds 154 and 152

A solution of 5-amino-4-cyano-1-(2,3,4,6-tetrafluorophenyl)pyrazole (2.6 g; described in British Published Patent Specification No. 2,070,604A.) in dry tetrahydrofuran (10 ml) was added dropwise to a stirred suspension of powdered sodium hydride (0.53 g) in dry tetrahydrofuran, under nitrogen, at a temperature not exceeding 30° C. maintained by external cooling (ice). When the evolution of hydrogen had ceased a solution of acetyl chloride (1.5 ml) in tetrahydrofuran (15 ml) was added at a temperature not exceeding 30° C. After stirring at laboratory temperature for 48 hours the reaction mixture was washed with saturated aqueous ammonium chloride and the organic layer separated and dried over anhydrous magnesium sulphate and evaporated to dryness. The residue was chromatographed on a silica column (Merck 230–400 mesh; 10 lb in$^{-2}$) using dichloromethane as eluent. Evaporation of the eluate containing the major component gave a solid which was crystallised from a mixture of toluene and hexane to give 4-cyano-5-diacetylamino-1-(2,3,4,6-tetrafluorophenyl)pyrazole (1.5 g), m.p. 132°–134° C., in the form of colourless crystals.

By proceeding in a similar manner but replacing the 5-amino-4-cyano-1-(2,3,4,6-tetrafluorophenyl)pyrazole with 5-amino-1-(4-n-butyl-2,3,5,6-tetrafluorophenyl)-4-cyanopyrazole, there was prepared:

1-(4-n-Butyl-2,3,5,6-tetrafluorophenyl)-4-cyano-5-diacetylaminopyrazole, m.p. 73.5°–75° C., in the form of a colourless solid, following chromatography using dichloromethane as eluent.

EXAMPLE 44

Compounds 125, 80, 94, 101 and 161

A mixture of 5-amino-4-cyano-1-(2,3,4-trichlorophenyl)pyrazole (11.44 g) and (±)-4-chloropentanoyl chloride (9.2 g) in dry acetonitrile (60 ml) was stirred and heated at reflux for 7 hours. The reaction mixture was evaporated under diminished pressure to give an oil. The oil was chromatographed on a silica column (Merck 230–400 mesh; pressure 25 lb in$^{-2}$) using dichloromethane as eluent. Evaporation of the eluate containing the major component gave a light brown oil (14.3 g). This oil was crystallised from a mixture of diethyl ether and petroleum ether (bp 60°–80° C.) to give (±)-5-(4-chloropentanamido)-4-cyano-1-(2,3,4-trichlorophenyl)pyrazole (9.0 g), m.p. 126°–127° C., in the form of colourless crystals.

By proceeding in a similar manner, but replacing the (±)-4-chloropentanoyl chloride by the hereinafter indicated acid chloride, there were prepared: 5-(4-Chlorobutyramido)-4-cyano-1-(2,3,4-trichlorophenyl)pyrazole, m.p. 173°–174° C. after crystallisation from toluene, in the form of pale yellow crystals, from 4-chlorobutyryl chloride.

5-(5-Chloropentanamido)-4-cyano-1-(2,3,4-trichlorophenyl)pyrazole, m.p. 139° C., after crystallisation from a mixture of ethyl acetate and hexane, in the form of colourless crystals, from 5-chloropentanoyl chloride.

5-(3-Chloro-2,2-dimethylpropionamido)-4-cyano-1-(2,3,4-trichlorophenyl)pyrazole, m.p. 169°–175° C., in the form of colourless crystals, from β-chloropivaloyl chloride.

By proceeding in a similar manner but replacing the 5-amino-4-cyano-1-(2,3,4-trichlorophenyl)pyrazole with 5-amino-1-(2-chloro-4-methylphenyl)-4-cyanopyrazole and the (±)-4-chloropentanoyl chloride by (±)-3-chlorobutyryl chloride there was prepared. (±)-1-(2-chloro-4-methylphenyl)-5-(3-chlorobutyramido)-4-cyanopyrazole, m.p. 195°–196° C., after crystallisation from aqueous acetone, in the form of a colourless solid.

EXAMPLE 45

Compound 185

By proceeding in a similar manner to that hereinbefore described in Example 24 but replacing the n-butyryl chloride with cyclopropylcarbonyl chloride and replacing the substituted phenylpyrazole by 5-amino-4-cyano-1-(2,3,4,6-tetrachlorophenyl)pyrazole and carrying out the addition of pyridine at laboratory temperature rather than 0° C. there was prepared.

4-Cyano-5-cyclopropylcarbonamido-1-(2,3,4,6-tetrachlorophenyl)pyrazole, m.p. 205°–207° C., after crystallisation from a mixture of ethyl acetate and petroleum ether (b.p. 60°–80° C.), in the form of buff-coloured crystals.

REFERENCE EXAMPLE 1

The hereinafter indicated N-phenylpyrazole derivatives used as starting materials in the foregoing Examples were prepared as follows:

2,3,4-Trichlorophenylhydrazine (106 g) was added at laboratory temperature to a stirred solution of anhydrous sodium acetate (20.5 g) in glacial acetic acid (250 ml). Ethoxymethylenemalononitrile (61 g) was then added with stirring to the suspension thus obtained. Partial solution occurred within 5 minutes, after which a fine precipitate was formed. The mixture was stirred for one hour and then filtered. The solid obtained was washed successively with water, aqueous sodium bicarbonate solution and water and dried to give 2,3,4-trichlorophenylhydrazinomethylenemalononitrile (118 g), m.p. 149°–155° C., in the form of a yellow powder.

The 2,3,4-trichlorophenylhydrazinomethylenemalononitrile thus obtained was then heated at reflux for one hour in ethoxyethanol (300 ml). The hot solution was treated with decolourising charcoal, filtered and diluted with water (100 ml). The pale yellow crystals which formed were separated, dried and recrystallised from toluene (400 ml) to give 5-amino-4-cyano-1-(2,3,4-trichlorophenyl)pyrazole (100 g), m.p. 159°–160° C., in the form of colourless crystals.

By proceeding in a similar manner, but replacing the 2,3,4-trichlorophenylhydrazine by the hereafter identified appropriately substituted phenylhydrazine, there was prepared:

5-Amino-4-cyano-1-(2,3,5,6-tetrafluoro-4-trifluoromethylphenyl)pyrazole, m.p. 122°–122.5° C., in the form of off-white crystals, after crystallisation from toluene, from 2,3,5,6-tetrafluoro-4-trifluoromethylphenylhydrazine (prepared as described by Alsop et al, J. Chem. Soc, 1962, 1801), via 2,3,5,6-tetrafluoro-4-trifluoromethylphenylhydrazinomethylenemalononitrile (isolated as a pale yellow solid, m.p. 90°–93° C.);

5-Amino-4-cyano-1-(2,4,6-trichlorophenyl)pyrazole, m.p. 213°–214° C., after crystallisation from a mixture of acetone and toluene, in the form of cream coloured crystals, from 2,4,6-trichlorophenylhydrazine (described by Chatterway and Irving, J. Chem. Soc, 1931, 1740), via 2,4,6-trichlorophenylhydrazinomethylenemalononitrile (isolated as a light fawn-coloured powder, m.p. 168°–170° C.).

REFERENCE EXAMPLE 2

2,3,4-Trichlorophenylhydrazine, used as a starting material in Reference Example 1 was prepared as follows:

2,3,4-Trichloroaniline (100 g) was dissolved with stirring in glacial acetic acid (875 ml) at 55°–60° C. A solution of sodium nitrite (39.5 g) in concentrated sulphuric acid (300 ml) was then added over 15 minutes at 55°–60° C. to the solution thus obtained. The viscous mixture obtained was cooled to 5°–10° C. and a solution of stannous chloride dihydrate (437 g) in concentrated hydrochloric acid (375 ml) was added at 5°–10° C. over 20 minutes. A fine, off-white solid precipitated. To aid filtration, the mixture was warmed to 60° C., allowed to cool to laboratory temperature and then filtered. The precipitate was washed on the filter with saturated aqueous sodium chloride solution (100 ml). The damp powder thus obtained was added to a stirred mixture of aqueous ammonia (1.3 liters; S.G. 0.880) and ice. The fine slurry which formed was filtered and the precipitate obtained was dried at 80° C., and boiled twice with chloroform (2×1.5 liters). The chloroform extracts were combined and evaporated to dryness to give 2,3,4-trichlorophenylhydrazine (86 g), m.p. 142°–143° C., in the form of a colourless powder.

2,3,4-Trichloroaniline is a known compound, which is readily available.

REFERENCE EXAMPLE 3

The hereinafter indicated N-phenylpyrazole derivatives used as starting materials in the foregoing Examples were prepared as follows:

2,3,6-Trichloro-4-trifluoromethylphenylhydrazine (10.1 g) was added in one portion to a solution of ethoxymethylenemalononitrile [4.40 g; described by Huber, J. Amer. Chem. Soc., 65, 2224 (1943)] and anhydrous sodium acetate (1.47 g) in glacial acetic acid (34 ml) stirred at laboratory temperature. After stirring at laboratory temperature for 5 minutes, a fine precipitate formed and stirring at laboratory temperature was continued for 2 hours. The reaction mixture was then allowed to stand overnight at laboratory temperature and filtered. The solid precipitate was washed successively with a small quantity of glacial acetic acid, saturated aqueous sodium bicarbonate solution and water, to give 2,3,6-trichloro-4-trifluoromethylphenylhydrazinomethylenemalononitrile (9.6 g), m.p. 169°–170° C. in the form of a fawn-coloured powder.

The 2,3,6-trichloro-4-trifluoromethylphenylhydrazinomethylenemalononitrile thus obtained was heated at reflux for 1 hour in ethoxyethanol (50 ml). The hot solution was filtered and the filtrate was cooled, diluted with water (70 ml) and the solid precipitate was filtered off to give 5-amino-4-cyano-1-(2,3,6-trichloro-4-trifluoromethylphenyl)pyrazole (6.36 g), m.p. 186°–187° C., after crystallisation from toluene (25 ml), in the form of a buff-coloured crystalline solid. By proceeding in a similar manner, but replacing the 2,3,6-trichloro-4-trifluoromethylphenylhydrazine by the hereinafter identified appropriately substituted phenyl hydrazine, there was prepared:

5-Amino-1-(2-chloro-4-ethylphenyl)-4-cyanopyrazole, m.p. 174°–175° C., after crystallisation from toluene, in the form of light orange crystals, from 2-chloro-4-ethylphenylhydrazine, via 2-chloro-4-ethylphenylhydrazinomethylenemalononitrile.

REFERENCE EXAMPLE 4

The hereinafter indicated N-phenylpyrazole derivatives used as starting materials in the foregoing Examples were prepared as follows:

4-Methyl-2,3,5,6-tetrafluorophenylhydrazine [29.8 g; described by Burdon et al, J. Chem. Soc., 5152 (1965)] was added in one portion to a solution of ethoxymethylenemalononitrile (19 g) and anhydrous sodium acetate (5.3 g) in glacial acetic acid (65 ml) stirred at laboratory temperature. After stirring at laboratory temperature for 1 minute, a fine precipitate formed and stirring at laboratory temperature was continued for 4 hours. The reaction mixture was then allowed to stand overnight at laboratory temperature, diluted with water (50 ml) and filtered. The solid precipitate was washed successively with glacial acetic acid, water, saturated aqueous sodium bicarbonate solution and water, to give 4-methyl-2,3,5,6-tetrafluorophenylhydrazinomethylenemalononitrile (37 g), m.p. 140°–143° C., in the form of a yellow solid. The 4-methyl-2,3,5,6-tetrafluorophenylhydrazinomethylenemalononitrile thus obtained was heated at reflux for 45 minutes in ethoxyethanol (50 ml). The hot solution was treated with charcoal and filtered. The filtrate was cooled, diluted with water (20 ml) and the solid precipitate was filtered off and washed with water to give 5-amino-4-cyano-1-(4-methyl-2,3,5,6-tetrafluorophenyl)-pyrazole (26 g) m.p. 169°–170° C., in the form of a yellow solid. By proceeding in a similar manner, but replacing the 4-methyl-2,3,5,6-tetrafluorophenylhydrazine by the hereinafter identified appropriately substituted phenylhydrazine, there were prepared:

1-(4-Allyl-2,3,5,6-tetrafluorophenyl)-5-amino-4-cyanopyrazole, m.p. 124°–125° C., after crystallisation from toluene, in the form of colourless crystals, from 4-allyl-2,3,5,6-tetrafluorophenylhydrazine, via 4-allyl-2,3,5,6-tetrafluorophenylhydrazinomethylenemalononitrile (isolated in the form of a brown solid, m.p. 121°–123° C.);

5-Amino-1-(2-chloro-4-methylphenyl)-4-cyanopyrazole, m.p. 143°–144° C., in the form of fawn-coloured crystals, from 2-chloro-4-methylphenylhydrazine, m.p. 70°–72° C. [described by Bulow and Engler, Ber. 52, 639 (1919)], via 2-chloro-4-methylphenylhydrazinomethylenemalononitrile (isolated in the form of a fawn-coloured solid, m.p. 133°–134° C.);

5-Amino-4-cyano-1-(2,3-dichlorophenyl)pyrazole, m.p. 148°–150° C., in the form of colourless crystals, after crystallisation from toluene, from 2,3-dichlorophenylhydrazine [described in U.S. Pat. No. 2,863,864 (1958)] via 2,3-dichlorophenylhydrazinomethylenemalononitrile (isolated in the form of a sandy-coloured solid, m.p. 145°–146° C.).

REFERENCE EXAMPLE 5

Phenylhydrazines used as starting materials in Reference Example 3 were prepared as follows:

2-Chloro-4-ethylaniline [14.5 g.; described by K. Altau, J. Chem. Eng. Data, 8, 122 (1963)] was dissolved, with stirring, in glacial acetic acid (113 ml). A solution of sodium nitrite (7.0 g) in concentrated sulphuric acid (55 ml) was then added at 55°–60° C. The solution thus obtained was cooled to 0°–5° C. and a solution of stannous chloride (70 g) in concentrated hydrochloric acid (80 ml) was added with vigorous stirring. A cream-coloured solid precipitated. The mixture was filtered and the solid obtained was added to a mixture of aqueous ammonia and ice. The mixture thus obtained was extracted with diethyl ether (4×300 ml) and the combined ethereal extracts were dried over sodium sulphate, filtered and evaporated to dryness, to give 2-chloro-4-ethylphenylhydrazine (9.6 g), m.p. 55°–57° C., in the form of a cream-coloured solid. By proceeding in a similar manner, but replacing the 2-chloro-4-ethylaniline by the hereinafter indicated appropriately substituted aniline, there was prepared:

2,3,6-Trichloro-4-trifluoromethylphenylhydrazine, m.p. 72°–74° C., in the form of a white solid, from 2,3,6-trichloro-4-trifluoromethylaniline.

REFERENCE EXAMPLE 6

4-Allyl-2,3,5,6-tetrafluorophenylhydrazine, used as a starting material in Reference Example 4, was prepared as follows:

Allylpentafluorobenzene [41.6 g; described by Harper et al, J. Org. Chem., 29, 2385 (1964)] was added to a solution of hydrazine hydrate (100 ml) in ethanol (150 ml) and the mixture was heated at reflux for 24 hours. The solid precipitate which formed was collected by filtration and washed with ethanol and hexane to give 4-allyl-2,3,5,6-tetrafluorophenylhydrazine (18.8 g), m.p. 82°–84° C., in the form of colourless crystals. The filtrate was evaporated to dryness and the yellow solid thus obtained was washed with ethanol and hexane to give a further quantity (22.0 g) of 4-allyl-2,3,5,6-tetrafluorophenylhydrazine, m.p. 79°–81° C., in the form of a cream-coloured solid.

REFERENCE EXAMPLE 7

2,3,6-Trichloro-4-trifluoromethylaniline, used as a starting material in Reference Example 5, was prepared as follows:

A mixture of 3-chloro-4-trifluoromethylaniline [20 g; described in British Patent Specification No. 459,890] and hydrochloric acid (d:1.18; 12 ml) was suspended in water (600 ml). Chlorine gas (from 13 ml of liquid chlorine) was then passed into the stirred suspension with heating at reflux. On completion of the addition of chlorine gas, stirring was continued for a further 15 minutes. After cooling, the solution thus obtained was extracted with dichloromethane (3×250 ml). The combined organic extracts were washed with water, saturated aqueous sodium bicarbonate solution and water, dried over anhydrous sodium sulphate and evaporated. The red oil thus obtained was distilled (bp 143°–147° C./20 mmHg) to give an orange oil which crystallized on standing to give 2,3,6-trichloro-4-trifluoromethylaniline (12.26 g), m.p. 37°–39° C., in the form of an orange solid.

REFERENCE EXAMPLE 8

Ethoxymethylenemalononitrile [1.84 g; described by Huber, J. Amer. Chem. Soc., 65, 2224 (1943)] and 2,6-dichloro-4-trifluoromethylphenylhydrazine (3.7 g) were added to a magnetically-stirred solution of sodium acetate (0.6 g) in glacial acetic acid (15 ml) at laboratory temperature. After stirring for 15 minutes, a colourless solid precipitated from the clear brown solution obtained and stirring was continued for a further 15 minutes. The mixture was then filtered. The solid obtained was washed successively with acetic acid, water, aqueous sodium bicarbonate solution and water, to give 2,6-dichloro-4-trifluoromethylphenylhydrazinomethylenemalononitrile (3.4 g), m.p. 153°–154° C., in the form of colourless crystals.

The 2,6-dichloro-4-trifluoromethylphenylhydrazinomethylenemalononitrile thus obtained was then heated at reflux for 45 minutes in ethoxyethanol (15 ml). The hot solution was filtered and the filtrate was cooled, diluted with water (5 ml), and filtered, to give 5-amino-4-cyano-1-(2,6-dichloro-4-trifluoromethylphenyl)pyrazole (2.5 g), m.p. 165°–167° C., in the form of off-white crystals.

By proceeding in a similar manner, but replacing the 2,6-dichloro-4-trifluoromethylphenylhydrazine by the hereinafter indicated appropriately substituted phenylhydrazine, there were prepared:

5-Amino-1-(2-chloro-4-trifluoromethylphenyl)-4-cyanopyrazole, m.p. 185°–187° C., after crystallisation from toluene, in the form of fawn-coloured crystals, from 2-chloro-4-trifluoromethylphenylhydrazine, via 2-chloro-4-trifluoromethylphenylhydrazinomethylenemalononitrile, in the form of a brown powder, m.p. 138°–143° C.

REFERENCE EXAMPLE 9

Phenylhydrazines used as starting materials in Reference Example 8 were prepared as follows:

2,6-Dichloro-4-trifluoromethylphenylaniline (4.3 g) (described in U.S. Pat. No. 3,850,955) was dissolved, with stirring, in glacial acetic acid (23 ml). A solution of sodium nitrite (1.5 g) in concentrated sulphuric acid (11 ml) was then added at 55°–60° C. The solution thus obtained was cooled to 0°–5° C. and a solution of stannous chloride (16.4 g) in concentrated hydrochloric acid (14 ml) was added with vigorous stirring. A cream-coloured solid precipitated. The mixture was filtered and the solid obtained was added to a mixture of aqueous ammonium hydroxide solution and ice. The mixture thus obtained was extracted with diethyl ether (6×500 ml) and the combined ethereal extracts were dried over sodium sulphate, filtered and evaporated to dryness to give 2,6-dichloro-4-trifluoromethylphenylhydrazine (3.7 g), m.p. 54°–56° C., in the form of a colourless crystalline solid. By proceeding in a similar manner, but replacing the 2,6-dichloro-4-trifluoromethylaniline by 2-chloro-4-trifluoromethylaniline (described in U.S. Pat. No. 3,850,955), there was prepared:

2-Chloro-4-trifluoromethylphenylhydrazine, m.p. 38°–39° C., in the form of a colourless solid.

REFERENCE EXAMPLE 10

2,6-Dichloro-4-ethylphenylhydrazine (2.54 g) was added in one portion to a stirred solution of ethoxymethylenemalononitrile [1.55 g; described by Huber. J. Amer. Chem. Soc., 65, 2224 (1943)] and anhydrous sodium acetate (0.5 g) in glacial acetic acid (12 ml) at laboratory temperature. A fine precipitate formed after 5 minutes and stirring was continued for 2 hours. The reaction mixture was allowed to stand at laboratory temperature overnight then filtered. The solid product was washed successively with a small quantity of glacial acetic acid, saturated aqueous sodium bicarbonate solution and water, to give 2,6-dichloro-4-ethylphenylhydrazinomethylenemalononitrile (1.41 g), m.p. 137°–138° C., in the form of a fawn coloured solid.

The 2,6-dichloro-4-ethylphenylhydrazinomethylenemalononitrile thus obtained was heated at reflux for 1 hour in ethoxyethanol (15 ml). The hot solution was filtered and the filtrate diluted with water (15 ml) and the solid precipitate filtered off to give 5-amino-4- cyano-1-(2,6-dichloro-4-ethylphenyl)pyrazole (1.15 g), m.p. 189°–190° C., in the form of fawn-coloured crystals.

REFERENCE EXAMPLE 11

The phenylhydrazine used as starting material in Reference Example 10 was prepared by proceeding in a similar manner to that hereinbefore described in Reference Example 5 but replacing the 2-chloro-4-ethylaniline by 2,6-dichloro-4-ethylaniline. 2,6-Dichloro-4-ethylphenylhydrazine, m.p. 48°–50° C., was obtained in the form of a cream-coloured solid.

REFERENCE EXAMPLE 12

4-n-Butyl 2,3,5,6-tetrafluorophenylhydrazine, used as starting material in Reference Example 14 was prepared as follows:

n-Butylpentafluorobenzene [19.0 g; described by J. M. Birchall and R. N. Haszeldine J. Chem. Soc p 3719 (1961)] was added to a solution of hydrazine hydrate (50 ml; 99–100% w/w) in ethanol (100 ml) and the mixture heated at reflux for 72 hours. The reaction mixture was cooled, evaporated to dryness to give a solid which was filtered off and washed with ethanol and hexane to give 4-n-butyl-2,3,5,6-tetrafluorophenylhydrazine (20.5 g), m.p. 80°–81° C., in the form of colourless crystals.

REFERENCE EXAMPLE 13

2,6-Dichloro-4-ethylaniline used as a starting material in Reference Example 11 was prepared as follows:

A solution of 4-amino-3,5-dichloroacetophenone [15.8 g; described by Lutz et al, J. Org. Chem., 12, 617 (1947)] in glacial acetic acid (100 ml) and sulphuric acid (d:1.84; 8.2 g) was treated at 22°–27° C. for 22.5 hours with hydrogen in the presence of charcoal containing 5% palladium and filtered. The filtrate was evaporated to dryness and the yellow solid thus obtained was suspended in ice-water (150 ml). Aqueous sodium hydroxide solution (20% w/v) was added to pH10 and the mixture was then extracted with diethyl ether (3×150 ml). The ethereal extracts were combined, washed with water, dried over anhydrous sodium sulphate and evaporated to dryness. The yellow solid (11.75 g) thus obtained was chromatographed on a silica column (Merck, 250–400 mesh; pressure 25 lb in$^{-2}$) eluated with hexane-toluene (5:1). Evaporation of the eluate containing the faster-moving component gave 2,6-dichloro-4-ethylaniline (4.59 g), m.p. 47°–48° C., in the form of colourless crystals.

REFERENCE EXAMPLE 14

By proceeding in a similar manner to that hereinbefore described in Reference Example 10 but replacing the 2,6-dichloro-4-ethyl-phenylhydrazine by the hereinafter identified appropriately substituted phenyl-hydrazine, there were prepared:

5-Amino-4-cyano-1-(4-methyl-2,3,6-trichlorophenyl)pyrazole, m.p. 187.5°–189.5° C., in the form of off-white crystals, from 4-methyl-2,3,6-trichlorophenylhydrazine, via 4-methyl-2,3,6-trichlorophenylhydrazinomethylenemalononitrile (isolated in the form of a cream-coloured solid, m.p. 145°–147° C.).

5-Amino-4-cyano-1-(2,3-dichloro-4-ethylphenyl)-pyrazole, m.p. 152°–154° C., in the form of a colourless solid, from 2,3-dichloro-4-ethylphenylhydrazine, via 2,3-dichloro-4-ethylphenylhydrazinomethylenemalononitrile (isolated in the form of a cream-coloured solid, m.p. 138°–140° C.).

5-Amino-1-(2-chloro-4-n-propylphenyl)-4-cyanopyrazole, m.p. 117°–118° C., in the form of a fawn-coloured solid, from 2-chloro-4-n-propylphenylhydrazine via 2-chloro-4-n-propylphenylhydrazinomethylenemalononitrile (isolated in the form of a colourless solid, m.p. 136°–137° C.).

5-Amino-4-cyano-1-(2,6-dibromo-4-trifluoromethylphenyl)pyrazole, m.p. 187°–188° C., in the form of a colourless solid, from 2,6-dibromo-4-trifluoromethylphenylhydrazine, via 2,6-dibromo-4-trifluoromethylphenylhydrazinomethylenemalononitrile (isolated in the form of a cream-coloured solid, m.p. 174°–175° C.).

5-Amino-1-(2-chloro-4-isopropylphenyl)-4-cyanopyrazole, m.p. 180.5°–182° C., after crystallization from toluene, in the form of fawn-coloured crystals, from 2-chloro-4-isopropylphenylhydrazine, via 2-chloro-4-isopropylphenylhydrazinomethylenemalononitrile.

5-Amino-1-(4-n-butyl-2,3,5,6-tetrafluorophenyl)-4-cyanopyrazole, m.p. 123°–124° C., after crystallization from toluene, in the form of colourless crystals, from 4-n-butyl-2,3,5,6-tetrafluorophenylhydrazine, via 4-n-butyl-2,3,5,6-tetrafluorophenylhydrazinomethylenemalononitrile. 5-Amino-4-cyano-1-(4-ethyl-2,3,5,6-tetrafluorophenyl)pyrazole, m.p. 145.5°–146.5° C., after crystallization from toluene, in the form of colourless crystals, from 4-ethyl-2,3,5,6-tetrafluorophenylhydrazine, via 4-ethyl-2,3,5,6-tetrafluorophenylhydrazinomethylenemalononitrile.

5-Amino-4-cyano-1-(2,3,5,6-tetrafluoro-4-vinylphenyl)pyrazole, m.p. 157°–159° C., after crystallization from toluene, in the form of off-white crystals, from 2,3,5,6-tetrafluoro-4-vinylphenylhydrazine, via 2,3,5,6-tetrafluoro-4-vinylphenylhydrazinomethylenemalononitrile.

REFERENCE EXAMPLE 15

Phenylhydrazines used as starting materials in Reference Example 14 were prepared as follows:

By proceeding in a similar manner to that hereinbefore described in Reference Example 1 but replacing the 2-chloro-4-ethylaniline by the hereinafter indicated appropriately substituted aniline, there were prepared:

4-Methyl-2,3,6-trichlorophenylhydrazine, m.p. 131°–133° C., in the form of a white solid, from 4-methyl-2,3,6-trichloroaniline [described by F. Bell, J. Chem. Soc. p 2376, (1955)].

2,6-Dibromo-4-trifluoromethylphenylhydrazine, m.p. 65°–67° C., in the form of a fawn-coloured solid, from 2,6-dibromo-4-trifluoromethylaniline (prepared as described in Reference Example 20).

REFERENCE EXAMPLE 16

Phenylhydrazines used as starting materials in Reference Example 14, were prepared as follows:

By proceeding in a similar manner to that hereinbefore described in Reference Example 12 but replacing the n-butylpentafluorobenzene by the hereinafter indicated appropriately substituted benzene, there were prepared:

4-Ethyl-2,3,5,6-tetrafluorophenylhydrazine, m.p. 82°–83° C., in the form of colourless crystals, from ethylpentafluorobenzene [described by R. J. Harper et al. J. Org. Chem. 29, 2385 (1964)].

2,3,5,6-Tetrafluoro-4-vinylphenylhydrazine, m.p. 88.5°–89.5° C., after crystallization from aqueous ethanol, in the form of colourless crystals, from vinylpentafluorobenzene [described by J. C. Tatlow et al. J. Chem. Soc. pp 166–171 (1959)].

REFERENCE EXAMPLE 17

Phenylhydrazines used as starting materials in Reference Example 14 were prepared as follows:

A solution of 2-chloro-4-isopropylacetanilide (9.3 g) in a mixture of glacial acetic acid (66 ml) and hydrochloric acid (44 ml; density 1.19) was heated at reflux for 4 hours. After cooling, the reaction mixture was stirred and a solution of sodium nitrite (3.72 g) in concentrated sulphuric acid (27 ml) added at 15°–20° C. The solution thus obtained was cooled to 0°–5° C. and a solution of stannous chloride (40 g) in concentrated hydrochloric acid (35 ml) was added with vigorous stirring. A cream coloured precipitate formed. The mixture was filtered and the solid obtained basified with aqueous sodium hydroxide (2N, 350 ml). This was extracted with dichloromethane (3×200 ml) and the combined extracts washed with water (2×500 ml), dried over anhydrous magnesium sulphate and evaporated to dryness to give 2-chloro-4-isopropylphenylhydrazine (4.5 g), m.p. 64°–66° C., in the form of a colourless solid. The filtrate from the stannous-complex filtration was reduced under diminished pressure and the residue basified with aqueous sodium hydroxide (50% w/v), ice being added to maintain the temperature at 20°–25° C. The mixture was similarly extracted with dichloromethane to furnish a further quantity of 2-chloro-4-isopropylphenylhydrazine (3.03 g), m.p. 65°–67° C., in the form of a yellow solid.

By proceeding in a similar manner but replacing 2-chloro-4-isopropylacetanilide by the hereinafter appropriately substituted acetanilide, there was prepared:

2,3-Dichloro-4-ethylphenylhydrazine, m.p. 80°–82° C., in the form of a yellow solid, from 2,3-dichloro-4-ethylacetanilide.

2-Chloro-4-n-propylphenylhydrazine, in the form of an brown oil, from 2-chloro-4-n-propylacetanilide.

REFERENCE EXAMPLE 18

Sodium hypochlorite (60 ml; bleach grade 14–15% w/v available chlorine) was added to a solution of 3-chloro-4-ethylacetanilide [5 g; described by J. P. Hambooy J. Med. Chem. 16 765 (1973)] in a mixture of glacial acetic acid (10 ml), ethanol (10 ml) and water (10 ml). An exothermic reaction occurred resulting in the precipitation of an orange oil. The aqueous layer was decanted and the oil dissolved in diethyl ether and the ether was washed with water, aqueous sodium bicarbonate (sat.), water and then dried over anhydrous magnesium sulphate and was evaporated to dryness to give an oil which partially crystallized on standing. The orange semi-solid (4.27 g) thus obtained was chromatographed on a silica column (Merck, 250–400 mesh, pressure 25 lb in$^{-2}$) eluted with dichloromethaneethyl acetate (19:1), fractions being taken every 25 ml. Evaporation of the eluate (fractions 12+13) containing the faster moving component gave 2,5-dichloro-4-ethylacetanilide (0.8 g), m.p. 113°–114° C., in the form of a colourless solid. Evaporation of the eluate (fractions 16–20) containing the slower moving component gave 2,3-dichloro-4-ethylacetanilide (1.39 g), m.p. 94°–96° C., in the form of a colourless solid. Evaporation of the remaining eluate (fractions 24–37) gave recovered 3-chloro-4-ethylacetanilide (1.0 g), m.p. 100°–101° C., in the form of a colourless solid.

By proceeding in a similar manner, but replacing the 3-chloro-4-ethylacetanilide by the hereinafter appropriately substituted acetanilide and chromatographing the crude product using the eluent hereinafter specified there was prepared:

2-Chloro-4-n-propylacetanilide, m.p. 78°–79° C., after crystallization from ethanol-water, in the form of colourless crystals, after chromatography of the crude product using dichloromethane as eluent, from p-n-propylacetanilide [described by Willgeralt Ann, 327, 307 (1903)].

REFERENCE EXAMPLE 19

Acetic anhydride (21 ml) was added to a solution of 4-isopropylaniline (27 g) in glacial acetic acid (62 ml) and the reaction mixture heated at reflux for 1.5 hours. The solution was then stirred and cooled to 10° C. and concentrated hydrochloric acid (67 ml) added. The reaction mixture was then stirred vigorously while a solution of sodium chlorate (6.7 g) in water (18 ml) was added dropwise at 15°–20° C. and the stirring continued at laboratory temperature for 6 hours. After standing at room temperature overnight, the reaction mixture was poured onto ice-water (1.5l) to precipitate a brown solid which was filtered off and washed with water. The solid was chromatographed on a silica column (Merck, 250–400 mesh; pressure 25 lb in$^{-2}$) using dichloromethane-ethyl acetate (15:1) as eluent. Evaporation of the eluate containing the faster moving component gave 2-chloro-4-isopropylacetanilide (9.76 g), m.p. 115°–116° C., in the form of a fawn coloured solid.

REFERENCE EXAMPLE 20

Bromine (96 g) was added dropwise to a stirred mixture of 4-aminobenzotrifluoride (48.3 g) and reduced iron (3 g) in ethyl acetate (300 ml) at a temperature of 30°–50° C. The solution was then heated at reflux for 1 hour, after which evolution of hydrogen bromide ceased. The reaction mixture was evaporated to dryness and the residue dissolved in diethyl ether (1.5l) and basified with aqueous sodium hydroxide (2N) to pH 14. The organic layer was removed and the aqueous layer extracted with diethyl ether (500 ml). The ether extracts were combined, washed with water (2×500 ml) and dried over anhydrous sodium sulphate, then evaporated to give a brown semi-solid (90.0 g). The semi-solid was treated with hexane (50 ml) and filtered, the filtrate was cooled to −30° C. to precipitate a solid which was removed by filtration to give 2,6-dibromo-4-trifluoromethylaniline (65.4 g), m.p. 37°–39° C., in the form of fawn-coloured crystals.

REFERENCE EXAMPLE 21

By proceeding in a similar manner to that hereinbefore described in Reference Example 4 but replacing the 4-methyl-2,3,5,6-tetrafluorophenylhydrazine by the hereinafter identified appropriately substituted phenylhydrazine, there were prepared:

5-Amino-4-cyano-1-(3,5-difluoro-2,4,6-trichlorophenyl)pyrazole, m.p. 210°–212° C., after crystallisation from toluene, in the form of a colourless solid, from 3,5-difluoro-2,4,6-trichlorophenylhydrazine [described by N. Ishikawa, Nippon Kagaku Zasshi 86, 1202 (1965)] via 3,5-difluoro-2,4,6-trichlorophenylhydrazinomethylenemalononitrile.

5-Amino-4-cyano-1-(2,4-dichloro-6-methylphenyl)-pyrazole, m.p. 199°–202° C., after crystallisation from toluene in the form of a colourless solid, from 2,4- dichloro-6-methylphenylhydrazine (described in British Pat. No. 904,852) via 2,4-dichloro-6-methylphenylhydrazinomethylenemalononitrile (isolated in the form of an off-white solid, m.p. 151°-153° C.).

5-Amino-1-(4-bromo-2,3,5,6-tetrafluorophenyl)-4-cyanopyrazole, m.p. 208°-210° C., after crystallisation from toluene, in the form of a colourless solid, from 4-bromo-2,3,5,6-tetrafluorophenylhydrazine [described by J. Burdon. Tet. Lett. 22, 1183 (1966)] via 4-bromo-2,3,5,6-tetrafluorophenylhydrazinomethylenemalononitrile.

5-Amino-1-(4-chloro-2,3,5,6-tetrafluorophenyl)-4-cyanopyrazole, m.p. 164°-166° C., after crystallisation from toluene, in the form of a colourless solid, from 4-chloro-2,3,5,6-tetrafluorophenylhydrazine [described by N. Ishikawa, Nippon Kagaku Zasshi 89, 321 (1968)] via 4-chloro-2,3,5,6-tetrafluorophenylhydrazinomethylenemalononitrile.

5-Amino-1-(2-bromo-4-trifluoromethylphenyl)-4-cyanopyrazole, m.p. 194°-196° C., after crystallisation from toluene in the form of colourless crystals, from 2-bromo-4-trifluoromethylphenylhydrazine, via 2-bromo-4-trifluoromethylphenylhydrazinomethylenemalononitrile. (±)-5-Amino-1-(4-sec-butyl-2,3,5,6-tetrafluorophenyl)-4-cyanopyrazole, m.p. 125.5°-127° C., after crystallisation from toluene, in the form of colourless crystals, from (±)-4-sec-butyl-2,3,5,6-tetrafluorophenylhydrazine via (±)-4-sec-butyl-2,3,5,6-tetrafluorophenylhydrazinomethylenemalononitrile.

5-Amino-4-cyano-1-(2,3,4,6-tetrachlorophenyl)-pyrazole, m.p. 193°-194° C., in the form of a colourless crystalline solid, from 2,3,4,6-tetrachlorophenylhydrazine [described by Chattaway J. Chem. Soc. p 1925 (1931)] via 2,3,4,6-tetrachlorophenylhydrazinomethylenemalononitrile (isolated in the form of a fawn coloured solid, m.p. 174°-176° C.).

REFERENCE EXAMPLE 22

2-Bromo-4-trifluoromethylphenylhydrazine, in the form of a red oil, used as a starting material in Reference Example 21, was prepared by proceeding in a similar manner to that hereinbefore described in Reference Example 5 but replacing the 2-chloro-4-ethylaniline by 2-bromo-4-trifluoromethylaniline (described in U.S. Pat. No. 3,995,042, Pharm Doc 94181X).

REFERENCE EXAMPLE 23

One of the phenylhydrazines used as a starting material in Reference Example 21 was prepared as follows:

By proceeding in a similar manner to that hereinbefore described in Reference Example 12 but replacing the n-butylpentafluorobenzene by the hereinafter appropriately substituted pentafluorobenzene, and adding sufficient dioxan to the reaction mixture to obtain a homogeneous solution, there was obtained:

4-sec-Butyl-2,3,5,6-tetrafluorophenylhydrazine, m.p. 23°-29° C., in the form of a yellow waxy solid, from sec-butylpentafluorobenzene.

REFERENCE EXAMPLE 24 sec-Butylpentafluorobenzene, used as a starting material in Reference Example 23, was prepared as follows:

A solution of sec-butyl lithium (350 ml; 12% in cyclohexane) was added over a period of 1 hour to a stirred mixture of hexafluorobenzene (80 g) in cyclohexane (750 ml) at a temperature of 0° C. On warming the reaction mixture above 0° C. a violently exothermic reaction took place which was brought under control by external cooling (Cardice-acetone). The reaction mixture was subsequently brought to room temperature (no further reaction occurred) and was quenched with water (600 ml). The organic layer was separated, washed with dilute hydrochloric acid (2N; 2×200 ml) and water (2×200 ml) and dried over anhydrous magnesium sulphate, and afterwards distilled through a 15 cm vigreux column. The fraction distilling at 160°-170° C. was collected to give sec-butylpentafluorobenzene (50.3 g), b.p. 162°-164° C. (760 mm), in the form of a colourless liquid.

Hexafluorobenzene is a known compound and is readily available.

We claim:

1. An acylamino-N-phenylpyrazole derivative of the formula:

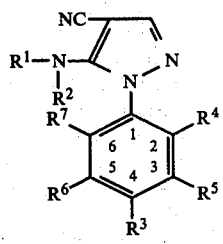

wherein $R^1$ represents an $R^8C(=O)-$ group (wherein $R^8$ represents a hydrogen atom, a straight- or branched-chain alkyl group containing from 1 to 7 carbon atoms, unsubstituted or substituted by a straight- or branched-chain alkoxy group containing from 1 to 4 carbon atoms by an alkoxycarbonyl group containing from 2 to 5 carbon atoms or by one or more halogen atoms, or $R^8$ represents a straight- or branched-chain alkoxy group containing from 1 to 4 carbon atoms, unsubstituted or substituted by a straight- or branched-chain alkoxy group containing from 1 to 4 carbon atoms, by an alkoxycarbonyl group containing from 2 to 5 carbon atoms or by one or more halogen atoms, or $R^8$ represents a straight- or branched-chain alkenyloxy group containing 3 or 4 carbon atoms, or a cycloalkyl group containing from 3 to 6 carbon atoms unsubstituted or substituted by a methyl or ethyl group, or a phenoxy group), $R^2$ represents a hydrogen atom or an $R^8C(=O)-$ group, wherein $R^8$ is as hereinbefore defined, and $R^8C(=O)-$ groups represented by $R^1$ and $R^2$ may be the same or different, or $R^1$ and $R^2$ together represent $-CO-(CR^aR^b)_m-CO$, $R^3$ represents a fluorine, chlorine or bromine atom, a straight- or branched-chain alkyl group containing from 1 to 4 carbon atoms unsubstituted or substituted by one or more halogen atoms, or a straight- or branched-chain alkenyl group containing from 2 to 4 carbon atoms, $R^4$ represents a fluorine, chlorine or bromine atom or a nitro, methyl or ethyl group, and $R^5$, $R^6$ and $R^7$, which may be the same or different, each represent a hydrogen, fluorine, chlorine or bromine atom or a nitro, methyl or ethyl group, or $R^4$ and $R^5$ each represent a chlorine atom and $R^3$, $R^6$ and $R^7$ each represent a hydrogen atom, $R^a$ and $R^b$, which may be the same or different, each represent a hydrogen atom or a straight- or branched-chain alkyl group containing from 1 to 4 carbon atoms, and m represents 2 or 3.

2. An acylamino-N-phenylpyrazole derivative according to claim 1 wherein $R^8$ represents an alkyl or alkoxy group substituted by one or more chlorine atoms.

3. An acylamino-N-phenylpyrazole derivative according to claim 1 wherein $R^3$ represents an alkyl group substituted by one or more fluorine atoms.

4. An acylamino-N-phenylpyrazole derivative according to claim 3 wherein $R^3$ represents a trifluoromethyl group.

5. An acylamino-N-phenylpyrazole derivative according to claim 1 wherein $R^1$ represents an $R^8C(=O)$— group (wherein $R^8$ represents a hydrogen atom, a straight- or branched-chain alkyl group containing from 1 to 7 carbon atoms unsubstituted or substituted by one or more halogen atoms, a straight- or branched-chain alkoxy group containing from 1 to 4 carbon atoms unsubstituted or substituted by one or more halogen atoms, or a phenoxy group), $R^2$ represents a hydrogen atom or an $R^8C(=O)$— group (wherein $R^8$ represents a hydrogen atom, a straight- or branched-chain alkyl group containing from 1 to 7 carbon atoms unsubstituted or substituted by one or more halogen atoms, a straight- or branched-chain alkoxy group containing from 1 to 4 carbon atoms unsubstituted or substituted by one or more halogen atoms, or a phenoxy group), and $R^8C(=O)$— groups represented by $R^1$ and $R^2$ are identical, $R^3$ represents a fluorine, chlorine or bromine atom, a trifluoromethyl group or an unsubstituted straight- or branched-chain alkyl group containing from 1 to 4 carbon atoms, and $R^4$, $R^5$, $R^6$ and $R^7$ are as defined in claim 1.

6. An acylamino-N-phenylpyrazole derivative according to claim 1 wherein $R^1$ represents an $R^8C(=O)$— group, wherein $R^8$ represents a hydrogen atom, a straight- or branched-chain alkyl group containing from 1 to 7 carbon atoms unsubstituted or substituted by one or more halogen atoms, a straight- or branched-chain alkoxy group containing from 1 to 4 carbon atoms unsubstituted or substituted by one or more halogen atoms, or a phenoxy group, a straight- or branched-chain alkyl group containing from 1 to 7 carbon atoms substituted by a straight- or branched-chain alkoxy group containing from 1 to 4 carbon atoms or by an alkoxycarbonyl group containing from 2 to 5 carbon atoms, a straight- or branched-chain alkoxy group containing from 1 to 4 carbon atoms substituted by a straight- or branched-chain alkoxy group containing from 1 to 4 carbon atoms or by an alkoxycarbonyl group containing from 2 to 5 carbon atoms, or an unsubstituted or methyl-substituted cycloalkyl group containing from 3 to 6 carbon atoms, $R^2$ represents a hydrogen atom or an $R^8C(=O)$— group, wherein $R^8$ represents a hydrogen atom, a straight- or branched-chain alkyl group containing from 1 to 7 carbon atoms unsubstituted or substituted by one or more halogen atoms, a straight- or branched-chain alkoxy group containing from 1 to 4 carbon atoms unsubstituted or substituted by one or more halogen atoms, or a phenoxy group, or represents a straight- or branched-chain alkyl group containing from 1 to 7 carbon atoms substituted by a straight- or branched-chain alkoxy group containing from 1 to 4 carbon atoms or by an alkoxycarbonyl group containing from 2 to 5 carbon atoms, a straight- or branched-chain alkoxy group containing from 1 to 4 carbon atoms substituted by a straight- or branched-chain alkoxy group containing from 1 to 4 carbon atoms or by an alkoxycarbonyl group containing from 2 to 5 carbon atoms, or an unsubstituted or methyl-substituted cycloalkyl group containing from 3 to 6 carbon atoms, and $R^8C(=O)$— groups represented by $R^1$ and $R^2$ are identical, $R^3$ represents a fluorine, chlorine or bromine atom, a trifluoromethyl group or an unsubstituted straight- or branched-chain alkyl group containing from 1 to 4 carbon atoms, and $R^4$, $R^5$, $R^6$ and $R^7$ are as defined in claim 1.

7. An acylamino-N-phenylpyrazole derivative according to claim 1 wherein $R^1$ represents an $R^{8'}C(=O)$— group, wherein $R^{8'}$ represents an unsubstituted straight- or branched-chain alkyl group containing from 1 to 5 carbon atoms, an unsubstituted methoxy group or an unsubstituted or methyl-substituted cyclopropyl group.

8. An acylamino-N-phenylpyrazole derivative according to claim 1 wherein $R^2$ represents a hydrogen atom or an $R^{8''}C(=O)$— group, wherein $R^{8''}$ represents an unsubstituted straight- or branched-chain alkyl group containing from 1 to 5 carbon atoms, an unsubstituted methoxy group or an unsubstituted or methyl-substituted cyclopropyl group.

9. An acylamino-N-phenylpyrazole derivative according to claim 1 wherein $R^3$ represents a chlorine atom or a trifluoromethyl or unsubstituted ethyl group.

10. An acylamino-N-phenylpyrazole derivative according to claim 1 wherein $R^4$ represents a fluorine or chlorine atom.

11. An acylamino-N-phenylpyrazole derivative according to claim 1 wherein $R^5$ represents a hydrogen, fluorine or chlorine atom.

12. An acylamino-N-phenylpyrazole derivative according to claim 1 wherein $R^6$ represents a hydrogen or fluorine atom.

13. An acylamino-N-phenylpyrazole derivative according to claim 1 wherein $R^7$ represents a hydrogen, fluorine or chlorine atom.

14. An acylamino-N-phenylpyrazole derivative according to claim 1 wherein $R^3$ represents an unsubstituted methyl group, and $R^4$, $R^5$, $R^6$, and $R^7$ each represent a fluorine atom.

15. An acylamino-N-phenylpyrazole derivative according to claim 1, wherein $R^1$ represents an $R^{8'}C(=O)$— group wherein $R^{8'}$ represents an unsubstituted straight- or branched-chain alkyl group containing from 1 to 5 carbon atoms, an unsubstituted methoxy group or an unsubstituted or methyl-substituted cyclopropyl group, $R^2$ represents a hydrogen atom or an $R^{8''}C(=O)$— group wherein $R^{8''}$ represents an unsubstituted straight- or branched-chain alkyl group containing from 1 to 5 carbon atoms, an unsubstituted methoxy group or an unsubstituted or methyl-substituted cyclopropyl group, $R^3$ represents a chlorine atom or a trifluoromethyl or unsubstituted ethyl group, $R^4$ represents a fluorine or chlorine atom, $R^5$ represents a hydrogen, fluorine or chlorine atom, $R^6$ represents a hydrogen or fluorine atom, and $R^7$ represents a hydrogen, fluorine or chlorine atom, or $R^1$ represents an $R^{8'}C(=O)$— group, $R^2$ represents a hydrogen atom or an $R^{8''}C(=O)$— group, $R^3$ represents an unsubstituted methyl group, and $R^4$, $R^5$, $R^6$ and $R^7$ each represents a fluorine atom.

16. An acylamino-N-phenylpyrazole derivative according to claim 1 which is 5-acetamido-4-cyano-1-(2,3,4-trichlorophenyl)pyrazole, 4-cyano-5-diacetylamino-1-(2,3,4-trichlorophenyl)pyrazole, 5-acetamido-4-cyano-1-(2,3,5,6-tetrafluoro-4-trifluoromethylphenyl)pyrazole, 4-cyano-5-propionamido-1-(2,3,4-trichlorophenyl)pyrazole, or 5-acetamido-4-cyano-1-(2,4,6-trichlorophenyl)pyrazole.

17. An acylamino-N-phenylpyrazole derivative according to claim 1 which is 4-cyano-5-di(phenoxycarbonyl)amino-1-(2,3,4,-trichloro-phenyl)pyrazole.

18. An acylamino-N-phenylpyrazole derivative according to claim 1 which is 4-cyano-5-diacetylamino-1-(4-methyl-2,3,5,6-tetrafluorophenyl)pyrazole, 5-acetamido-4-cyano-1-(4-methyl-2,3,5,6-tetrafluorophenyl)pyrazole, 5-acetamido-4-cyano-1-(2,3,6-trichloro-4-trifluoromethylphenyl)pyrazole, 5-acetamido-4-cyano-1-(2,3,4,6-tetrachlorophenyl)pyrazole, 5-acetamido-1-(2-chloro-4-ethylphenyl)-4-cyanopyrazole, 4-cyano-5-dipropionylamino-1-(2,3,4-trichlorophenyl)pyrazole, 5-n-butyramido-4-cyano-1-(2,3,4-trichlorophenyl)pyrazole, 4-cyano-5-isobutyramido-1-(2,3,4-trichlorophenyl)pyrazole, 4-cyano-5-n-pentanamido-1-(2,3,4-trichlorophenyl)pyrazole, 4-cyano-5-(3-methylbutyramido)-1-(2,3,4-trichlorophenyl)pyrazole, 4-cyano-5-n-hexanamido-1-(2,3,4-trichlorophenyl)pyrazole, 5-acetamido-4-cyano-1-(2,3-dichlorophenyl)pyrazole, 5-acetamido-4-cyano-1-(2,4-dichlorophenyl)pyrazole, 4-cyano-5-(2-methylbutyramido)-1-(2,3,4-trichlorophenyl)pyrazole, 4-cyano-5-(2-ethylbutyramido)-1-(2,3,4-trichlorophenyl)pyrazole, 4-cyano-5-cyclopropylcarbonamido-1-(2,3,4-trichlorophenyl)pyrazole, 4-cyano-5-(2,2-dimethylpropionamido)-1-(2,3,4-trichlorophenyl)pyrazole, 4-cyano-5-propionamido-1-(2,3,5,6-tetrafluoro-4-trifluoromethylphenyl)pyrazole, 1-(2-chloro-4-ethylphenyl)-4-cyano-5-propionamidopyrazole, or 4-cyano-5-propionamido-1-(2,3,4,6-tetrachlorophenyl)pyrazole.

19. An acylamino-N-phenylpyrazole derivative according to claim 1 which is 5-acetamido-1-(2-chloro-4-methylphenyl)-4-cyanopyrazole, 5-acetamido-1-(4-allyl-2,3,5,6-tetrafluorophenyl)-4-cyanopyrazole, 4-cyano-5-n-heptanamido-1-(2,3,4-trichlorophenyl)pyrazole, 4-cyano-5-n-octanamido-1-(2,3,4-trichlorophenyl)pyrazole, 4-cyano-5-cyclopentylcarbonamido-1-(2,3,4-trichlorophenyl)pyrazole, 4-cyano-5-formamido-1-(2,3,4-trichlorophenyl)pyrazole, or 4-cyano-5-(2-ethylhexanamido)-1-(2,3,4-trichlorophenyl)pyrazole.

20. An acylamino-N-phenylpyrazole derivative according to claim 1 which is 5-acetamido-4-cyano-1-(2,3-dichloro-4-ethylphenyl)pyrazole, 4-cyano-5-propionamido-1-(2,3,6-trichloro-4-trifluoromethylphenyl)pyrazole, 5-n-butyramido-4-cyano-1-(2,3,5,6-tetrafluoro-4-trifluoromethylphenyl)pyrazole, 4-cyano-5-isobutyramido-1-(2,3,5,6-tetrafluoro-4-trifluoromethylphenyl)pyrazole, 4-cyano-5-cyclopropylcarbonamido-1-(2,3,5,6-tetrafluoro-4-trifluoromethylphenyl)pyrazole, 4-cyano-5-(2-ethylbutyramido)-1-(2,3,5,6-tetrafluoro-4-trifluoromethylphenyl)pyrazole, 4-cyano-5-methoxycarbonylamino-1-(2,3,4-trichlorophenyl)pyrazole, 1-(2-chloro-4-trifluoromethylphenyl)-4-cyano-5-methoxycarbonylaminopyrazole, 4-cyano-5-methoxycarbonylamino-1-(2,3,5,6-tetrafluoro-4-trifluoromethylphenyl)pyrazole, 4-cyano-5-diacetylamino-1-(2,3,5,6-tetrafluoro-4-trifluoromethylphenyl)pyrazole, 1-(2-chloro-4-trifluoromethylphenyl)4-cyano-5-diacetylaminopyrazole, 4-cyano-5-diacetylamino-1-(2,4,6-trichlorophenyl)pyrazole, 4-cyano-5-diacetylamino-1-(2,4-dichlorophenyl)pyrazole, 1-(2-chloro-4-trifluoromethylphenyl)-4-cyano-5-propionamidopyrazole, 5-n-butyramido-1-(2-chloro-4-trifluoromethylphenyl)-4-cyanopyrazole, 1-(2-chloro-4-trifluoromethylphenyl)-4-cyano-5-(3-methylbutyramido)pyrazole, 1-(2-chloro-4-trifluoromethylphenyl)-4-cyano-5-cyclopropylcarbonamidopyrazole, 5-acetamido-1-(2-chloro-4-trifluoromethylphenyl)-4-cyano pyrazole, 5-acetamido-4-cyano-1-(4-ethyl-2,3,5,6-tetrafluorophenyl)pyrazole, 4-cyano-1-(4-methyl-2,3,5,6-tetrafluorophenyl)-5-propionamidopyrazole, 4-cyano-5-diacetylamino-1-(4-ethyl-2,3,5,6-tetrafluorophenyl)pyrazole, 5-acetamido-4-cyano-1-(2,6-dichloro-4-trifluoromethylphenyl)pyrazole, 4-cyano-1-(2,6-dichloro-4-trifluoromethylphenyl)-5-propionamidopyrazole, 4-cyano-5-propionamido-1-(2,4,6-trichlorophenyl)pyrazole, 4-cyano-1-(2,4-dichlorophenyl)-5-propionamidopyrazole, 5-isobutyramido-1-(2-chloro-4-trifluoromethylphenyl)-4-cyanopyrazole, 1-(2-chloro-4-trifluoromethylphenyl)-4-cyano-5-pentanamidopyrazole, 4-cyano-5-(3-methylbutyramido)-1-(2,3,5,6-tetrafluoro-4-trifluoromethylphenyl)pyrazole, 1-(2-chloro-4-trifluoromethylphenyl)-4-cyano-5-(2-methylbutyramido)pyrazole, 1-(2-chloro-4-trifluoromethylphenyl)-4-cyano-5-(2,2-dimethylpropionamido)pyrazole, 4-cyano-1-(2,6-dichloro-4-trifluoromethylphenyl)-5-(3-methylbutyramido)pyrazole, 5-n-butyramido-4-cyano-1-(2,6-dichloro-4-trifluoromethylphenyl)pyrazole, 1-(2-chloro-4-trifluoromethylphenyl)-4-cyano-5-(2-ethylbutyramido)pyrazole, 4-cyano-1-(2,6-dichloro-4-trifluoromethylphenyl)-5-isobutyramidopyrazole, 4-cyano-5-cyclopropylcarbonamido-1-(2,6-dichloro-4-trifluoromethylphenyl)pyrazole, 4-cyano-1-(2,6-dichloro-4-trifluoromethylphenyl)-5-methoxycarbonylaminopyrazole, 4-cyano-1-(2,6-dichloro-4-trifluoromethylphenyl)-5-pentanamidopyrazole, 4-cyano-1-(2,6-dichloro-4-trifluoromethylphenyl)-5-(2-methylbutyramido)pyrazole, 4-cyano-5-(2-methylpentanamido)-1-(2,3,4-trichlorophenyl)pyrazole, 5-acetamido-1-(4-chloro-2,3,5,6-tetrafluorophenyl)-4-cyanopyrazole, 1-(4-chloro-2,3,5,6-tetrafluorophenyl)-4-cyano-5-propionamidopyrazole, 4-cyano-1-(2,6-dichloro-4-trifluoromethylphenyl)-5-(2,2-dimethylpropionamido)pyrazole, 4-cyano-1-(2,6-dichloro-4-trifluoromethylphenyl)-5-(2-ethylbutyramido)pyrazole, 1-(2-chloro-4-trifluoromethylphenyl)-4-cyano-5-(2-methylpentanamido)pyrazole, 5-acetamido-4-cyano-1-(2,6-dichloro-4-ethylphenyl)pyrazole, 4-cyano-5-diacetylamino-1-(2,6-dichloro-4-trifluoromethylphenyl)pyrazole, 4-cyano-5-dibutyrylamino-1-(2,3,4-trichlorophenyl)pyrazole, 4-cyano-5-dipentanoylamino-1-(2,3,4-trichlorophenyl)pyrazole, 4-cyano-5-di(3-methylbutyryl)amino-1-(2,3,4-trichlorophenyl)pyrazole, 5-(N-acetyl-N-propionyl)amino-4-cyano-1-(2,3,4-trichlorophenyl)pyrazole, 5-(N-acetyl-N-cyclopropylcarbonyl)amino-4-cyano-1-(2,3,4-trichlorophenyl)pyrazole, 5-(N-acetyl-N-2-ethylbutyryl)amino-4-cyano-1-(2,3,4-trichlorophenyl)pyrazole, 4-cyano-5-diisobutyrylamino-1-(2,3,4-trichlorophenyl)pyrazole, 5-(N-acetyl-N-isobutyryl)amino-1-(2,3,4-trichlorophenyl)-4-cyanopyrazole, 1-(2-chloro-4-trifluoromethylphenyl)-4-cyano-5-dipropionylaminopyrazole, 4-cyano-1-(2,6-dichloro-4-trifluoromethylphenyl)-5-dipropionylaminopyrazole, 4-cyano-5-(N-isobutyryl-N-propionyl)amino-1-(2,3,4-trichlorophenyl)pyrazole, 5-(N-acetyl-N-propionyl)amino-1-(2-chloro-4-trifluoromethylphenyl)-4-cyanopyrazole, 5-(N-acetyl-N-pentanoyl)amino-4-cyano-1-(2,3,4-trichlorophenyl)pyrazole, 5-(N-acetyl-N-methoxycarbonyl)amino-4-cyano-1-(2,3,4-trichlorophenyl)pyrazole, 4-cyano-1-(2,6-dichloro-4-trifluoromethylphenyl)-5-(2-methylpentanamido)pyrazole, 1-(2-chloro-4-trifluoromethylphenyl)-4-cyano-5-di(3-methylbutyryl)aminopyrazole, 1-(4-chloro-2,3,5,6-tetrafluorophenyl)-4-cyano-5- diacetylaminopyrazole, 4-cyano-5-(N-isobutyryl-N-methoxycarbonyl)amino-1-(2,3,4-trichlorophenyl)pyrazole, 5-acetamido-4-cyano-1-(3,5-difluoro-2,4,6-trichlorophenyl)pyrazole, 4-cyano-5-diacetylamino-1-(2,3,4,6-tetrachlorophenyl)pyrazole, 4-cyano-5-di(3-methylbutyryl)amino-1-(2,3,5,6-tetrafluoro-4-trifluoromethyl)pyrazole, 1-(2-chloro-4-trifluoromethylphenyl)-4-cyano-5-(2-methylcyclopropylcarbonamido)pyrazole, 4-cyano-5-cyclopropylcarbonamido-1-(2,3,4,6-tetrachlorophenyl)pyrazole, 4-cyano-5-(2-methylcyclopropylcarbonamido)-1-(2,3,5,6-tetrafluoro-4-trifluoromethylphenyl)pyrazole, 4-cyano-1-(2,6-dichloro-4-trifluoromethylphenyl)-5-(2-methylcyclopropylcarbonamido)pyrazole, or 4-cyano-1-(2,6-dichloro-4-trifluoromethylphenyl)-5-di-(3-methylbutyryl)aminopyrazole.

21. An acylamino-N-phenylpyrazole derivative according to claim 1 which is 4-cyano-5-(2-ethyl-3-methylbutyramido)-1-(2,3,4-trichlorophenyl)pyrazole, 5-acetamido-4-cyano-1-(4-methyl-2,3,6-trichlorophenyl)pyrazole, 5-acetamido-1-(2-chloro-4-isopropylphenyl)-4-cyanopyrazole, 1-(2-chloro-4-methylphenyl)-4-cyano-5-propionamidopyrazole, 1-(2-chloro-4-isopropylphenyl)-4-cyano-5-propionamidopyrazole, 4-cyano-5-cyclohexylcarbonamido-1-(2,3,4-trichlorophenyl)pyrazole, 4-cyano-5-[(2-ethoxy)ethoxycarbonylamino]-1-(2,3,4-trichlorophenyl)pyrazole, 4-cyano-5-isopropoxycarbonylamino-1-(2,3,4-trichlorophenyl)pyrazole, 5-n-butoxycarbonylamino-4-cyano-1-(2,3,4-trichlorophenyl)pyrazole, 4-cyano-5-n-propoxycarbonylamino-1-(2,3,4-trichlorophenyl)pyrazole, 4-cyano-5-ethoxycarbonylamino-1-(2,3,4-trichlorophenyl)pyrazole, 5-t-butoxycarbonylamino-4-cyano-1-(2,3,4-trichlorophenyl)pyrazole, 4-cyano-5-(2-propenyloxycarbonylamino)-1-(2,3,4-trichlorophenyl)pyrazole, 4-cyano-5-ethoxycarbonylamino-1-(2,3,5,6-tetrafluoro-4-trifluoromethylphenyl)pyrazole, 5-acetamido-1-(4-n-butyl-2,3,5,6-tetrafluorophenyl)-4-cyanopyrazole, 5-acetamido-1-(4-bromo-2,3-dichlorophenyl)-4-cyanopyrazole, 5-acetamido-4-cyano-1-(2-nitro-4-trifluoromethylphenyl)-pyrazole, 5-acetamido-4-cyano-1-(pentafluorophenyl)pyrazole, 4-cyano-5-dichloroacetamido-1-(2,3,4-trichlorophenyl)-pyrazole, 4-cyano-5-cyclobutylcarbonamido-1-(2,3,4-trichlorophenyl)pyrazole, 5-(4-chlorobutyramido)-4-cyano-1-(2,3,4-trichlorophenyl)pyrazole, 4-cyano-1-(2,3-dichlorophenyl)-5-propionamidopyrazole, 4-cyano-5-di(phenoxycarbonyl)amino-1-(2,3,5,6-tetrafluoro-4-trifluoromethylphenyl)pyrazole, 1-(2-chloro-4-trifluoromethylphenyl)-4-cyano-5-di(phenoxycarbonyl)aminopyrazole, 1-(2-chloro-4-n-propylphenyl)-4-cyano-5-diacetylaminopyrazole, 4-cyano-5-diacetylamino-1-(2,6-dibromo-4-trifluoromethylphenyl)pyrazole, 5-acetamido-4-cyano-1-(2,6-dibromo-4-trifluoromethylphenyl)pyrazole, 5-acetamido-4-cyano-1-(2,3,4,6-tetrafluorophenyl)pyrazole, 5-isobutoxycarbonylamino-4-cyano-1-(2,3,4-trichlorophenyl)pyrazole, 5-acetamido-1-(2-chloro-4-n-propylphenyl)-4-cyanopyrazole, 1-(2-chloro-4-trifluoromethylphenyl)-4-cyano-5-cyclohexylcarbonamidopyrazole, 5-(5-chloropentanamido)-4-cyano-1-(2,3,4-trichlorophenyl)pyrazole, 4-cyano-5-cyclohexylcarbonamido-1-(2,6-dichloro-4-trifluoromethylphenyl)pyrazole, 4-cyano-1-(2,6-dibromo-4-trifluoromethylphenyl)-5-propionamidopyrazole, 5-(3-trichloro-2,2-dimethylpropionamido)-4-cyano-1-(2,3,4-trichlorophenyl)pyrazole, 4-cyano-5-dichloroacetamido-1-(2,6-dichloro-4-trifluoromethylphenyl)pyrazole, 1-(2-chloro-4-trifluoromethylphenyl)-4-cyano-5-dichloroacetamidopyrazole, 1-(2-chloro-4-trifluoromethylphenyl)-4-cyano-5-heptanamidopyrazole, 4-cyano-5-cyclopentylcarbonamido-1-(2,6-dichloro-4-trifluoromethylphenyl)pyrazole, 4-cyano-1-(2,6-dichloro-4-trifluoromethylphenyl)-5-heptanamidopyrazole, 5-acetamido-4-cyano-1-(2,4-dichloro-6-methylphenyl)pyrazole, 4-cyano-1-(2,4-dichloro-6-methylphenyl)-5-propionamidopyrazole, 4-cyano-5-propionamido-1-(2,3,4,6-tetrafluoropheny)pyrazole, 4-cyano-5-cyclobutylcarbonamido-1-(2,6-dichloro-4-trifluoromethylphenyl)pyrazole, 1-(2-chloro-4-trifluoromethylphenyl)-4-cyano-5-cyclobutylcarbonamidopyrazole, 4-cyano-1-(2-nitro-4-trifluoromethylphenyl)-5-propionamidopyrazole, 4-cyano-5-isopropoxycarbonylamino-1-(2,3,5,6-tetrafluoro-4-trifluoromethylphenyl)pyrazole, 5-(4-chloropentanamido)-4-cyano-1-(2,3,4-trichlorophenyl)pyrazole, 1-(2-chloro-4-trifluoromethylphenyl)-4-cyano-5-(2-ethyl-3-methylbutyramido)pyrazole, 4-cyano-5-succinimido-1-(2,3,4-trichlorophenyl)pyrazole, 4-cyano-5-glutarimido-1-(2,3,4-trichlorophenyl)pyrazole, 4-cyano-5-diheptanoylamino-1-(2,3,4-trichlorophenyl)pyrazole, 1-(2-chloro-4-isopropylphenyl)-4-cyano-5-diacetylaminopyrazole, 5-(N-acetyl-N-heptanoyl)amino-4-cyano-1-(2,3,4-trichlorophenyl)pyrazole, 4-cyano-1-(2,6-dichloro-4-trifluoromethylphenyl)-5-succinimidopyrazole, 1-(2-chloro-4-trifluoromethylphenyl)-4-cyano-5-succinimidopyrazole, 4-cyano-1-(2,6-dichloro-4-trifluoromethylphenyl)-5-glutarimidopyrazole, 4-cyano-5-diacetylamino-1-(2,4-dichloro-6-methylphenyl)pyrazole, 1-(4-n-butyl-2,3,5,6-tetrafluorophenyl)-4-cyano-5-diacetylaminopyrazole, 4-cyano-5-diacetylamino-1-pentafluorophenylpyrazole, 4-cyano-5-diacetylamino-1-(2,3,4,6-tetrafluorophenyl)pyrazole, 1-(2-chloro-4-methylphenyl)-4-cyano-5-diacetylaminopyrazole, 4-cyano-5-methylsuccinimido-1-(2,3,4-trichlorophenyl)pyrazole, 1-(2-chloro-4-trifluoromethylphenyl)-4-cyano-5-glutarimidopyrazole, 4-cyano-1-(2,6-dichloro-4-trifluoromethylphenyl)-5-di(phenoxycarbonyl)aminopyrazole, 5-acetamido-1-(2-bromo-4-trifluoromethylphenyl)-4-cyanopyrazole, 1-(2-chloro-4-methylphenyl)-5-(3-chlorobutyramido)-4-cyanopyrazole, 1-(4-n-butyl-2,3,5,6-tetrafluorophenyl)-4-cyano-5-propionamidopyrazole, 4-cyano-1-(2,6-dichloro-4-trifluoromethylphenyl)-5-(2-ethyl-3-methylbutyramido)pyrazole, 1-(2-bromo-4-trifluoromethylphenyl)-4-cyano-5-diacetylaminopyrazole, 4-cyano-5-diacetylamino-1-(2-nitro-4-trifluoromethylphenyl)pyrazole, 4-cyano-1-(2,6-dichloro-4-trifluoromethylphenyl)-5-(4-ethoxycarbonylbutyramido)pyrazole, 4-cyano-1-(4-methyl-2,3,6-trichlorophenyl)-5-propionamidopyrazole, 5-acetamido-1-[4-sec-butyl-2,3,5,6-tetrafluorophenyl]-4-cyanopyrazole, 5-acetamido-4-cyano-1-(2,3,5,6-tetrafluoro-4-vinylphenyl)pyrazole, 1-[4-sec-butyl-2,3,5,6-tetrafluorophenyl]-4-cyano-5-diacetylaminopyrazole, 1-(2-chloro-4-n-propylphenyl)-4-cyano-5-propionamidopyrazole, 1-[4-sec-butyl-2,3,5,6-tetrafluorophenyl]-4-cyano-5-propionamidopyrazole, 4-cyano-1-(2,3-dichloro-4-methylphenyl)-5-propionamidopyrazole, 5-acetamido-1-(4-bromo-2,3,5,6-tetrafluorophenyl)-4-cyanopyrazole, 5-acetamido-4-cyano-1-(2,3-dichloro-4-methylphenyl)-pyrazole, 4-cyano-5-diacetylamino-1-(2,3-dichloro-4-methylphenyl)pyrazole, or 4-cyano-5-(2,2-dimethylsuccinimido)-1-(2,3,4-trichlorophenyl)pyrazole.

22. A herbicidal composition which comprises, as active ingredient, a herbicidally effective amount of an acylamino-N-phenylpyrazole derivative of the general formula depicted in claim 1, wherein $R^1$, $R^2$, $R^3$, $R^4$, $R^5$, $R^6$ and $R^7$ are as defined in claim 1 in association with one or more compatible herbicidally-acceptable diluents or carriers.

23. A herbicidal composition according to claim 22 which contains from 0.05 to 90% by weight of acylamino-N-phenylpyrazole derivative.

24. A herbicidal composition according to claim 22 or 23 which contains from 0.05 to 25% of surface-active agent.

25. A herbicidal composition according to claim 22 or 23 which contains from 0.05 to 10% of surface-active agent.

26. A herbicidal composition according to claim 22 or 23 in which the acylamino-N-phenylpyrazole derivative incorporated in the composition is a compound claimed in any one of claims 2 to 21.

27. A method of controlling the growth of weeds at a locus which comprises applying to the locus a herbicidal composition which comprises an an active ingredient a herbicidally effective amount of an acylamino-N-phenyl-pyrazole derivative of the general formula depicted in claim 1, wherein $R^1$, $R^2$, $R^3$, $R^4$, $R^5$, $R^6$ and $R^7$ are as defined in claim 1, in association with one or more compatible herbicidally acceptable diluents or carriers.

28. A method according to claim 27 in which the weeds are braod-leafed weeds selected from *Aethusa cynapium, Abutilon theophrasti, Amaranthus retroflexum, Amsinckia intermedia, Anagallis arvensis, Anthemis arvensis, Atriplex patula, Bidens pilosa, Brassica nigra, Capsella bursa-pastoris, Chenopodium album, Chrysanthemum segetum, Cirsium arvense, Datura stramonium, Desmodium tortuosum, Emex australis, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata,* Polygonum spp., (e.g. *Polygonum lapathifolium, Polygonum aviculare, Polygonum convolvulus* and *Polygonum persicaria*), *Portulaca oleracea, Raphanus raphanistrum, Rotala indica, Rumex obtusifolius, Saponaria vaccaria, Scandix pectenveneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Xanthium strumarium*.

29. A method according to claim 27 in which the weeds are broad-leafed weeds selected from *Alopecurus myosuroides, Apera spica-venti, Agrostis stolonifera, Avena fatua, Avena ludoviciana,* Brachiaria spp., *Bromus sterilis, Bromus tectorum,* Cenchrus spp., *Cynodon dactylon, Digitaria sanquinalis, Echinochloa crus-galli, Eleusine indica, Setaria viridis* and *Sorghum halepense* and sedges, (e.g. *Cyperus esculentus, Cyperus iria* and *Cyperus rotundus*), and *Eleocharis acicularis.*

30. A method according to claim 27 wherein the acylamino-N-phenylpyrazole derivative is applied pre- or post-emergence of the weeds.

31. A method according to claim 27 wherein the acylamino-N-phenylpyrazole derivative is applied post-emergence of the weeds.

32. A method according to claim 27 in which the herbicidal composition is applied to an area used, or to be used, for growing crops.

33. A method according to claim 32 in which the herbicidal composition is applied to a crop-growing area at a rate sufficient to control the growth of weeds without causing substantial permanent damage to the crop.

34. A method according to claim 27 in which the acylamino-N-phenylpyrazole derivative is applied at a rate between 0.01 kg and 10 kg per hectare.

35. A method according to claim 33 in which the crop is a cereal, soya beans, field or dwarf beans, peas, lucerne, cotton, peanuts, flax, onions, carrots, cabbage, oilseed rape, sunflower, sugar beet, or permanent or sown grassland.

36. A method according to claim 33 in which the crop is wheat, barley, oats, maize or rice.

37. A method according to claim 33 in which the acylamino-N-phenylpyrazole derivative is applied at a rate between 0.01 kg and 4.0 kg per hectare.

38. A method according to claim 33 in which the acylamino-N-phenylpyrazole derivative is applied at a rate between 0.01 kg and 2.0 kg per hectare.

39. A method according to claim 37 in which the herbicidal composition is applied for the control of broad-leafed weeds in an area used for growing a cereal crop before or after emergence of both the crop and weeds.

40. A method according to claim 39 in which the herbicidal composition is applied post-emergence of the broad-leafed weeds.

41. A method according to claim 37 or 38 in which the herbicidal composition is applied for the control of broad-leafed weeds in an area to be used for growing soya beans or cotton before emergence of both the crop and weeds.

42. A method according to claim 37 in which the acylamino-N-phenylpyrazole derivative applied to the locus is a compound claimed in any one of claims 2 to 21.

* * * * *